US012715853B2

(12) United States Patent
Woo et al.

(10) Patent No.: US 12,715,853 B2
(45) Date of Patent: Aug. 25, 2026

(54) 5-AMINO-2-PIPERIDINON-3-YL-1-OXOISOINDOLINE DERIVATIVES FOR DEGRADATION OF IKZF2 DEGRADERS

(71) Applicants: President and Fellows of Harvard College, Cambridge, MA (US); Memorial Sloan-Kettering Cancer Center, New York, NY (US)

(72) Inventors: Christina M. Woo, Cambridge, MA (US); David K. Miyamoto, Cambridge, MA (US); Michael Kharas, New York, NY (US); Sun Mi Park, New York, NY (US)

(73) Assignees: President and Fellows of Harvard College, Cambridge, MA (US); Memorial Sloan-Kettering Cancer Center, New York, NY (US)

( * ) Notice: Subject to any disclaimer, the term of this patent is extended or adjusted under 35 U.S.C. 154(b) by 824 days.

(21) Appl. No.: 17/997,484

(22) PCT Filed: Apr. 29, 2021

(86) PCT No.: PCT/US2021/029861
§ 371 (c)(1),
(2) Date: Oct. 28, 2022

(87) PCT Pub. No.: WO2021/222542
PCT Pub. Date: Nov. 4, 2021

(65) Prior Publication Data

US 2023/0167081 A1 Jun. 1, 2023

Related U.S. Application Data

(60) Provisional application No. 63/018,122, filed on Apr. 30, 2020.

(51) Int. Cl.
*C07D 401/04* (2006.01)
*A61P 35/02* (2006.01)
*C07D 401/14* (2006.01)
*C07D 405/14* (2006.01)

(52) U.S. Cl.
CPC ............ *C07D 401/04* (2013.01); *A61P 35/02* (2018.01); *C07D 401/14* (2013.01); *C07D 405/14* (2013.01); *C07B 2200/05* (2013.01)

(58) Field of Classification Search
CPC .. C07D 401/04; C07D 401/14; C07D 405/14; A61P 35/02
See application file for complete search history.

(56) References Cited

U.S. PATENT DOCUMENTS 5,635,517 A 6/1997 Muller et al.
6,335,349 B1 1/2002 Muller et al.
8,129,375 B2 3/2012 Muller et al.
8,877,780 B2 11/2014 Muller et al.
9,193,989 B2 11/2015 Park et al.
9,227,954 B2 1/2016 Muller et al.
9,796,698 B2 10/2017 Muller et al.
10,125,114 B2 11/2018 Bradner et al.
2003/0096841 A1* 5/2003 Robarge .................... A61P 1/04 514/323
2009/0232796 A1 9/2009 Corral et al.
2012/0252843 A1 10/2012 Muller et al.
2018/0099940 A1 4/2018 Crew et al.
2018/0155322 A1 6/2018 Crew et al.
2018/0215731 A1 8/2018 Crew et al.
2018/0237418 A1 8/2018 Crew et al.
2018/0273472 A1 9/2018 Greig et al.
2020/0022966 A1 1/2020 Tang et al.
2021/0309638 A1 10/2021 Beckwith et al.
2022/0017938 A1 1/2022 Mikkelsen et al.
2024/0383886 A1* 11/2024 Veits .................... A61K 31/454
2026/0021103 A1 1/2026 Woo et al.

FOREIGN PATENT DOCUMENTS

WO WO 2008/027542 A2 3/2008
WO WO 2014/180882 A2 11/2014
WO WO 2017/197056 A1 11/2017
WO WO 2018/214796 A1 11/2018
WO WO 2019/133531 A1 7/2019
WO WO 2019/191112 A1 10/2019
WO WO 2020/038415 A1 2/2020
WO WO 2020/098280 A1 5/2020
(Continued)

OTHER PUBLICATIONS

Hu, Bioorganic & Medicinal Chemistry Letters, 27, 2017, 4075-4081 (Year: 2017).*
STN RN 2412058-18-3 (Entered Registry: Mar. 18, 2020) (Year: 2020).*
IKZF2, https://web.archive.org/web/20170510080749/https://www.proteinatlas.org/ENSG00000030419-IKZF2/cancer (Year: 2017).*
The Human Protein Atlas, IKZF2, https://web.archive.org/web/20170510080749/https://www.proteinatlas.org/ENSG00000030419-IKZF2/cancer (Year: 2017).*
Park, Cell Stem Cell, 24, 1, pp. 153-165, Jan. 3, 2019 (Year: 2019).*
Xu, Acta Dermato Venereologica, Dec. 7, 2021, 101 (12): 570 (Year: 2021).*
Kaur, Global Journal of Pharmacy and Pharmaceutical Science, vol. 1, Issue 4, Mar. 2017 (Year: 2017).*
(Continued)

*Primary Examiner* — Andrew D Kosar
*Assistant Examiner* — Phillip Matthew Rzeczycki
(74) *Attorney, Agent, or Firm* — Wolf, Greenfield & Sacks, P.C.

(57) ABSTRACT

Provided herein are compounds that promote targeted degradation of IKZF2, a protein whose activity is implicated in the pathology of certain cancers (e.g., acute myeloid leukemia). Also provided are pharmaceutical compositions comprising the compounds. Also provided are methods of treating cancer, and methods of promoting the degradation of IKZF2 in a subject or biological sample by administering a compound or composition described herein.

20 Claims, 9 Drawing Sheets

(56) References Cited

FOREIGN PATENT DOCUMENTS

| | | | |
|---|---|---|---|
| WO | WO 2020/160192 | A1 | 8/2020 |
| WO | WO 2020/160196 | A1 | 8/2020 |
| WO | WO 2020/264172 | A1 | 12/2020 |
| WO | WO 2021/126974 | A1 | 6/2021 |
| WO | WO 2021/127586 | A1 | 6/2021 |
| WO | WO 2021/222542 | A1 | 11/2021 |
| WO | WO 2022/066835 | A1 | 3/2022 |

OTHER PUBLICATIONS

International Search Report and Written Opinion for Application No. PCT/US2021/029861, mailed Sep. 16, 2021.
International Preliminary Report on Patentability for Application No. PCT/US2021/029861, mailed Nov. 10, 2022.
American Cancer Society, Cancer Facts & Figures 2017. American Cancer Society. 2017. 76 Pages.
Asanuma et al., Adult T-cell leukemia cells are characterized by abnormalities of Helios expression that promote T cell growth. Cancer Sci. Aug. 2013;104(8):1097-106. doi: 10.1111/cas.12181. Epub May 19, 2013.
Cancer Genome Atlas Research, Genomic and epigenomic landscapes of adult de novo acute myeloid leukemia. N Engl J Med. May 30, 2013;368(22):2059-74. doi: 10.1056/NEJMoa1301689. Epub May 1, 2013.
Chamberlain et al., Structure of the human Cereblon-DDB1-lenalidomide complex reveals basis for responsiveness to thalidomide analogs. Nat Struct Mol Biol. Sep. 2014;21(9):803-9. doi: 10.1038/nsmb.2874. Epub Aug. 10, 2014.
De Genst et al., Structure and properties of a complex of α-synuclein and a single-domain camelid antibody. J Mol Biol. Sep. 17, 2010;402(2):326-43. doi: 10.1016/j.jmb.2010.07.001. Epub Jul. 8, 2010.
Fink et al., CrbnI391V is sufficient to confer in vivo sensitivity to thalidomide and its derivatives in mice. Blood. Oct. 4, 2018;132(14):1535-1544. doi: 10.1182/blood-2018-05-852798. Epub Jul. 31, 2018.
Gonsalves et al., The next generation of novel therapies for the management of relapsed multiple myeloma. Future Oncol. Jan. 2017;13(1):63-75. doi: 10.2217/fon-2016-0200. Epub Aug. 11, 2016.
Grzanka et al., FoxP3, Helios, and SATB1: roles and relationships in regulatory T cells. Int Immunopharmacol. Jul. 2013;16(3):343-7. doi: 10.1016/j.intimp.2013.02.004. Epub Feb. 18, 2013.
Hansen et al., Discovery of CRBN E3 Ligase Modulator CC-92480 for the Treatment of Relapsed and Refractory Multiple Myeloma. J Med Chem. Jul. 9, 2020;63(13):6648-6676. doi: 10.1021/acs.jmedchem.9b01928. Epub Mar. 19, 2020.
Huntly et al., Leukaemia stem cells and the evolution of cancer-stem-cell research. Nat Rev Cancer. Apr. 2005;5(4):311-21. doi: 10.1038/nrc1592.
Iacobucci et al., Genetic Basis of Acute Lymphoblastic Leukemia. J Clin Oncol. Mar. 20, 2017;35(9):975-983. doi: 10.1200/JCO.2016.70.7836. Epub Feb. 13, 2017.
Ishikawa et al., Chemotherapy-resistant human AML stem cells home to and engraft within the bone-marrow endosteal region. Nat Biotechnol. Nov. 2007;25(11):1315-21. doi: 10.1038/nbt1350. Epub Oct. 21, 2007.
Ito et al., Identification of a Primary Target of Thalidomide Teratogenicity. Science. Mar. 12, 2010;327(5971):1345-50. doi: 10.1126/science.1177319.
John et al., The Ikaros gene family: Transcriptional regulators of hematopoiesis and immunity. Mol Immunol. May 2011;48(9-10):1272-8. doi: 10.1016/j.molimm.2011.03.006. Epub Apr. 7, 2011.
Jordan et al., Cancer stem cells. N Engl J Med. Sep. 21, 2006;355(12):1253-61. doi: 10.1056/NEJMra061808.
Kim et al., Stable inhibitory activity of regulatory T cells requires the transcription factor Helios. Science. Oct. 16, 2015;350(6258):334-9. doi: 10.1126/science.aad0616.
Kreso et al., Evolution of the Cancer Stem Cell Model. Cell Stem Cell. Mar. 6, 2014;14(3):275-91. doi: 10.1016/j.stem.2014.02.006.
Kronke et al., IKZF1 expression is a prognostic marker in newly diagnosed standard-risk multiple myeloma treated with lenalidomide and intensive chemotherapy: a study of the German Myeloma Study Group (DSMM). Leukemia. Jun. 2017;31(6):1363-1367. doi: 10.1038/leu.2016.384. Epub Dec. 26, 2016.
Kronke et al., Lenalidomide Causes Selective Degradation of IKZF1 and IKZF3 in Multiple Myeloma Cells. Science. Jan. 17, 2014;343(6168):301-5. doi: 10.1126/science.1244851. Epub Nov. 29, 2013.
Kronke et al., Lenalidomide induces degradation of IKZF1 and IKZF3. Oncoimmunology. Jul. 3, 2014;3(7):e941742. doi: 10.4161/21624011.2014.941742. eCollection 2014.
Kronke et al., Lenalidomide inducesubiquitination and degradation of CK1[agr] in del(5q) MDS. Nature. 2015; 523: 183-188. https://doi.org/10.1038/nature14610.
Lu et al., Hijacking the E3 Ubiquitin Ligase Cereblon to Efficiently Target BRD4. Chem Biol. Jun. 18, 2015;22(6):755-63. doi: 10.1016/j.chembiol.2015.05.009. Epub Jun. 4, 2015.
Lu et al., The Myeloma Drug Lenalidomide Promotes the Cereblon-Dependent Destruction of Ikaros Proteins. Science. Jan. 17, 2014;343(6168):305-9. doi: 10.1126/science.1244917. Epub Nov. 29, 2013.
Matulic et al., Analysis of Ikaros family splicing variants in human hematopoietic lineages. Coll Antropol. Mar. 2010;34(1):59-62.
Matyskiela et al., A novel cereblon modulator recruits GSPT1 to the CRL4(CRBN) ubiquitin ligase. Nature. Jul. 14, 2016;535(7611):252-7. doi: 10.1038/nature18611. Epub Jun. 22, 2016.
Maynadie et al., Twenty-five years of epidemiological recording on myeloid malignancies: data from the specialized registry of hematologic malignancies of Cote d'Or (Burgundy, France). Haematologica. Jan. 2011;96(1):55-61. doi: 10.3324/haematol.2010.026252. Epub Oct. 22, 2010.
Minuesa et al., Small-molecule targeting of MUSASHI RNA-binding activity in acute myeloid leukemia. Nat Commun. Jun. 19, 2019;10(1):2691. doi: 10.1038/s41467-019-10523-3.
Minzel et al., Small Molecules Co-targeting CKIalpha and the Transcriptional Kinases CDK7/9 Control AML in Preclinical Models. Cell. Sep. 20, 2018;175(1):171-185.e25. doi: 10.1016/j.cell.2018.07.045. Epub Aug. 23, 2018.
Park et al., IKZF2 Drives Leukemia Stem Cell Self-Renewal and Inhibits Myeloid Differentiation. Cell Stem Cell. Jan. 3, 2019;24(1):153-165.e7. doi: 10.1016/j.stem.2018.10.016. Epub Nov. 21, 2018.
Park et al., Musashi2 sustains the mixed-lineage leukemia-driven stem cell regulatory program. J Clin Invest. Mar. 2, 2015;125(3):1286-98. doi: 10.1172/JCI78440. Epub Feb. 9, 2015.
Patel et al., Prognostic relevance of integrated genetic profiling in acute myeloid leukemia. N Engl J Med. Mar. 22, 2012;366(12):1079-89. doi: 10.1056/NEJMoa1112304. Epub Mar. 14, 2012.
Patil et al., CK1alpha and IRF4 are essential and independent effectors of immunomodulatory drugs in primary effusion lymphoma. Blood. Aug. 9, 2018;132(6):577-586. doi: 10.1182/blood-2018-01-828418. Epub Jun. 28, 2018.
Rebollo et al., Ikaros, Aiolos and Helios: transcription regulators and lymphoid Malignancies. Immunol Cell Biol. Jun. 2003;81(3):171-5. doi: 10.1046/j.1440-1711.2003.01159.x.
Rehman et al., The Rise, Fall and Subsequent Triumph of Thalidomide: Lessons Learned in Drug Development. Ther Adv Hematol. Oct. 2011;2(5):291-308. doi: 10.1177/2040620711413165.
Rena et al., D4476, a cell-permeant inhibitor of CK1, suppresses the sitespecific phosphorylation and nuclear exclusion of FOXO1a. EMBO Rep. Jan. 2004;5(1):60-5. doi: 10.1038/sj.embor.7400048.
Sievers et al., Defining the human C2H2 zinc finger degrome targeted by thalidomide analogs through CRBN. Science. Nov. 2, 2018;362(6414):eaat0572. doi: 10.1126/science.aat0572.
Tabayashi et al. Characterization of the short isoform of Helios overexpressed in patients with T-cell malignancies. Cancer Sci. Feb. 2007;98(2):182-8. doi: 10.1111/j.1349-7006.2006.00372.x.
Tian et al., Isolation and characterization of antibody fragments selective for toxic oligomeric tau. Neurobiol Aging. Mar. 2015;36(3):1342-55. doi: 10.1016/j.neurobiolaging.2014.12.002. Epub Dec. 11, 2014.

(56) References Cited

OTHER PUBLICATIONS

Tonnelle et al., Ikaros gene expression and Leukemia. Leuk Lymphoma. Jan. 2002;43(1):29-35. doi: 10.1080/10428190210186.
Uhlen et al., A pathology atlas of the human cancer transcriptome. Science. Aug. 18, 2017;357(6352):eaan2507. doi: 10.1126/science.aan2507.
Vu et al., Functional screen of MSI2 interactors identifies an essential role for SYNCRIP in myeloid leukemia stem cells. Nat Genet. Jun. 2017;49(6):866-875. doi: 10.1038/ng.3854. Epub Apr. 24, 2017.
Wu et al., Development of Multifunctional Histone Deacetylase 6 Degraders with Potent Antimyeloma Activity. J Med Chem. Aug. 8, 2019;62(15):7042-7057. doi: 10.1021/acs.jmedchem.9b00516. Epub Jul. 17, 2019.
Yu et al., High-throughput identification of genotype-specific cancer vulnerabilities in mixtures of barcoded tumor cell lines. Nat Biotechnol. Apr. 2016;34(4):419-23. doi: 10.1038/nbt.3460. Epub Feb. 29, 2016.
Zhang et al. Expression of a non-DNA-binding isoform of Helios induces T-cell lymphoma in mice. Blood. Mar. 1, 2007;109(5):2190-7. doi: 10.1182/blood-2005-01-031930. Epub Nov. 16, 2006.
Zhang et al., CD4(+) T cells play a crucial role for lenalidomide in vivo anti-tumor activity in murine multiple myeloma. Oncotarget. Nov. 3, 2015;6(34):36032-40. doi: 10.18632/oncotarget.5506.
Zhao et al., Alternative Splice Variants Modulates Dominant-Negative Function of Helios in T-Cell Leukemia. PLoS One. Sep. 28, 2016;11(9):e0163328. doi: 10.1371/journal.pone.0163328. eCollection 2016.
Zhu et al., Molecular mechanism of action of immunemodulatory drugs thalidomide, lenalidomide and pomalidomide in multiple myeloma. Leuk Lymphoma. Apr. 2013;54(4):683-7. doi: 10.3109/10428194.2012.728597. Epub Sep. 28, 2012.
Zhu et al., Identification of cereblon-binding proteins and relationship with response and survival after IMiDs in multiple myeloma. Blood. Jul. 24, 2014;124(4):536-45. doi: 10.1182/blood-2014-02-557819. Epub Jun. 9, 2014.
Ersvaer et al., Intensive chemotherapy for acute myeloid leukemia differentially affects circulating TC1, TH1, TH17 and TREG cells. BMC Immunol. Jul. 9, 2010;11:38. doi: 10.1186/1471-2172-11-38.
Guenther et al., Aberrant chromatin at genes encoding stem cell regulators in human mixed-lineage leukemia. Genes Dev. Dec. 15, 2008;22(24):3403-8. doi: 10.1101/gad.1741408.
Kim et al., Cutting edge: depletion of Foxp3+ cells leads to induction of autoimmunity by specific ablation of regulatory T cells in genetically targeted mice. J Immunol. Dec. 15, 2009;183(12):7631-4. doi: 10.4049/jimmunol.0804308.
Kim et al., Regulatory T cells prevent catastrophic autoimmunity throughout the lifespan of mice. Nat Immunol. Feb. 2007;8(2):191-7. doi: 10.1038/ni1428. Epub Nov. 30, 2006.
Kwon et al., Tetraspanin 3 Is Required for the Development and Propagation of Acute Myelogenous Leukemia. Cell stem cell Aug. 6, 2015;17(2):152-164. doi: 10.1016/j.stem.2015.06.006. Epub Jul. 23, 2015.
Mullighan et al., Pediatric acute myeloid leukemia with NPM1 mutations is characterized by a gene expression profile with dysregulated HOX gene expression distinct from MLL-rearranged leukemias. Leukemia. Sep. 2007;21(9):2000-9. doi: 10.1038/sj.leu.2404808. Epub Jun. 28, 2007.
Park et al., Dual IKZF2 and CK1α degrader targets acute myeloid leukemia cells. Cancer Cell. Apr. 10, 2023;41(4):726-739.e11. doi: 10.1016/j.ccell.2023.02.010. Epub Mar. 9, 2023.
Szczepanski et al., Increased frequency and suppression by regulatory T cells in patients with acute myelogenous leukemia. Clin Cancer Res. May 15, 2009;15(10):3325-32. doi: 10.1158/1078-0432.CCR-08-3010. Epub May 5, 2009.
Wang et al., Increased population of CD4(+)CD25(high), regulatory T cells with their higher apoptotic and proliferating status in peripheral blood of acute myeloid leukemia patients. Eur J Haematol. Dec. 2005;75(6):468-76. doi: 10.1111/j.1600-0609.2005.00537.x.
Invitation to Pay Additional Fees for Application No. PCT/US2023/032595, mailed Nov. 3, 2023.
International Search Report and Written Opinion for Application No. PCT/US2023/032595, mailed Feb. 16, 2024.
International Preliminary Report on Patentability for Application No. PCT/US2023/032595, mailed Mar. 27, 2025.
No Author Listed, Pubchem SID 442742615. Aug. 21, 2021. 4 pages. Accessed at: https://pubchem.ncbi.nlm.nih.gov/substance/442742615 [last accessed Nov. 1, 2023].

* cited by examiner

DEG-37

5-AMINO-2-PIPERIDINON-3-YL-1-OXOISOINDOLINE DERIVATIVES FOR DEGRADATION OF IKZF2 DEGRADERS

RELATED APPLICATIONS

This application is a national stage filing under 35 U.S.C. § 371 of International PCT Application PCT/US2021/029861, filed Apr. 29, 2021, which claims priority under 35 U.S.C. § 119 (e) to U.S. Provisional Application, U.S. Ser. No. 63/018,122, filed Apr. 30, 2020, each of which is incorporated herein by reference.

BACKGROUND

The IKAROS family of proteins, comprising IKZF1-5, are zinc finger transcription factors that are key regulators of hematopoiesis and cell-fate decisions in the development of the adaptive immune system. The IKAROS family sustains adult human stem cell character, and dysregulation is observed in a number of hematological malignancies, including lymphomas, leukemias, and myelomas. IKZF1 and IKZF3 are essential transcription factors in multiple myeloma (MM). By contrast, IKZF2 controls lymphocyte development, promotes quiescence, and maintains inhibitory function of regulatory T cells. IKZF2 is frequently deleted in hypodiploid B-cell acute lymphoblastic leukemias (B-ALLs) and expression of dominant negative isoforms have been reported in T-cell acute lymphoblastic leukemia (T-ALL) patients, suggesting a role for IKZF2 as a tumor suppressor in lymphoid malignancies. IKZF2 is further associated with chronic myelogenous leukemia (CML) and is overexpressed in thyroid, urothelial, and cervical cancers. However, the regulatory role of IKZF2 in adult stem cell maintenance and the difficulty in developing inhibitors for transcription factors has prevented its broader exploration as an anti-cancer target to date.

Recently, IKZF2 was established as a viable target in acute myeloid leukemia (AML) through the key role of IKZF2 in maintenance of leukemia stem cell (LSC) function. LSCs are resistant to chemotherapy and drive relapse in clinical studies, and blocking self-renewal and differentiation could provide a novel therapeutic strategy. It was recently reported that IKZF2 was required for LSC function. IKZF2 depletion in human AML cell lines results in reduced proliferation, increased differentiation, increased apoptosis in vitro, and improved overall survival in mice. These properties establish IKZF2 as a bona fide anticancer target for the first time and creates a unique opportunity for the design of novel therapeutics targeting IKZF2.

Immunomodulatory agents (IMIDs), such as lenalidomide, have demonstrated efficacy in myelodysplastic syndromes and in multiple myeloma through targeting of IKAROS family members IKZF1 and IKZF3, however these agents do not promote degradation of IKZF2 or show substantive efficacy in AML.

SUMMARY

Known IMIDs, such as lenalidomide, are not degraders of IKZF2. But, compounds that can degrade IKZF2, a potential drug target for the treatment of hematological malignancies, may be useful therapeutic agents in the treatment of disease (e.g., acute myeloid leukemia). The present disclosure describes new compounds that can induce degradation of IKZF2 in cells. Thus, the present disclosure provides new compounds, compositions, kits, uses, and methods for the treatment of proliferative diseases (e.g., cancer, e.g., acute myeloid leukemia).

In one aspect, provided herein are compounds of Formula (I):

(I)

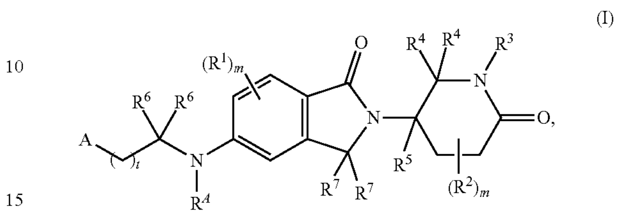

or a pharmaceutically acceptable salt, solvate, hydrate, polymorph, co-crystal, tautomer, stereoisomer, isotopically labeled derivative, or prodrug thereof, wherein:

A is substituted or unsubstituted aryl, or substituted or unsubstituted heteroaryl;

each $R^1$ is, independently, halogen, —$OR^A$, or substituted or unsubstituted $C_1$-$C_6$ alkyl;

each $R^2$ is, independently, halogen or $C_1$-$C_3$ alkyl;

$R^3$ is hydrogen or $C_1$-$C_3$ alkyl;

each $R^4$ is, independently, hydrogen or $C_1$-$C_3$ alkyl; or two $R^4$, together with the carbon atom to which they are attached, form a C═O, $C_3$-$C_6$ carbocycle, or a 4-6-membered heterocycle;

$R^5$ is hydrogen, halogen, or $C_1$-$C_3$ alkyl;

each $R^6$ is, independently, hydrogen, halogen, or $C_1$-$C_3$ alkyl; or two $R^6$, together with the carbon atom to which they are attached, form a C═O;

each $R^7$ is, independently, hydrogen or $C_1$-$C_3$ alkyl; or two $R^7$, together with the carbon atom to which they are attached, form a C═O;

each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom m is 0, 1,2 or 3;

n is 0, 1, or 2; and t is 0 or 1;

provided that the compound is not of formula:

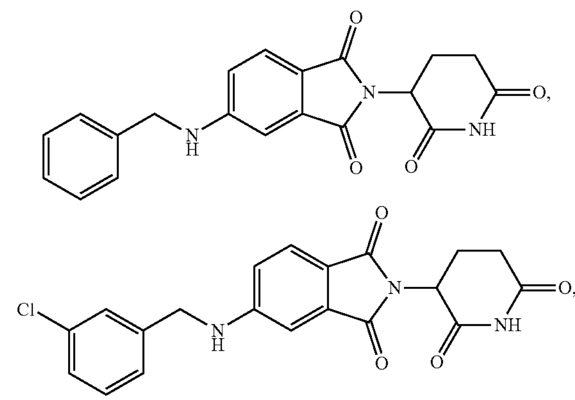

-continued

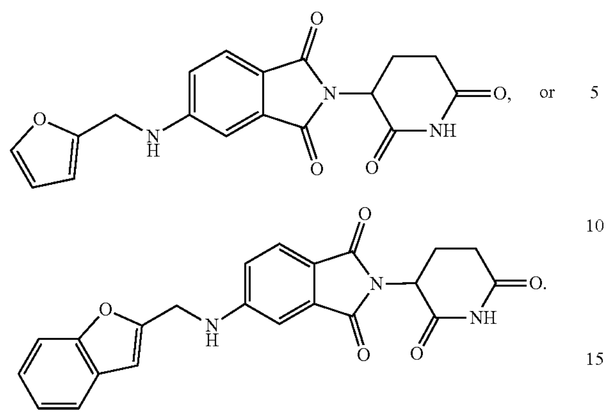

In certain embodiments, the compound of Formula (I) is of Formula (I-a), (I-b), (I-c), (I-d), (I-e), (I-f), (I-g), (I-h), (I-i), (I-j), (I-k), or (I-l):

(I-a)

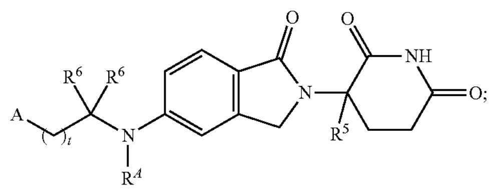

(I-b)

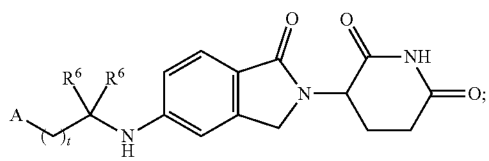

(I-c)

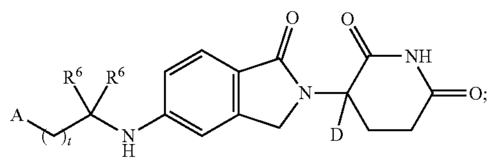

(I-d)

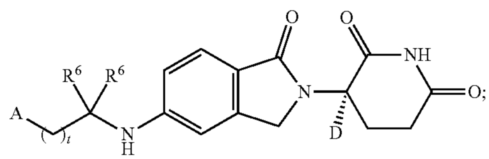

(I-e)

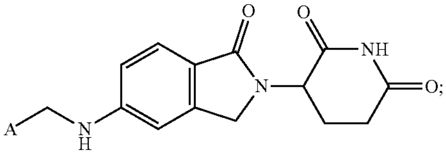

-continued (I-f)

(I-g)

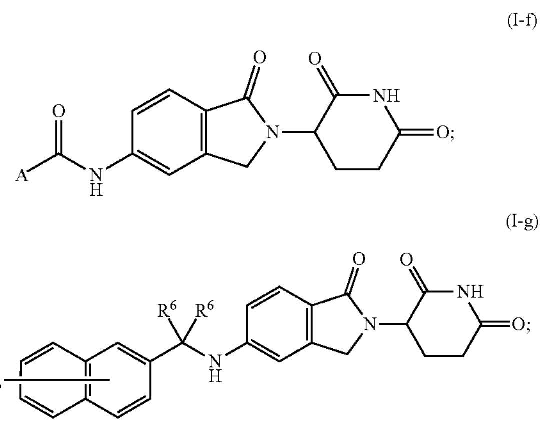

(I-h)

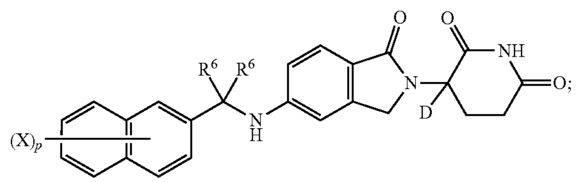

(I-i)

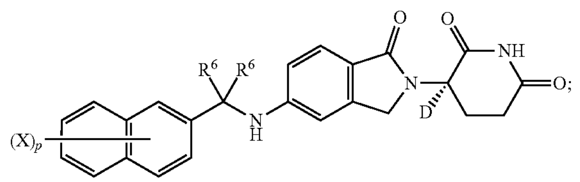

(I-j)

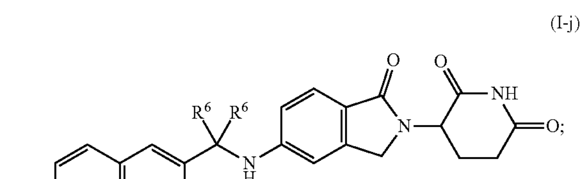

(I-k)

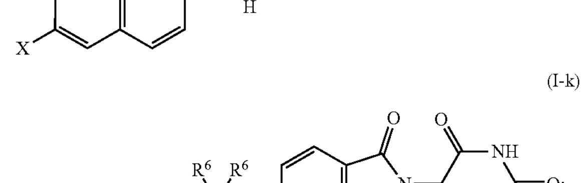

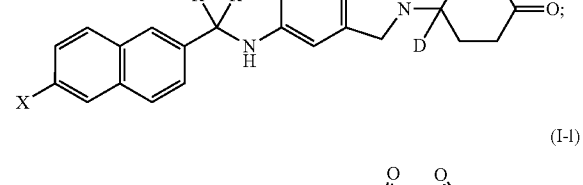

(I-l)

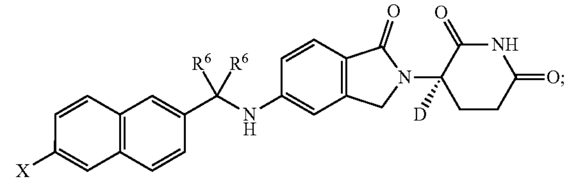

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to:

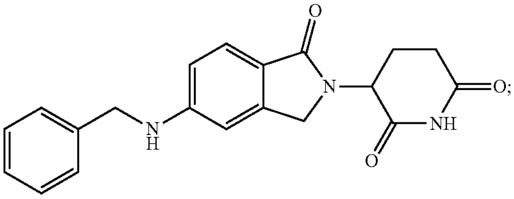
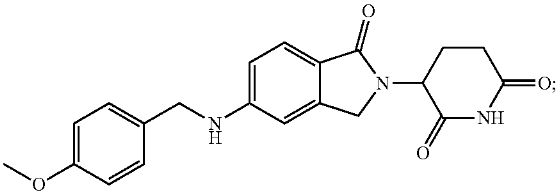
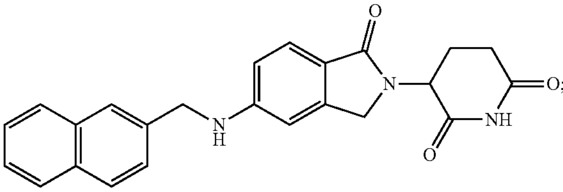
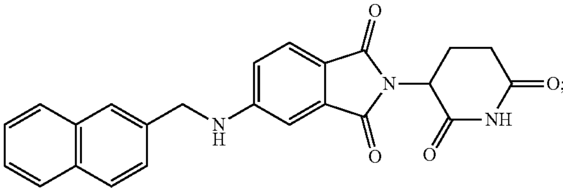
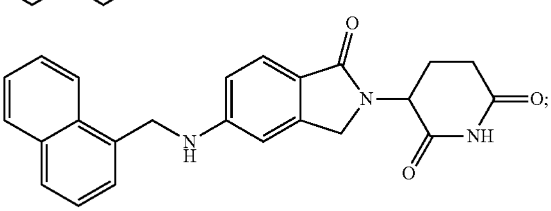
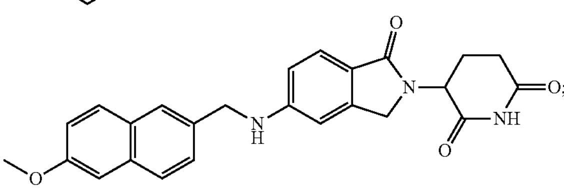
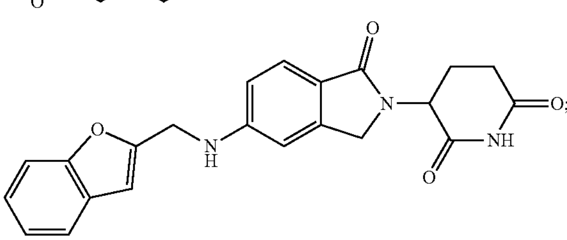
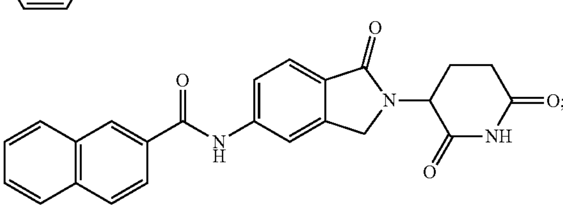
-continued
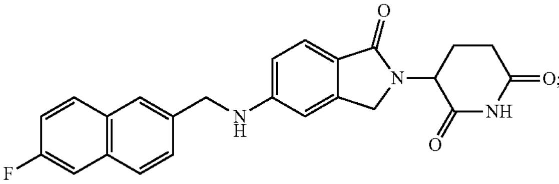
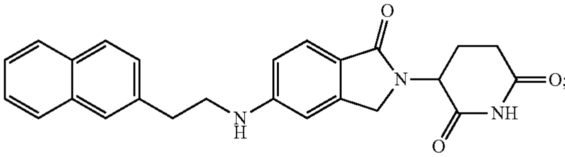
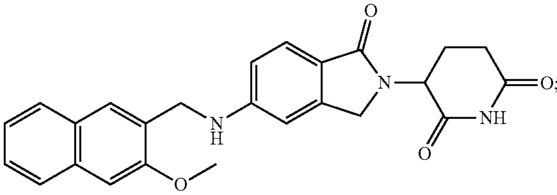
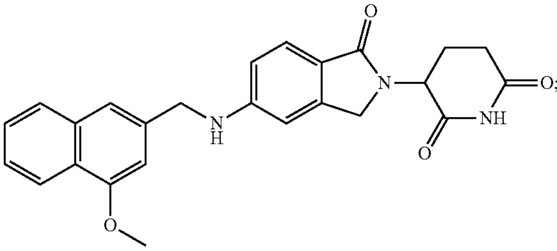
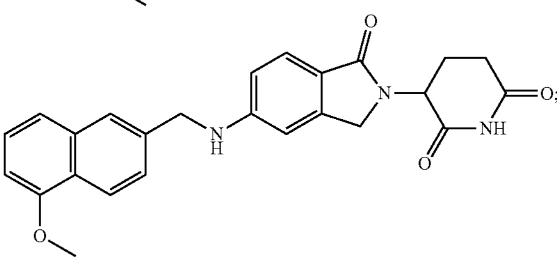
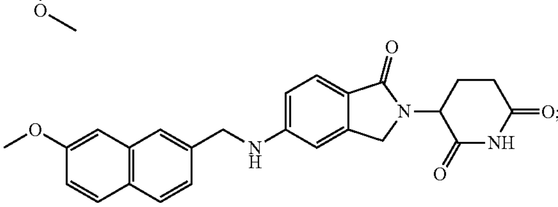
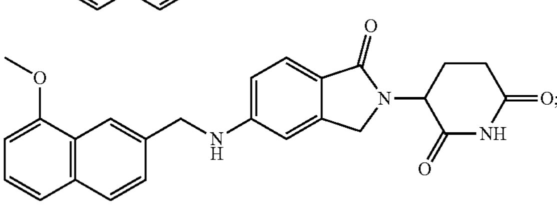
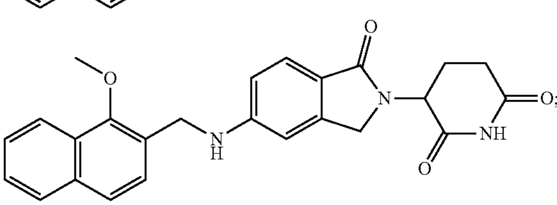

-continued
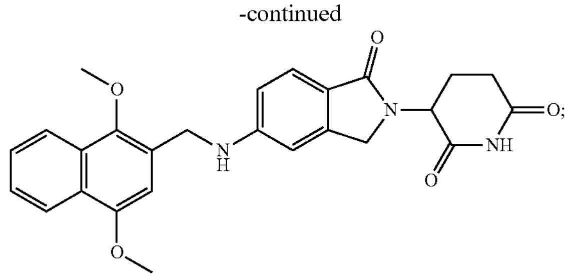
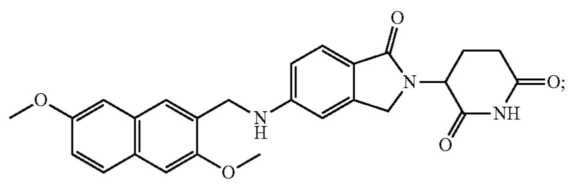
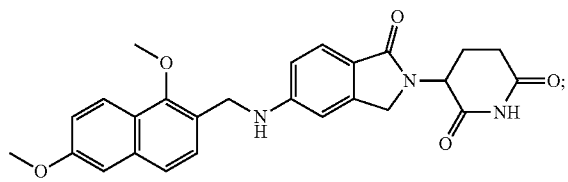
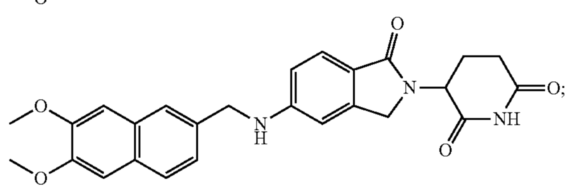
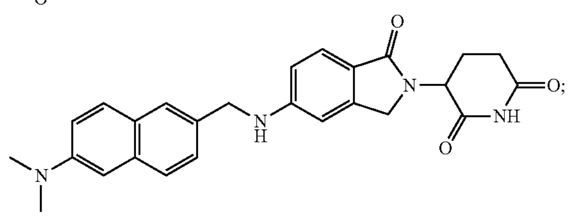
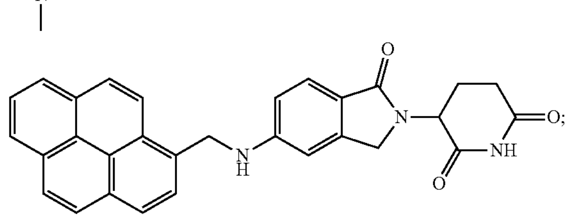
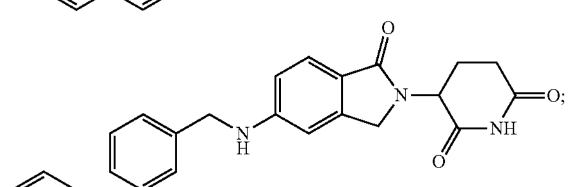
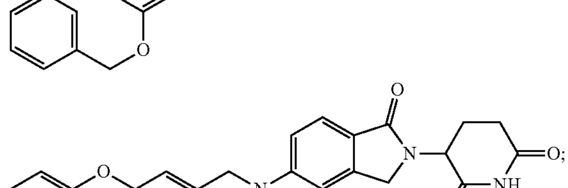
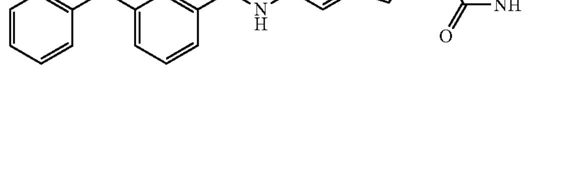
-continued
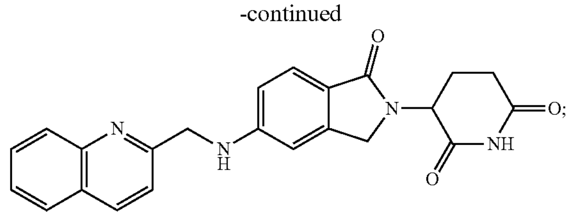
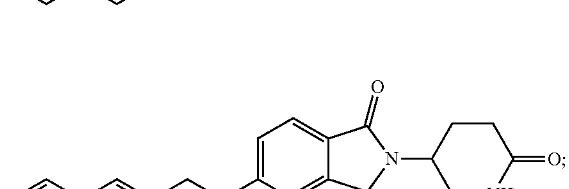
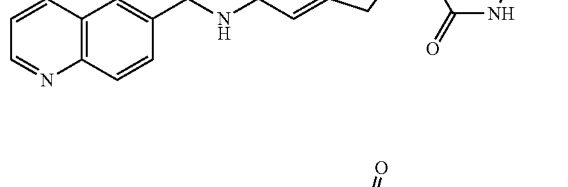
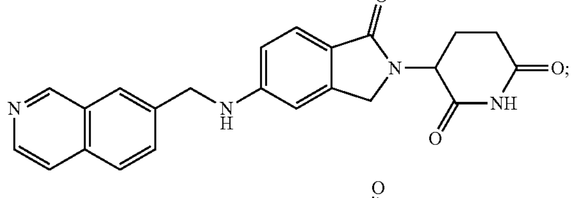
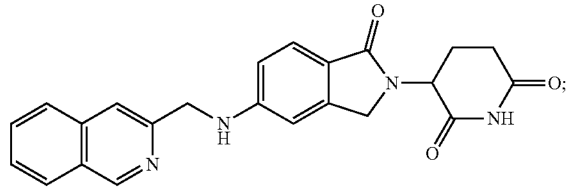
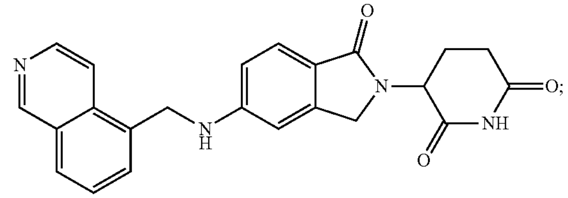
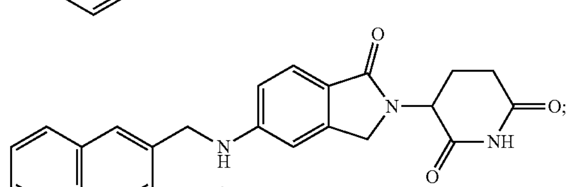
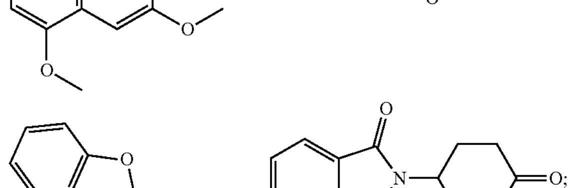
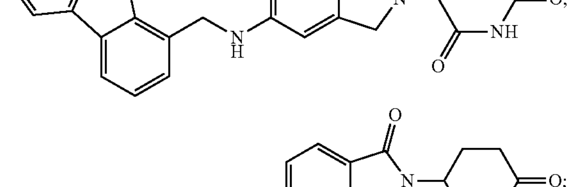
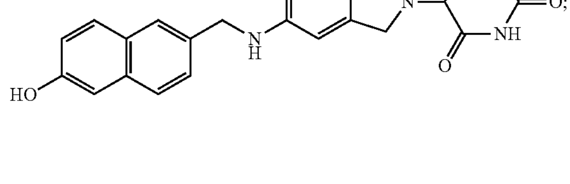
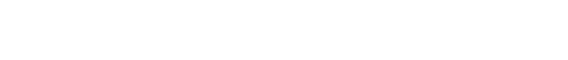

-continued

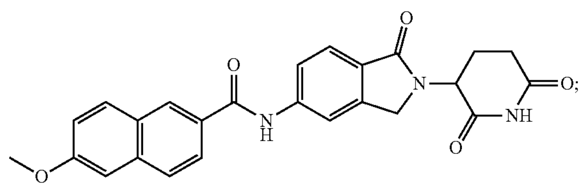

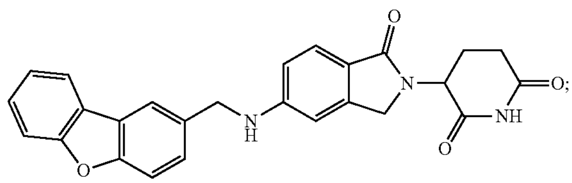

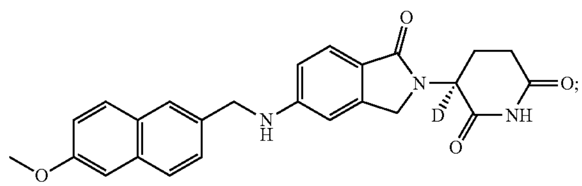

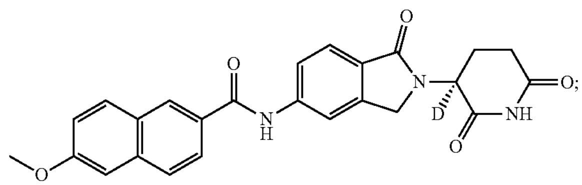

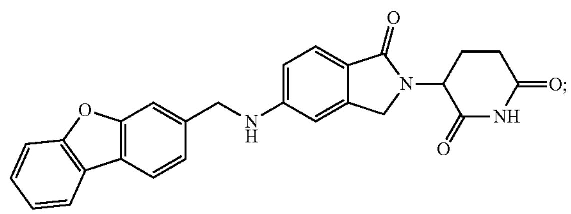

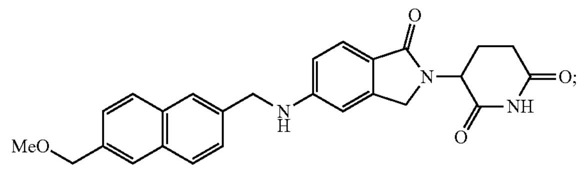

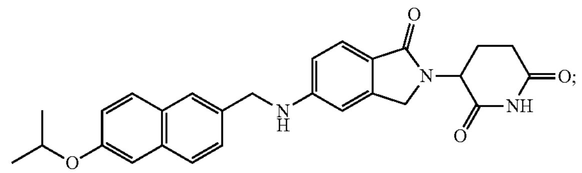

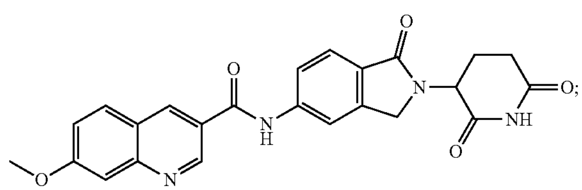

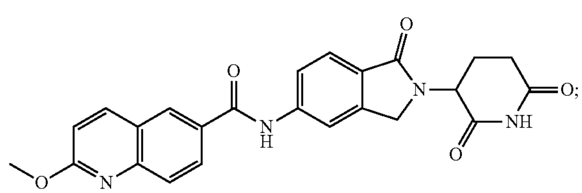

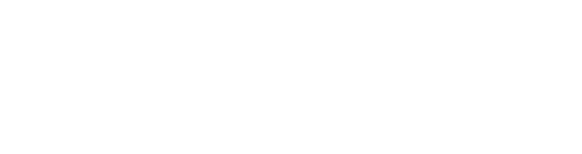

-continued

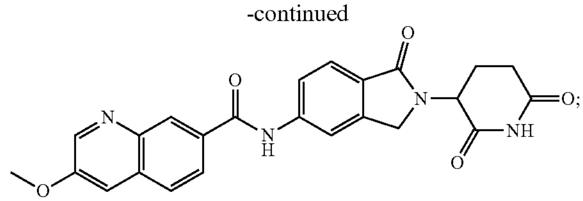

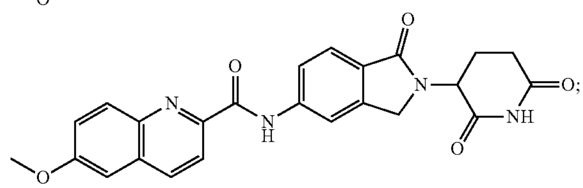

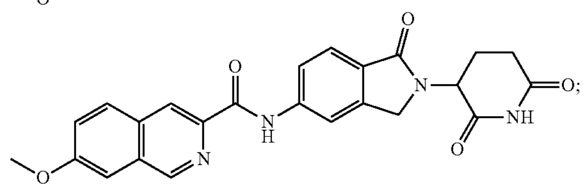

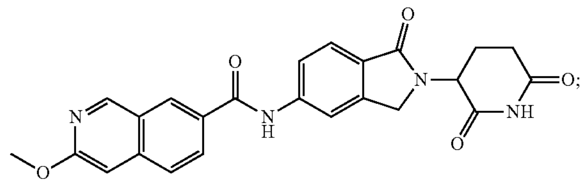

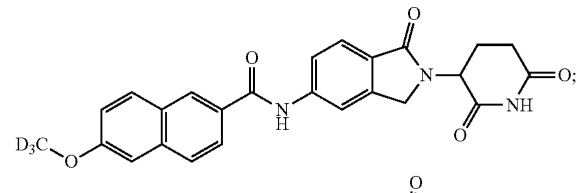

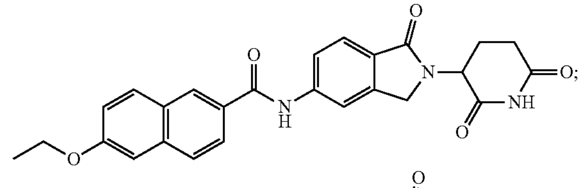

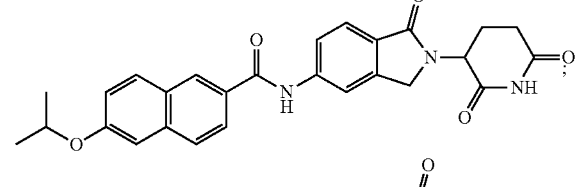

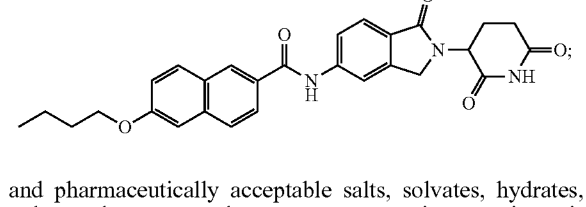

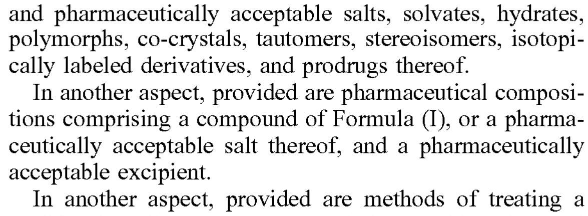

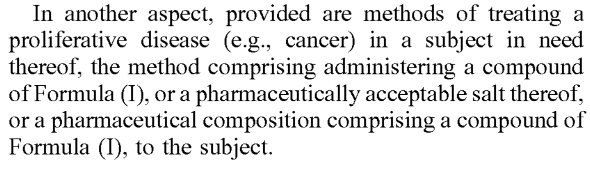

and pharmaceutically acceptable salts, solvates, hydrates, polymorphs, co-crystals, tautomers, stereoisomers, isotopically labeled derivatives, and prodrugs thereof.

In another aspect, provided are pharmaceutical compositions comprising a compound of Formula (I), or a pharmaceutically acceptable salt thereof, and a pharmaceutically acceptable excipient.

In another aspect, provided are methods of treating a proliferative disease (e.g., cancer) in a subject in need thereof, the method comprising administering a compound of Formula (I), or a pharmaceutically acceptable salt thereof, or a pharmaceutical composition comprising a compound of Formula (I), to the subject.

In another aspect, provided are methods of treating cancer in a subject in need thereof, the method comprising administering a compound of Formula (I), or a pharmaceutically acceptable salt thereof, or a pharmaceutical composition comprising a compound of Formula (I), to the subject. In certain embodiments, the cancer is a hematological cancer. In certain embodiments, the cancer is a leukemia or a lymphoma. In certain embodiments, the cancer is primary effusion lymphoma (PEL), del(5q) myelodysplastic syndrome (MDS), or acute myeloid leukemia (AML).

In another aspect, provided are methods of promoting the degradation of IKAROS family zinc finger 2 (IKZF2), the method comprising contacting IKZF2 with a compound of Formula (I), or a pharmaceutically acceptable salt thereof, or a pharmaceutical composition comprising a compound of Formula (I).

In another aspect, provided are kits comprising a compound of Formula (I), or a pharmaceutically acceptable salt thereof, or a pharmaceutical composition comprising a compound of Formula (I). In certain embodiments, the kit further comprises instructions for administration (e.g., human administration) and/or use.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

FIG. 1A. Degradation of IKZF2 and known neosubstrates using different degraders. Cells were treated at 25 μM. FIG. 1B. DEG-35 shows dose dependent degradation of IKZF2. FIG. 1C. DEG-35 degrades IKZF2 in MLL-AF9 cells with hCRBN but not mCRBN.

FIG. 2 shows phenotypic effects of IKZF2 degraders in MOLM13 cells.

FIG. 4 shows DEG-37 as an alternate lead compound for IKZF2 targeted degradation.

DEFINITIONS

Chemical Definitions

Figure 1A:
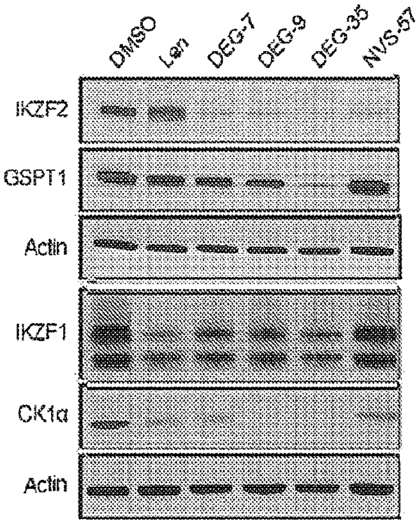
FIGS. 1A-C show western blots demonstrating the degradation of IKZF2 in MOLM13 cells by lead degrader compounds.
Figure 1B:
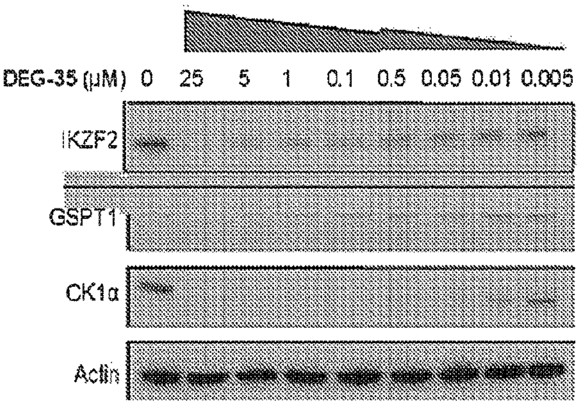
Figure 1C:
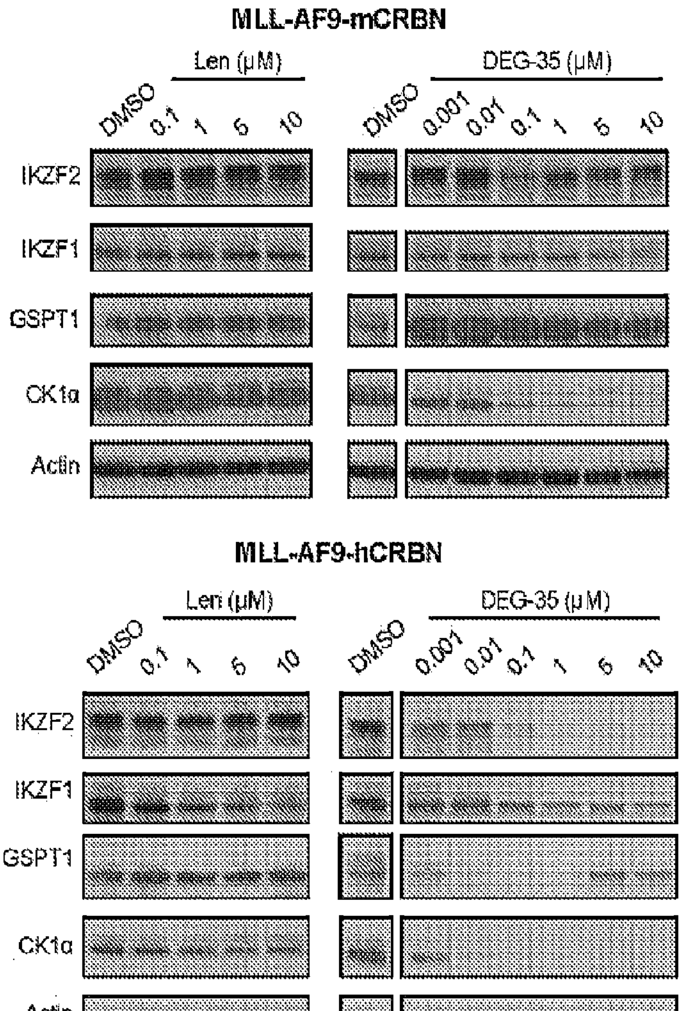

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; *Smith and March, March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *E. L. Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and $\overline{=\,=}$ or $\underline{=\,=}$ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $—CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $—CHF_2$, $—CH_2F$, $—CF_3$, $—CH_2CF_3$, $—CF_2CF_3$, $—CF_2CF_2CF_3$, $—CCl_3$, $—CFCl_2$, $—CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., $—CH═CHCH_3$ or

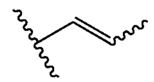)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-8}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3\_s}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $—SSR^{cc}$, $—C(═O)R^{aa}$, $—CO_2H$, —CHO, $—C(OR^{cc})_3$, $—CO_2R^{aa}$, $—OC(═O)R^{aa}$, $—OCO_2R^{aa}$, $—C(═O)N(R^{bb})_2$, $—OC(═O)N(R^{bb})_2$, $—NR^{bb}C(═O)R^{aa}$, $—NR^{bb}CO_2R^{aa}$, $—NR^{bb}C(═O)N(R^{bb})_2$, $—C(═NR^{bb})R^{aa}$, $—C(═NR^{bb})OR^{aa}$, $—OC(═NR^{bb})R^{aa}$, $—OC(═NR^{bb})OR^{aa}$, $—C(═NR^{bb})N(R^{bb})_2$, $—OC(═NR^{bb})N(R^{bb})_2$, $—NR^{bb}C(═NR^{bb})N(R^{bb})_2$, $—C(═O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(═O)R^{aa}$, $—OS(═O)R^{aa}$, $—Si(R^{aa})_3$, $—OSi(R^{aa})_3$—$C(═S)N(R^{bb})_2$, $—C(═O)SR^{aa}$, $—C(═S)SR^{aa}$, $—SC(═S)SR^{aa}$, $—SC(═O)SR^{aa}$, $—OC(═O)SR^{aa}$, $—SC(═O)OR^{aa}$, $—SC(═O)R^{aa}$, $—P(═O)(R^{aa})_2$, $—P(═O)(OR^{cc})_2$, $—OP(═O)(R^{aa})_2$, $—OP(═O)(OR^{cc})_2$, $—P(═O)(N(R^{bb})_2)_2$, $—OP(═O)(N(R^{bb})_2)_2$, $—NR^{bb}P(═O)(R^{aa})_2$, $—NR^{bb}P(═O)(OR^{cc})_2$, $—NR^{bb}P(═O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, $═NN(R^{bb})_2$, $═NNR^{bb}C(═O)R^{aa}$, $═NNR^{bb}C(═O)OR^{aa}$, $═NNR^{bb}S(═O)_2R^{aa}$, $═NR^{bb}$, or $═NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{cc})OR^{aa}$, $—C(═NR^{cc})N(R^{cc})_2$, $—SO_2N(R^{cc})_2$, $—SO_2R^{aa}$, $—SO_2OR^{cc}$, $—SOR^{aa}$, $—C(═S)N(R^{cc})_2$, $—C(═O)SR^{cc}$, $—C(═S)SR^{cc}$, $—P(═O)(R^{aa})_2$, $—P(═O)(OR^{cc})_2$, $—P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $—C(═O)R^{ee}$, $—CO_2H$, $—CO_2R^{ee}$, $—OC(═O)R^{ee}$, $—OCO_2R^{ee}$, $—C(═O)N(R^{ff})_2$, $—OC(═O)N(R^{ff})_2$, $—NR^{ff}C(═O)R^{ee}$, $—NR^{ff}CO_2R^{ee}$, $—NR^{ff}C(═O)N(R^{ff})_2$, $—C(═NR^{ff})OR^{ee}$, $—OC(═NR^{ff})R^{ee}$, $—OC(═NR^{ff})OR^{ee}$, $—C(═NR^{ff})N(R^{ff})_2$, $—OC(═NR^{ff})N(R^{ff})_2$, $—NR^{ff}C(═NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(═O)R^{ee}$, $—Si(R^{ee})_3$, $—OSi(R^{ee})_3$, $—C(═S)N(R^{ff})_2$, $—C(═O)SR^{ee}$, $—C(═S)SR^{ee}$, $—SC(═S)SR^{ee}$, $—P(═O)(OR^{ee})_2$, $—P(═O)(R^{ee})_2$, $—OP(═O)(R^{ee})_2$, $—OP(═O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_1$_6 perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-16}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl)+$X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(=NH)NH($C_{1-6}$ alkyl), —OC(=NH)$NH_2$, —NHC(=NH)N($C_{1-6}$ alkyl)$_2$, —NHC(=NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2$($C_{1-6}$ alkyl), —$SO_2O$($C_{1-6}$ alkyl), —$OSO_2$($C_{1-6}$ alkyl), —SO($C_{1-6}$ alkyl), —Si($C_1$-6 alkyl)$_3$, —OSi($C_{1-6}$ alkyl)$_3$ —C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_1$_6 perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{99}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3^+X^-$, —OP($OR^{cc}$)$_2$, —OP($OR^{cc}$)$_3^+X^-$, —OP(=O)($R^{aa}$)$_2$, —OP(=O)($OR^{cc}$)$_2$, and —OP(=O)(N($R^{bb}$)$_2$)$_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "acyl" refers to a group having the general formula —C(=O)$R^{X1}$, —C(=O)$OR^{X1}$, —C(=O)—O—C(=O)$R^{X1}$, —C(=O)$SR^{X1}$, —C(=O)N($R^{X1}$)$_2$, —C(=S)$R^{X1}$, —C(=S)N($R^{X1}$)$_2$, —C(=S)O($R^{X1}$), —C(=S)S($R^{X1}$), —C(=$NR^{X1}$)$R^{X1}$, —C(=$NR^{X1}$)$OR^{X1}$, —C(=$NR^{X1}$)$SR^{X1}$, and —C(=$NR^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (e.g., —C(═O)$R^{aa}$), carboxylic acids (e.g., —$CO_2$H), aldehydes (—CHO), esters (e.g., —$CO_2R^{aa}$, —C(═O)$SR^{aa}$, —C(═S)$SR^{aa}$), amides (e.g., —C(═O)N($R^{bb}$)$_2$, —C(═O)$NR^{bb}SO_2R^{aa}$, —C(═S)N($R^{bb}$)$_2$), and imines (e.g., —C(═$NR^{bb}$)$R^{aa}$, —C(═$NR^{bb}$)$OR^{aa}$), —C(═$NR^{bb}$)N($R^{bb}$)$_2$), wherein $R^{aa}$ and $R^{bb}$ are as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{ee}$, —C(═S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4 -methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R')_3$, $—P(R^{cc})_2$, $—P(R^{cc})_3{}^+X^-$, $—P(OR^c)_2$, $—P(OR^{cc})_3{}^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^a$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_42^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, -OMs), p-bromobenzenesulfonyloxy (brosylate, —OBs), $—OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., $—OC(=O)SR^{aa}$, $—OC(=O)R^{aa}$, $—OCO_2R^{aa}$, $—OC(=O)N(R^{bb})_2$, $—OC(=NR^{bb})R^{aa}$, $—OC(=NR^{bb})OR^{aa}$, $—OC(=NR^{bb})N(R^{bb})_2$, $—OS(=O)R^{aa}$, $—OSO_2R^{aa}$, $—OP(R^{cc})_2$, $—OP(R^{cc})_3$, $—OP(=O)_2R^{aa}$, $—OP(=O)(R^{aa})_2$, $—OP(=O)(OR^{cc})_2$, $—OP(=O)_2N(R^{bb})_2$, and $—OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions, such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates.

Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_7$-12 substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for promoting the degradation of IKZF2. In certain embodiments, a therapeutically effective amount is an amount sufficient for treating a cancer.

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease (e.g., cancer).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "hematological cancer" refers to cancer that begins in blood-forming tissue, such as the bone marrow, or in the cells of the immune system. Examples of hematologic cancer are leukemia, lymphoma, and multiple myeloma. Hematological cancer is also called blood cancer. Exemplary hematological cancers include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenstram's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term “leukemia” refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross’ leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling’s leukemia, stem cell leukemia, subleukemic leukemia, and undifferentiated cell leukemia.

The term “lymphoma” refers to a group of blood cancers that develop from lymphocytes. Lymphoma disease includes diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin’s lymphoma (HL), non-Hodgkin’s lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter’s transformation, nodal marginal zone lymphoma, or ALK-positive large B-cell lymphoma.

The terms “biologic,” “biologic drug,” and “biological product” refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term “small molecule” or “small molecule therapeutic” refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a “small organometallic molecule.” Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term “therapeutic agent” refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

DETAILED DESCRIPTION OF CERTAIN EMBODIMENTS

Provided herein are compounds that bind to and promote the degradation of IKZF2. In one aspect, the disclosure provides compounds of Formula (I), and pharmaceutically acceptable salts, solvates, hydrates, polymorphs, co-crystals, tautomers, stereoisomers, isotopically labeled derivatives, prodrugs, and pharmaceutical compositions thereof. The compounds are useful for the treatment of diseases associated with IKZF2 (e.g., a proliferative disease) in a subject in need thereof.

Compounds

In one aspect, disclosed is a compound of Formula (I):

(I)

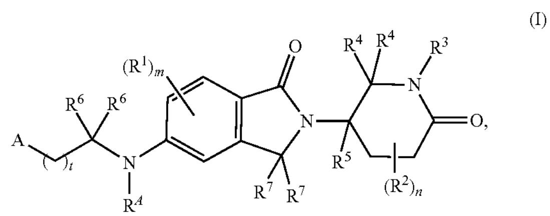

or a pharmaceutically acceptable salt, co-crystal, tautomer, stereoisomer, solvate, hydrate, polymorph, isotopically enriched derivative, or prodrug thereof, wherein:

A is substituted or unsubstituted aryl, or substituted or unsubstituted heteroaryl;

each $R^1$ is, independently, halogen, —$OR^A$, or substituted or unsubstituted $C_1$-$C_6$ alkyl;

each $R^2$ is, independently, halogen or $C_1$-$C_3$ alkyl;

$R^3$ is hydrogen or $C_1$-$C_3$ alkyl;

each $R^4$ is, independently, hydrogen or $C_1$-$C_3$ alkyl; or two $R^4$, together with the carbon atom to which they are attached, form a C═O, $C_3$-$C_6$ carbocycle, or a 4-6-membered heterocycle;

$R^5$ is hydrogen, halogen, or $C_1$-$C_3$ alkyl;

each $R^6$ is, independently, hydrogen, halogen, or $C_1$-$C_3$ alkyl; or two $R^6$, together with the carbon atom to which they are attached, form a C═O;

each $R^7$ is, independently, hydrogen or $C_1$-$C_3$ alkyl; or two $R^7$, together with the carbon atom to which they are attached, form a C═O;

each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom;

m is 0, 1, 2 or 3;

n is 0, 1, or 2; and t is 0 or 1;

provided that the compound is not of formula:

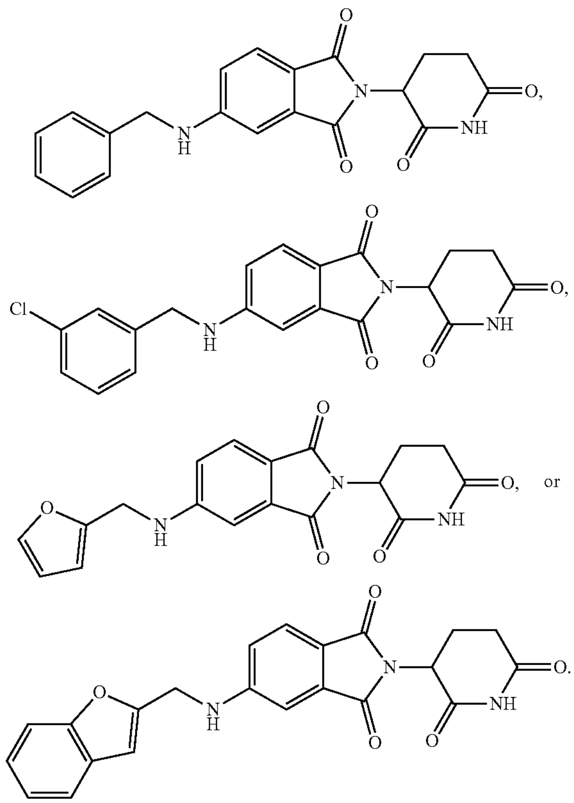

or $R^1$

As described herein, each $R^1$ is, independently, halogen, —$OR^A$, or substituted or unsubstituted $C_1$-$C_6$ alkyl. In certain embodiments, each $R^1$ is, independently, halogen or —$OR^A$. In certain embodiments, each $R^1$ is independently halogen, or substituted or unsubstituted $C_1$-$C_6$ alkyl. In certain embodiments, each $R^1$ is independently —$OR^A$, or substituted or unsubstituted $C_1$-$C_6$ alkyl. In certain embodiments, each $R^1$ is independently halogen, or unsubstituted $C_1$-$C_6$ alkyl. In certain embodiments, each $R^1$ is independently halogen, or unsubstituted $C_{1-4}$ alkyl. In certain embodiments, each $R^1$ is independently unsubstituted $C_{1-4}$ alkyl. In certain embodiments, each $R^1$ is, independently, halogen (e.g., —F, —Cl, —Br, or —I).

As described herein, m is 0, 1, 2 or 3. In certain embodiments, m is 0, 1, or 2. In certain embodiments, m is 0 or 1. In certain embodiments, m is 0. In certain embodiments, m is 1. In certain embodiments, m is 2. In certain embodiments, m is 3.

$R^2$

As described herein, each $R^2$ is, independently, halogen or $C_1$-$C_3$ alkyl. In certain embodiments, each $R^2$ is, independently, —F, —Cl, —Br, —I, or $C_1$-$C_3$ alkyl. In certain embodiments, each $R^2$ is, independently, halogen (e.g., —F, —Cl, —Br, or —I). In certain embodiments, each $R^2$ is independently $C_1$-$C_3$ alkyl. In certain embodiments, each $R^2$ is independently $C_1$-$C_2$ alkyl. In certain embodiments, each $R^2$ is independently $C_2$-$C_3$ alkyl. In certain embodiments, each $R^2$ is independently methyl. In certain embodiments, each $R^2$ is independently ethyl. In certain embodiments, each $R^2$ is independently propyl. In certain embodiments, each $R^2$ is independently isopropyl.

As described herein, n is 0, 1, or 2. In certain embodiments, n is 0 or 1. In certain embodiments, n is 0. In certain embodiments, n is 1. In certain embodiments, n is 2.

$R^3$

As described herein, $R^3$ is hydrogen or $C_1$-$C_3$ alkyl. In certain embodiments, $R^3$ is $C_1$-$C_3$ alkyl. In certain embodiments, $R^3$ is hydrogen.

$R^4$

As described herein, each $R^4$ is, independently, hydrogen or $C_1$-$C_3$ alkyl; or two $R^4$, together with the carbon atom to which they are attached, form a C═O, $C_3$-$C_6$ carbocycle, or a 4-6-membered heterocycle.

In certain embodiments, each $R^4$ is, independently, hydrogen or $C_1$-$C_3$ alkyl; or two $R^4$, together with the carbon atom to which they are attached, form a C═O. In certain embodiments, each $R^4$, together with the carbon atom to which they are attached, form a C═O.

In certain embodiments, each $R^4$, together with the carbon atom to which they are attached, form a $C_3$-$C_6$ carbocycle or a 4-6-membered heterocycle. In certain embodiments, each $R^4$, together with the carbon atom to which they are attached, form a $C_3$-$C_6$ carbocycle.

In certain embodiments, each $R^4$, together with the carbon atom to which they are attached, form a cyclopropyl. In certain embodiments, each $R^4$, together with the carbon atom to which they are attached, form a cyclobutyl. In certain embodiments, each $R^4$, together with the carbon atom to which they are attached, form a cyclopentyl. In certain embodiments, each $R^4$, together with the carbon atom to which they are attached, form a cyclohexyl. In certain embodiments, each $R^4$, together with the carbon atom to which they are attached, form a 4-6-membered heterocycle. In certain embodiments, each $R^4$, together with the carbon atom to which they are attached, form a 4-membered heterocycle (e.g., oxetane, azetidine). In certain embodiments, each $R^4$, together with the carbon atom to which they are attached, form a 5-membered heterocycle (e.g., pyrrolidine, tetrahydrofuran). In certain embodiments, each $R^4$, together with the carbon atom to which they are attached, form a 6-membered heterocycle (e.g., piperidine, tetrahydropyran).

$R^5$

As described herein, $R^5$ is hydrogen, halogen, or $C_1$-$C_3$ alkyl. In certain embodiments, $R^5$ is hydrogen or halogen. In certain embodiments, $R^5$ is halogen (e.g., —F, —Cl, —Br, or —I). In certain embodiments, $R^5$ is hydrogen or $C_1$-$C_3$ alkyl. In certain embodiments, $R^5$ is $C_1$-$C_3$ alkyl (e.g., methyl, ethyl, propyl, or isopropyl). In certain embodiments, $R^5$ is hydrogen. In certain embodiments, $R^5$ is deuterium.

$R^6$

As described herein, each $R^6$ is, independently, hydrogen, halogen, or $C_1$-$C_3$ alkyl; or two $R^6$, together with the carbon atom to which they are attached, form a C═O.

In certain embodiments, each $R^6$ is, independently, hydrogen or $C_1$-$C_3$ alkyl; or two $R^6$, together with the carbon atom to which they are attached, form a C═O. In certain embodiments, each $R^6$ is hydrogen; or two $R^6$, together with the carbon atom to which they are attached, form a C═O. In certain embodiments, each $R^6$ is hydrogen. In certain embodiments, each $R^6$ is fluorine. In certain embodiments, both $R^6$, together with the carbon atom to which they are attached, form a C═O.

t

In certain embodiments, t is 0 or 1. In certain embodiments, t is 0. In certain embodiments, t is 1.

$R^7$

As described herein, each $R^7$ is, independently, hydrogen or $C_1$-$C_3$ alkyl; or two $R^7$, together with the carbon atom to which they are attached, form a C═O. In certain embodiments, each $R^7$ is, independently, $C_1$-$C_3$ alkyl; or two $R^7$, together with the carbon atom to which they are attached, form a C═O. In certain embodiments, each $R^7$ is, independently, hydrogen; or two $R^7$, together with the carbon atom to which they are attached, form a C═O. In certain embodiments, two $R^7$, together with the carbon atom to which they are attached, form a C═O. In certain embodiments, each $R^7$ is hydrogen.

A

As described herein, A is substituted or unsubstituted aryl, or substituted or unsubstituted heteroaryl. In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran. In certain embodiments, A is substituted or unsubstituted naphthyl, or substituted or unsubstituted dibenzofuran.

In certain embodiments, A is substituted or unsubstituted quinoline, substituted or unsubstituted isoquinoline, substituted or unsubstituted naphthyl, or substituted or unsubstituted dibenzofuran. In certain embodiments, A is substituted or unsubstituted quinoline, or substituted or unsubstituted isoquinoline. In certain embodiments, A is substituted or unsubstituted naphthyl.

In certain embodiments, A is unsubstituted or substituted with halogen, amino, aryloxy, alkoxy, alkoxyalkyl, or hydroxyl. In certain embodiments, A is unsubstituted or substituted with alkoxy, alkoxyalkyl, or hydroxyl. In certain embodiments, A is unsubstituted or substituted with alkoxy or alkoxyalkyl. In certain embodiments, A is unsubstituted or substituted with $C_{1-4}$ alkoxy or $C_{1-4}$ alkoxyalkyl. In certain embodiments, A is unsubstituted or substituted with alkoxy. In certain embodiments, A is unsubstituted or substituted with $C_{1-4}$ alkoxy.

In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with halogen, amino, aryloxy, alkoxy, alkoxyalkyl, or hydroxyl.

In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with alkoxy, alkoxyalkyl, or hydroxyl.

In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with alkoxy or alkoxyalkyl. In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with $C_{1-4}$ alkoxy or $C_{1-4}$ alkoxyalkyl.

In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with alkoxy. In certain embodiments, A is substituted or unsubstituted phenyl, substituted or unsubstituted naphthyl, substituted or unsubstituted benzofuran, substituted or unsubstituted pyrene, substituted or unsubstituted quinoline, substituted or unsubstituted isoquinoline, or substituted or unsubstituted dibenzofuran, wherein A is unsubstituted or substituted with $C_{1-4}$ alkoxy.

In certain embodiments, A is substituted or unsubstituted naphthyl, or substituted or unsubstituted dibenzofuran, wherein A is unsubstituted or substituted with halogen, amino, aryloxy, alkoxy, alkoxyalkyl, or hydroxyl.

In certain embodiments, A is substituted or unsubstituted naphthyl, or substituted or unsubstituted dibenzofuran, wherein A is unsubstituted or substituted with alkoxy, alkoxyalkyl, or hydroxyl. In certain embodiments, A is substituted or unsubstituted naphthyl, or substituted or unsubstituted dibenzofuran, wherein A is unsubstituted or substituted with alkoxy or alkoxyalkyl. In certain embodiments, A is substituted or unsubstituted naphthyl, or substituted or unsubstituted dibenzofuran, wherein A is unsubstituted or substituted with $C_{1-4}$ alkoxy or $C_{1-4}$ alkoxyalkyl. In certain embodiments, A is substituted or unsubstituted naphthyl, or substituted or unsubstituted dibenzofuran, wherein A is unsubstituted or substituted with alkoxy. In certain embodiments, A is substituted or unsubstituted naphthyl, or substituted or unsubstituted dibenzofuran, wherein A is unsubstituted or substituted with $C_{1-4}$ alkoxy.

In certain embodiments, A is

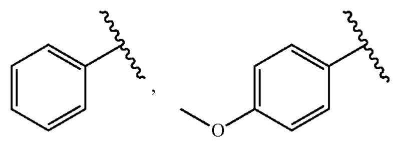

-continued
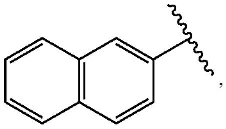, 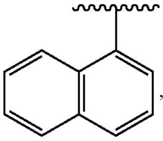, 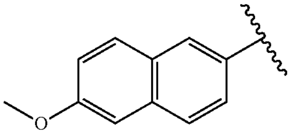, 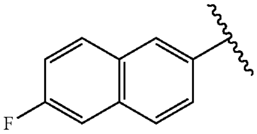, 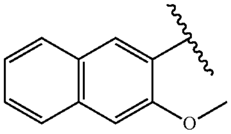, 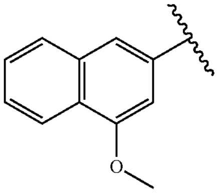, 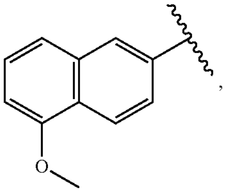, 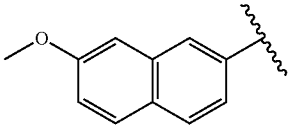, 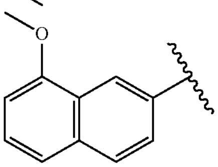, 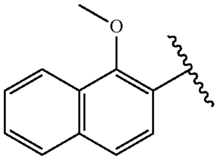, 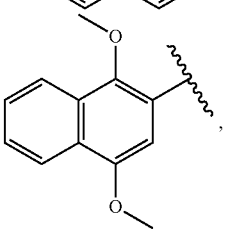, 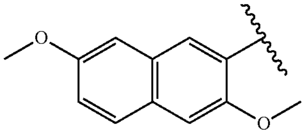, 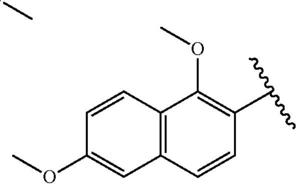, 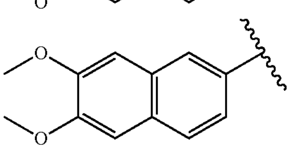, 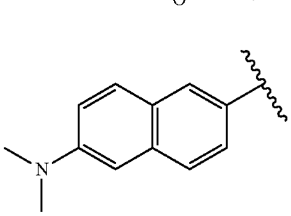, 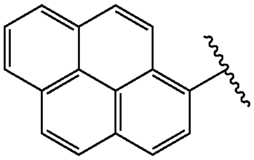, 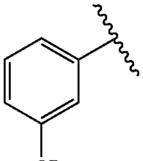, 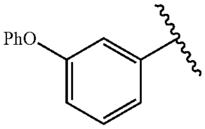,
-continued
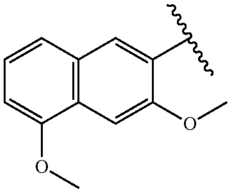, 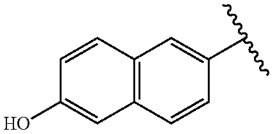, 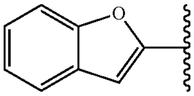, 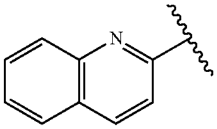, 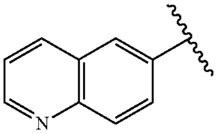, 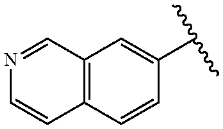, 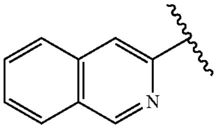, 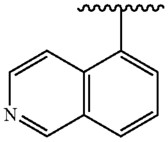, 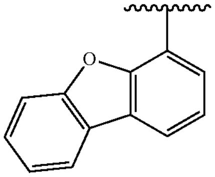, or 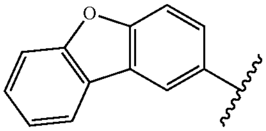.
In certain embodiments, A is
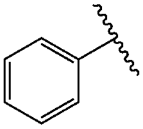, 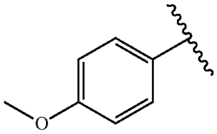, 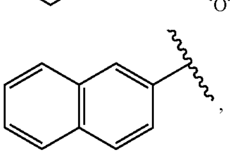, 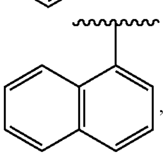, 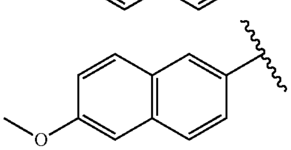, 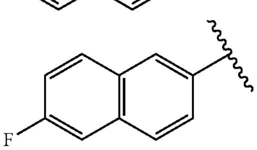, 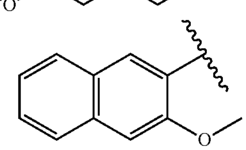, 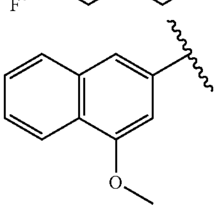, 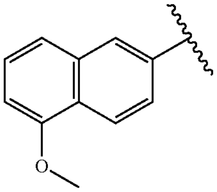, 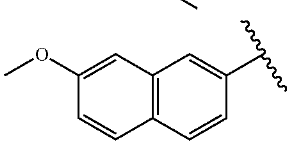, -continued
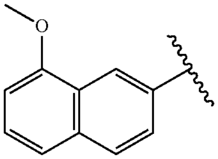,
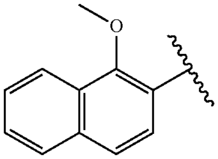,
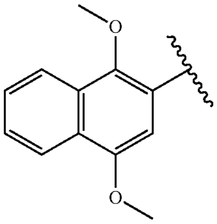,
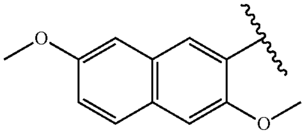,
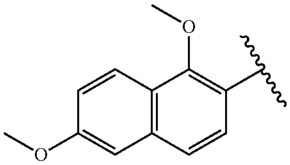,
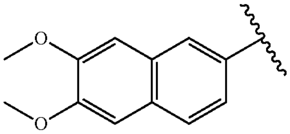,
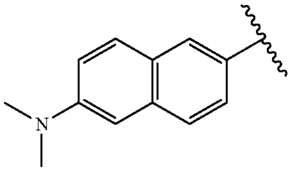,
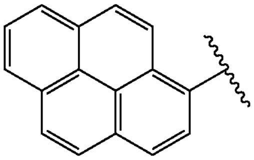,
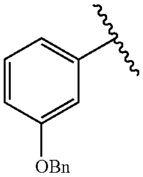,
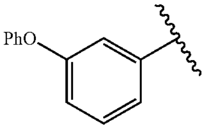,
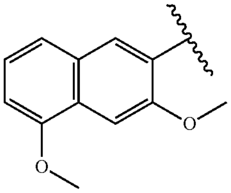,
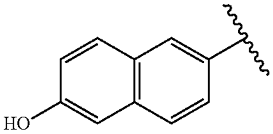,
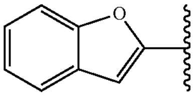,
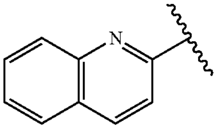,
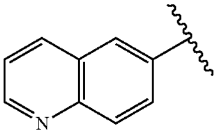,
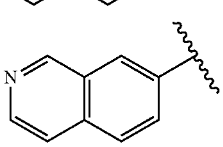,
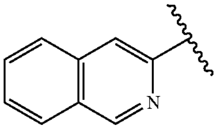,
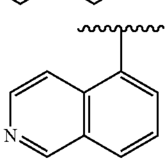,
-continued
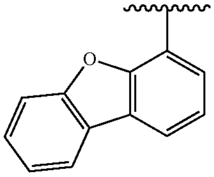,
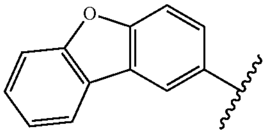,
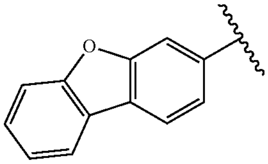,
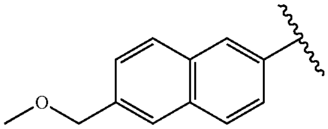,
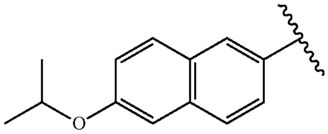,
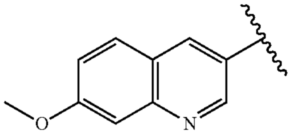,
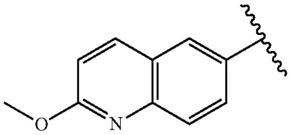,
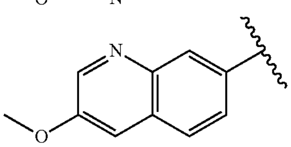,
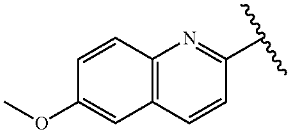,
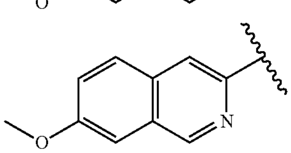,
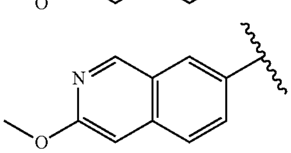,
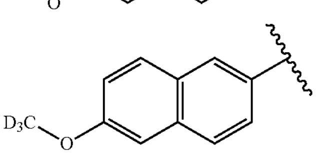,
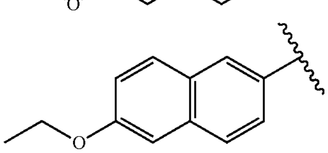, -continued

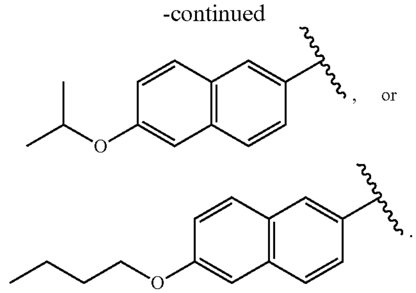

, or

.

In certain embodiments, A is

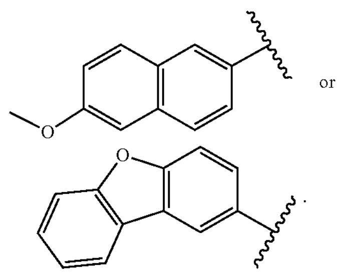

or

.

In certain embodiments, A is substituted or unsubstituted aryl. In certain embodiments, A is substituted or unsubstituted phenyl, substituted or unsubstituted naphthyl, or substituted or unsubstituted pyrene. In certain embodiments, A is substituted or unsubstituted naphthyl.

In certain embodiments, A is substituted or unsubstituted naphthyl, wherein A is unsubstituted or substituted with halogen, amino, aryloxy, alkoxy, alkoxyalkyl, or hydroxyl.

In certain embodiments, A is substituted or unsubstituted naphthyl, wherein A is unsubstituted or substituted with alkoxy, alkoxyalkyl, or hydroxyl.

In certain embodiments, A is substituted or unsubstituted naphthyl, wherein A is unsubstituted or substituted with alkoxy or alkoxyalkyl. In certain embodiments, A is substituted or unsubstituted naphthyl, wherein A is unsubstituted or substituted with $C_{1-4}$ alkoxy or $C_{1-4}$ alkoxyalkyl.

In certain embodiments, A is substituted or unsubstituted naphthyl, wherein A is unsubstituted or substituted with alkoxy. In certain embodiments, A is substituted or unsubstituted naphthyl, wherein A is unsubstituted or substituted with $C_{1-4}$ alkoxy.

In certain embodiments, A is naphthyl substituted with halogen, amino, aryloxy, alkoxy, alkoxyalkyl, or hydroxyl.

In certain embodiments, A is naphthyl substituted with alkoxy, alkoxyalkyl, or hydroxyl.

In certain embodiments, A is naphthyl substituted with alkoxy or alkoxyalkyl. In certain embodiments, A is naphthyl substituted with $C_{1-4}$ alkoxy or $C_{1-4}$ alkoxyalkyl.

In certain embodiments, A is naphthyl substituted with alkoxy. In certain embodiments, A is naphthyl substituted with $C_{1-4}$ alkoxy.

In certain embodiments, A is

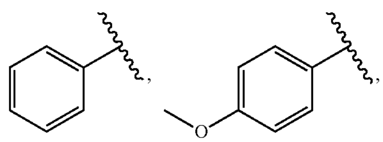

,

,

-continued

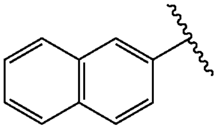, 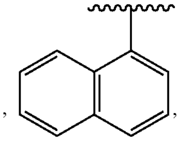,

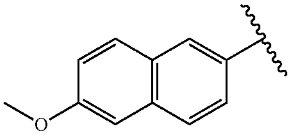, 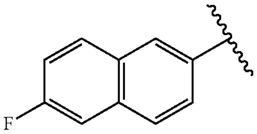,

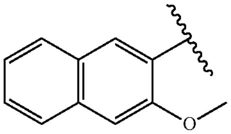, 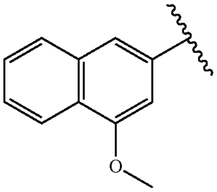,

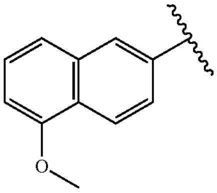, 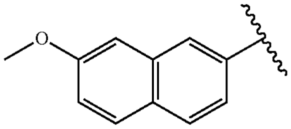,

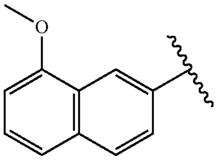, 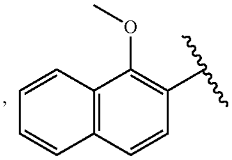,

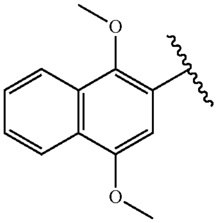, 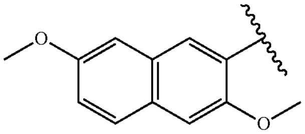,

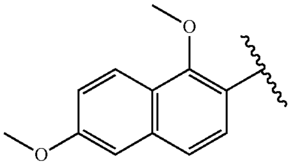,

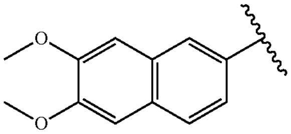,

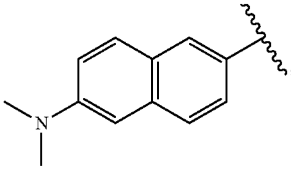, 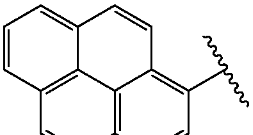,

-continued
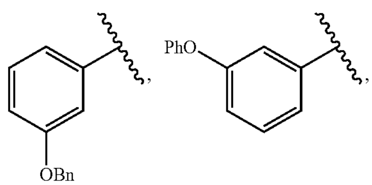
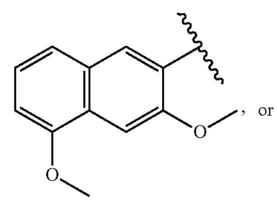
or
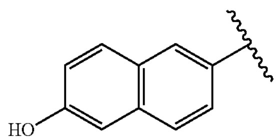
In certain embodiments, A is
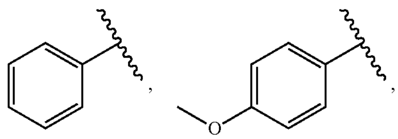
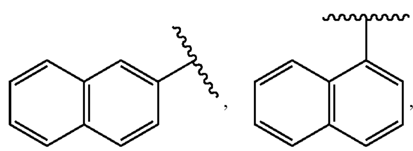
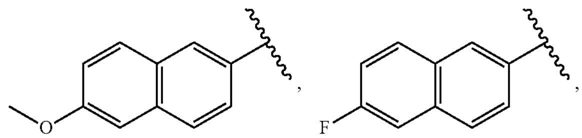
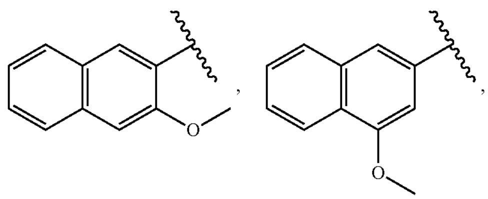
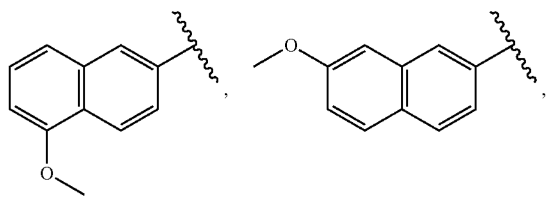
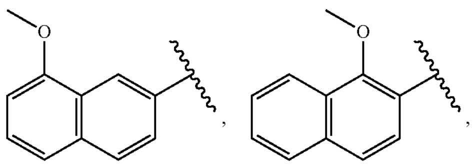
-continued
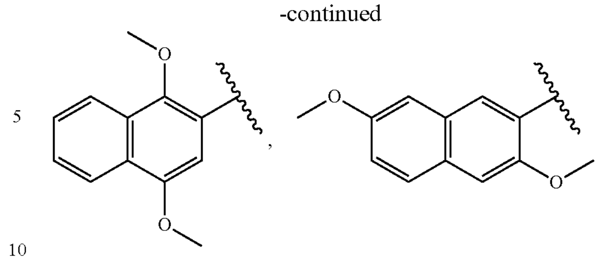
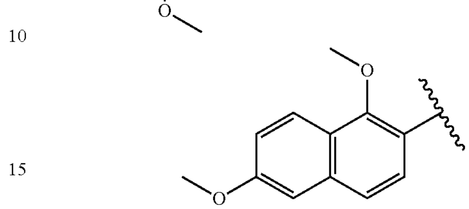
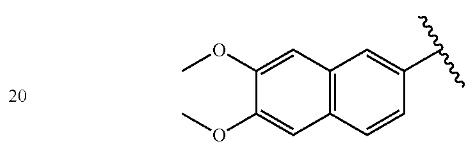
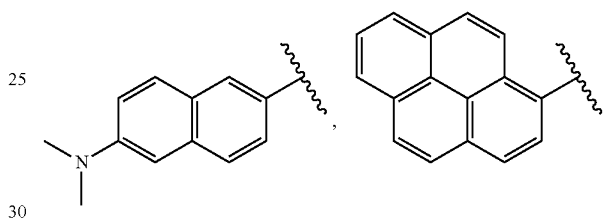
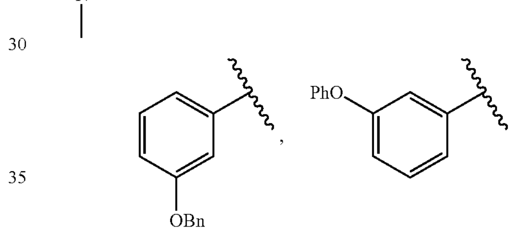
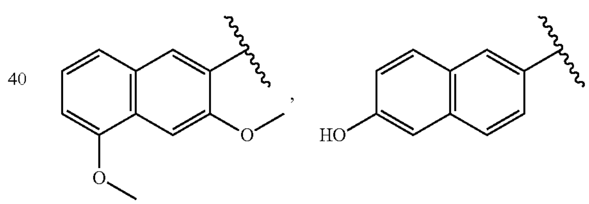
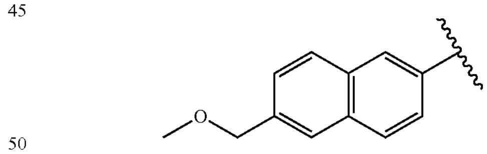
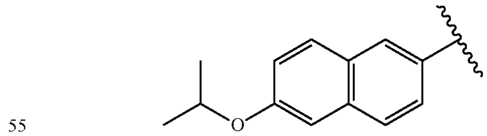
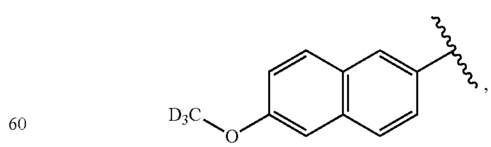
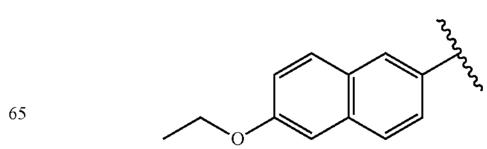

-continued

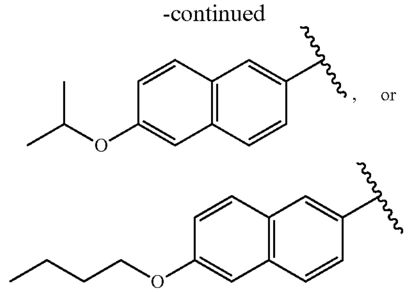

, or

.

In certain embodiments, A is

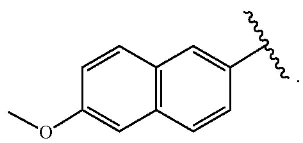 [SMILES: *c1ccc2cc(OC)ccc2c1]

.

In certain embodiments, A is substituted or unsubstituted heteroaryl. In certain embodiments, A is substituted or unsubstituted benzofuran, substituted or unsubstituted quinoline, substituted or unsubstituted isoquinoline, or substituted or unsubstituted dibenzofuran. In certain embodiments, A is substituted or unsubstituted dibenzofuran.

In certain embodiments, A is unsubstituted dibenzofuran.

In certain embodiments, A is substituted or unsubstituted quinoline, or substituted or unsubstituted isoquinoline, wherein A is unsubstituted or substituted with halogen, amino, aryloxy, alkoxy, alkoxyalkyl, or hydroxyl.

In certain embodiments, A is substituted or unsubstituted quinoline, or substituted or unsubstituted isoquinoline, wherein A is unsubstituted or substituted with alkoxy, alkoxyalkyl, or hydroxyl.

In certain embodiments, A is substituted or unsubstituted quinoline, or substituted or unsubstituted isoquinoline, wherein A is unsubstituted or substituted with alkoxy or alkoxyalkyl. In certain embodiments, A is substituted or unsubstituted quinoline, or substituted or unsubstituted isoquinoline, wherein A is unsubstituted or substituted with $C_{1-4}$ alkoxy or $C_{1-4}$ alkoxyalkyl.

In certain embodiments, A is substituted or unsubstituted quinoline, or substituted or unsubstituted isoquinoline, wherein A is unsubstituted or substituted with alkoxy. In certain embodiments, A is substituted or unsubstituted quinoline, or substituted or unsubstituted isoquinoline, wherein A is unsubstituted or substituted with $C_{1-4}$ alkoxy.

In certain embodiments, A is

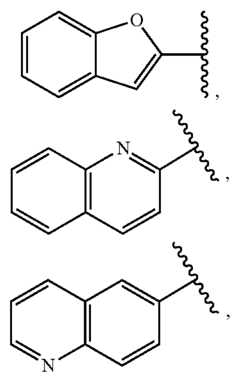

,

,

,

-continued

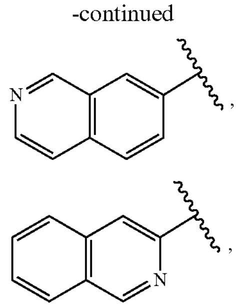

,

,

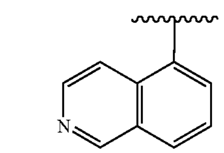

, or

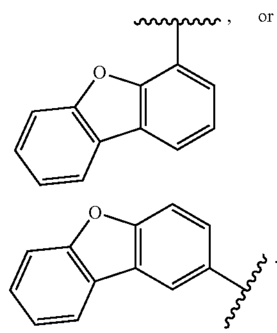

.

In certain embodiments, A is

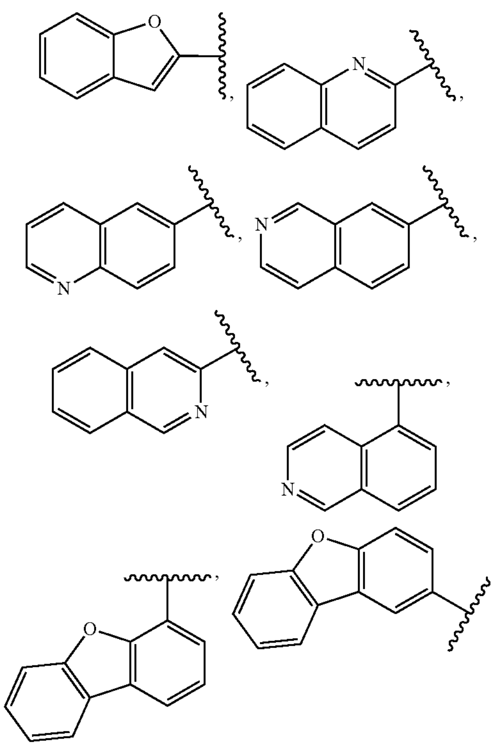

, , , , , , ,

-continued

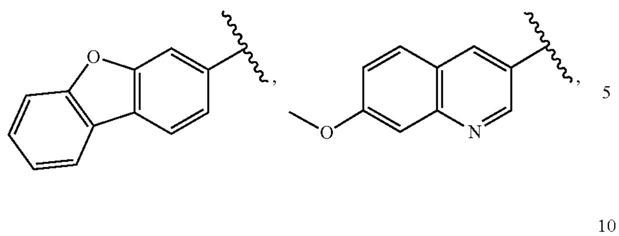

,

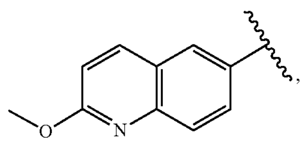

,

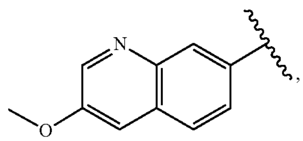

,

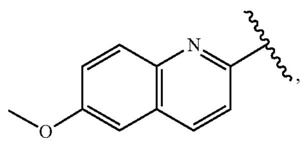

,

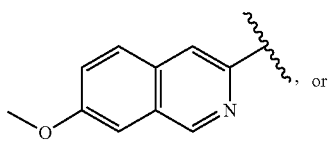

, or

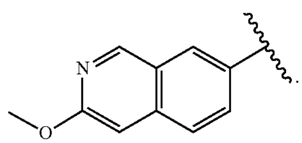

.

In certain embodiments, A is

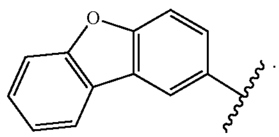 [SMILES: *c1ccc2oc3ccccc3c2c1]

.

$R^A$

As described herein, each occurrence of $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom.

In certain embodiments, each occurrence of $R^A$ is, independently, hydrogen, or substituted or unsubstituted alkyl. In certain embodiments, each occurrence of $R^A$ is, independently, hydrogen or unsubstituted alkyl. In certain embodiments, each occurrence of $R^A$ is hydrogen.

Further Embodiments of Formula (I)

In certain embodiments, the compound of Formula (I) is a compound of Formula (I-a):

(I-a)

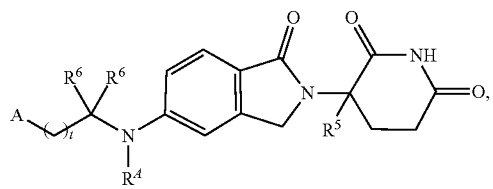

or a pharmaceutically acceptable salt, co-crystal, tautomer, stereoisomer, solvate, hydrate, polymorph, isotopically enriched derivative, or prodrug thereof, wherein A, $R^A$, $R^5$, $R^6$, and t are as defined herein.

In certain embodiments, the compound of Formula (I) is a compound of Formula (I-b):

(I-b)

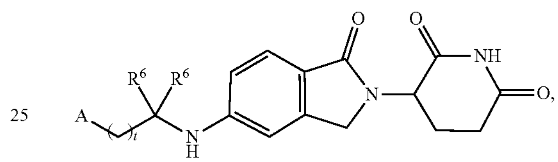

or a pharmaceutically acceptable salt, co-crystal, tautomer, stereoisomer, solvate, hydrate, polymorph, isotopically enriched derivative, or prodrug thereof, wherein A, $R^6$, and t are as defined herein.

In certain embodiments, the compound of Formula (I) is a compound of Formula (I-c), (I-c)

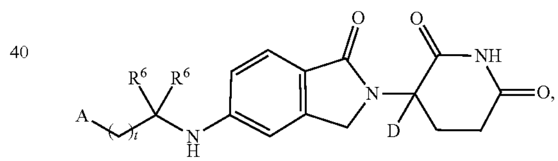

or a pharmaceutically acceptable salt, co-crystal, tautomer, stereoisomer, solvate, hydrate, polymorph, isotopically enriched derivative, or prodrug thereof, wherein A, $R^6$, and t are as defined herein.

In certain embodiments, the compound of Formula (I) is a compound of Formula (I-d):

(I-d)

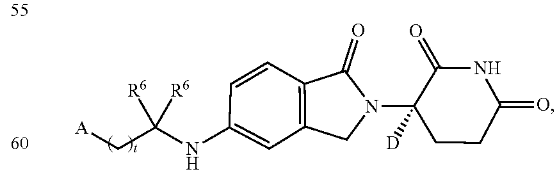

or a pharmaceutically acceptable salt, co-crystal, tautomer, stereoisomer, solvate, hydrate, polymorph, isotopically enriched derivative, or prodrug thereof, wherein A, $R^6$, and t are as defined herein.

In certain embodiments, the compound of Formula (I) is a compound of Formula (I-e):

(I-e)

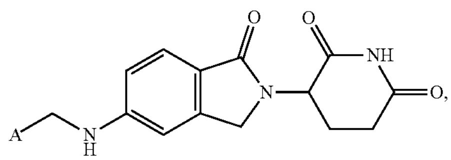

or a pharmaceutically acceptable salt, co-crystal, tautomer, stereoisomer, solvate, hydrate, polymorph, isotopically enriched derivative, or prodrug thereof, wherein A is as defined herein.

In certain embodiments, the compound of Formula (I) is a compound of Formula (I-f):

(I-f)

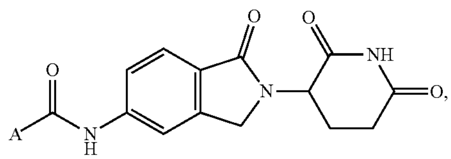

or a pharmaceutically acceptable salt, co-crystal, tautomer, stereoisomer, solvate, hydrate, polymorph, isotopically enriched derivative, or prodrug thereof, wherein A is as defined herein.

In certain embodiments, the compound of Formula (I) is a compound of Formula (I-g):

(I-g)

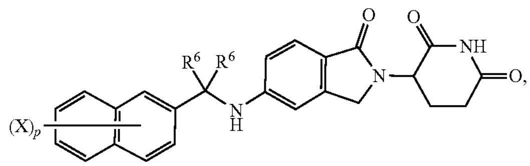

or a pharmaceutically acceptable salt, co-crystal, tautomer, stereoisomer, solvate, hydrate, polymorph, isotopically enriched derivative, or prodrug thereof, wherein each X is, independently, halogen, —$OR^A$, or —$N(R^A)_2$; p is 0, 1, or 2; and $R^6$ is as defined herein.

In certain embodiments of the compound of Formula (I-g), X is halogen. In certain embodiments of the compound of Formula (I-g), X is —$OR^A$. In certain embodiments of the compound of Formula (I-g), X is —$N(R^A)_2$. In certain embodiments of the compound of Formula (I-g), $R^A$ is hydrogen or $C_{1-3}$ alkyl. In certain embodiments of the compound of Formula (I-g), $R^A$ is hydrogen or $C_{1-4}$ alkyl. In certain embodiments of the compound of Formula (I-g), $R^A$ is $C_{1-3}$ alkyl. In certain embodiments of the compound of Formula (I-g), $R^A$ is $C_{1-4}$ alkyl. In certain embodiments of the compound of Formula (I-g), $R^A$ is methyl. In certain embodiments of the compound of Formula (I-g), X is —$OCH_3$. In certain embodiments of the compound of Formula (I-g), X is —F. In certain embodiments of the compound of Formula (I-g), X is —$N(CH_3)_2$. In certain embodiments of the compound of Formula (I-g), X is —OH. In certain embodiments of the compound of Formula (I-g), X is —$OCH(CH_3)_2$. In certain embodiments of the compound of Formula (I-g), X is —$OCD_3$. In certain embodiments of the compound of Formula (I-g), X is —$OCH_2CH_3$. In certain embodiments of the compound of Formula (I-g), X is —$OCH_2CH_2CH_2CH_3$.

In certain embodiments, the compound of Formula (I) is a compound of Formula (I-h):

(I-h)

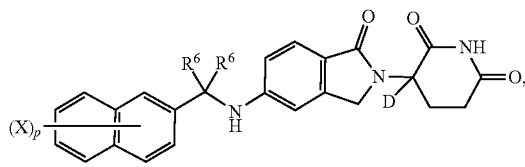

or a pharmaceutically acceptable salt, co-crystal, tautomer, stereoisomer, solvate, hydrate, polymorph, isotopically enriched derivative, or prodrug thereof, wherein each X is, independently, halogen, —$OR^A$, or —$N(R^A)_2$; p is 0, 1, or 2; and $R^6$ is as defined herein.

In certain embodiments of the compound of Formula (I-h), X is halogen. In certain embodiments of the compound of Formula (I-h), X is —$OR^A$. In certain embodiments of the compound of Formula (I-h), X is —$N(R^A)_2$. In certain embodiments of the compound of Formula (I-h), $R^A$ is hydrogen or $C_{1-3}$ alkyl. In certain embodiments of the compound of Formula (I-h), $R^A$ is hydrogen or $C_{1-4}$ alkyl. In certain embodiments of the compound of Formula (I-h), $R^A$ is $C_{1-3}$ alkyl. In certain embodiments of the compound of Formula (I-h), $R^A$ is $C_{1-4}$ alkyl. In certain embodiments of the compound of Formula (I-h), $R^A$ is methyl. In certain embodiments of the compound of Formula (I-h), X is —$OCH_3$. In certain embodiments of the compound of Formula (I-h), X is —F. In certain embodiments of the compound of Formula (I-h), X is —$N(CH_3)_2$. In certain embodiments of the compound of Formula (I-h), X is —OH. In certain embodiments of the compound of Formula (I-h), X is —$OCH(CH_3)_2$. In certain embodiments of the compound of Formula (I-h), X is —$OCD_3$. In certain embodiments of the compound of Formula (I-h), X is —$OCH_2CH_3$. In certain embodiments of the compound of Formula (I-h), X is —$OCH_2CH_2CH_2CH_3$.

In certain embodiments, the compound of Formula (I) is a compound of Formula (I-i):

(I-i)

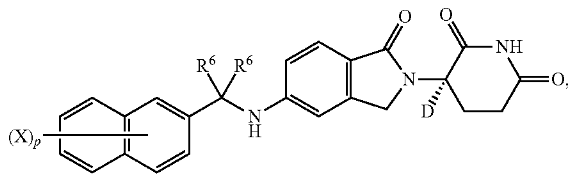

or a pharmaceutically acceptable salt, co-crystal, tautomer, stereoisomer, solvate, hydrate, polymorph, isotopically enriched derivative, or prodrug thereof, wherein each X is, independently, halogen, —$OR^A$, or —$N(R^A)_2$; p is 0, 1, or 2; and $R^6$ is as defined herein.

In certain embodiments of the compound of Formula (I-i), X is halogen. In certain embodiments of the compound of Formula (I-i), X is —$OR^A$. In certain embodiments of the compound of Formula (I-i), X is —$N(R^A)_2$. In certain embodiments of the compound of Formula (I-i), $R^A$ is hydrogen or $C_{1-3}$ alkyl. In certain embodiments of the compound of Formula (I-i), $R^A$ is hydrogen or $C_{1-4}$ alkyl. In certain embodiments of the compound of Formula (I-i), $R^A$ is $C_{1-3}$ alkyl. In certain embodiments of the compound of Formula (I-i), $R^A$ is $C_{1-4}$ alkyl. In certain embodiments of the compound of Formula (I-i), $R^A$ is methyl. In certain embodiments of the compound of Formula (I-i), X is —$OCH_3$. In certain embodiments of the compound of Formula (I-i), X is —F. In certain embodiments of the compound of Formula (I-i), X is —$N(CH_3)_2$. In certain embodiments of the compound of Formula (I-i), X is —OH. In certain embodiments of the compound of Formula (I-i), X is —$OCH(CH_3)_2$. In certain embodiments of the compound of Formula (I-i), X is —$OCD_3$. In certain embodiments of the compound of Formula (I-i), X is —$OCH_2CH_3$. In certain embodiments of the compound of Formula (I-i), X is —$OCH_2CH_2CH_2CH_3$.

In certain embodiments, the compound of Formula (I) is a compound of Formula (I-j):

(I-j)

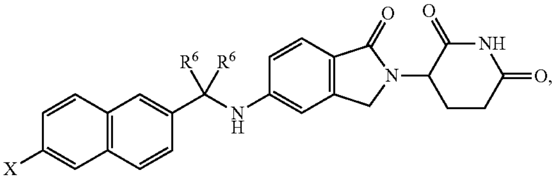

or a pharmaceutically acceptable salt, co-crystal, tautomer, stereoisomer, solvate, hydrate, polymorph, isotopically enriched derivative, or prodrug thereof, wherein X is halogen, —$OR^A$, or —$N(R^A)_2$; p is 0, 1, or 2; and $R^6$ is as defined herein.

In certain embodiments of the compound of Formula (I-j), X is halogen. In certain embodiments of the compound of Formula (I-j), X is —$OR^A$. In certain embodiments of the compound of Formula (I-j), X is —$N(R^A)_2$. In certain embodiments of the compound of Formula (I-j), $R^A$ is hydrogen or $C_{1-3}$ alkyl. In certain embodiments of the compound of Formula (I-j), $R^A$ is hydrogen or $C_{1-4}$ alkyl. In certain embodiments of the compound of Formula (I-j), $R^A$ is $C_{1-3}$ alkyl. In certain embodiments of the compound of Formula (I-j), $R^A$ is $C_{1-4}$ alkyl. In certain embodiments of the compound of Formula (I-j), $R^A$ is methyl. In certain embodiments of the compound of Formula (I-j), X is —$OCH_3$. In certain embodiments of the compound of Formula (I-j), X is —F. In certain embodiments of the compound of Formula (I-j), X is —$N(CH_3)_2$. In certain embodiments of the compound of Formula (I-j), X is —OH. In certain embodiments of the compound of Formula (I-j), X is —$OCH(CH_3)_2$. In certain embodiments of the compound of Formula (I-j), X is —$OCD_3$. In certain embodiments of the compound of Formula (I-j), X is —$OCH_2CH_3$. In certain embodiments of the compound of Formula (I-j), X is —$OCH_2CH_2CH_2CH_3$.

In certain embodiments, the compound of Formula (I) is a compound of Formula (I-k):

(I-k)

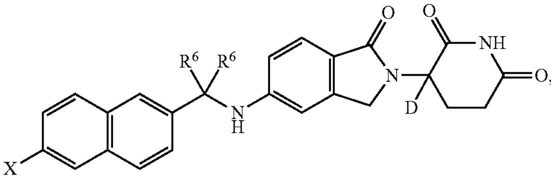

or a pharmaceutically acceptable salt, co-crystal, tautomer, stereoisomer, solvate, hydrate, polymorph, isotopically enriched derivative, or prodrug thereof, wherein X is halogen, —$OR^A$, or —$N(R^A)_2$; p is 0, 1, or 2; and $R^6$ is as defined herein.

In certain embodiments of the compound of Formula (I-k), X is halogen. In certain embodiments of the compound of Formula (I-k), X is —$OR^A$. In certain embodiments of the compound of Formula (I-k), X is —$N(R^A)_2$. In certain embodiments of the compound of Formula (I-k), $R^A$ is hydrogen or $C_{1-3}$ alkyl. In certain embodiments of the compound of Formula (I-k), $R^A$ is hydrogen or $C_{1-4}$ alkyl. In certain embodiments of the compound of Formula (I-k), $R^A$ is $C_{1-3}$ alkyl. In certain embodiments of the compound of Formula (I-k), $R^A$ is $C_{1-4}$ alkyl. In certain embodiments of the compound of Formula (I-k), $R^A$ is methyl. In certain embodiments of the compound of Formula (I-k), X is —$OCH_3$. In certain embodiments of the compound of Formula (I-k), X is —F. In certain embodiments of the compound of Formula (I-k), X is —$N(CH_3)_2$. In certain embodiments of the compound of Formula (I-k), X is —OH. In certain embodiments of the compound of Formula (I-k), X is —$OCH(CH_3)_2$. In certain embodiments of the compound of Formula (I-k), X is —$OCD_3$. In certain embodiments of the compound of Formula (I-k), X is —$OCH_2CH_3$. In certain embodiments of the compound of Formula (I-k), X is —$OCH_2CH_2CH_2CH_3$.

In certain embodiments, the compound of Formula (I) is a compound of Formula (I-l):

(I-l)

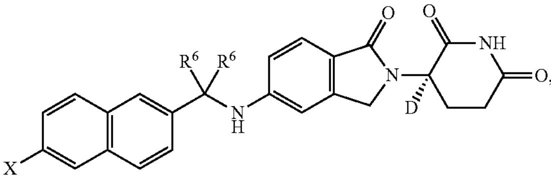

or a pharmaceutically acceptable salt, co-crystal, tautomer, stereoisomer, solvate, hydrate, polymorph, isotopically enriched derivative, or prodrug thereof, wherein X is halogen, —$OR^A$, or —$N(R^A)_2$; p is 0, 1, or 2; and $R^6$ is as defined herein.

In certain embodiments of the compound of Formula (I-l), X is halogen. In certain embodiments of the compound of Formula (I-l), X is —$OR^A$. In certain embodiments of the compound of Formula (I-l), X is —$N(R^A)_2$. In certain embodiments of the compound of Formula (I-l), $R^A$ is hydrogen or $C_{1-3}$ alkyl. In certain embodiments of the compound of Formula (I-l), $R^A$ is hydrogen or $C_{1-4}$ alkyl. In certain embodiments of the compound of Formula (I-l), $R^A$ is $C_{1-3}$ alkyl. In certain embodiments of the compound of Formula (I-l), $R^A$ is $C_{1-4}$ alkyl. In certain embodiments of the compound of Formula (I-l), $R^A$ is methyl. In certain embodiments of the compound of Formula (I-l), X is —$OCH_3$. In certain embodiments of the compound of Formula (I-l), X is —F. In certain embodiments of the compound of Formula (I-l), X is —$N(CH_3)_2$. In certain embodiments of the compound of Formula (I-l), X is —OH. In certain embodiments of the compound of Formula (I-l), X is —$OCH(CH_3)_2$. In certain embodiments of the compound of Formula (I-l), X is —$OCD_3$. In certain embodiments of the compound of Formula (I-l), X is —$OCH_2CH_3$. In certain embodiments of the compound of Formula (I-l), X is —$OCH_2CH_2CH_2CH_3$.

In certain embodiments, the compound of Formula (I) is a compound of the formula:

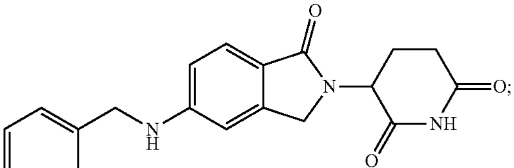

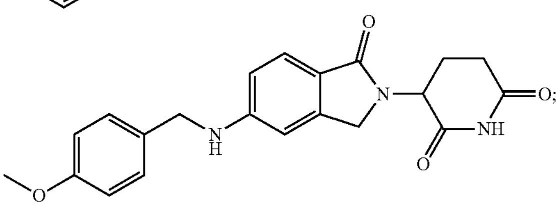

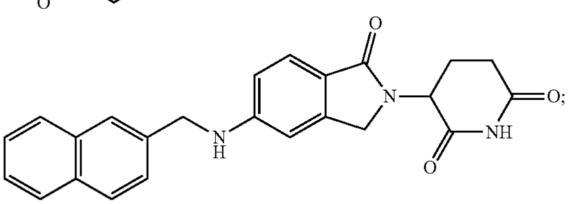

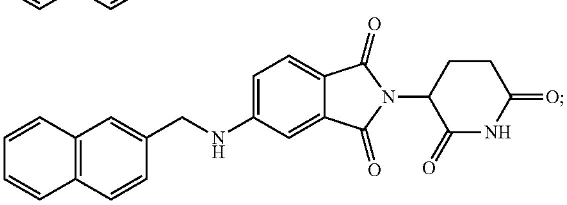

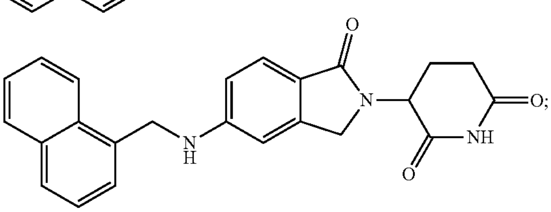

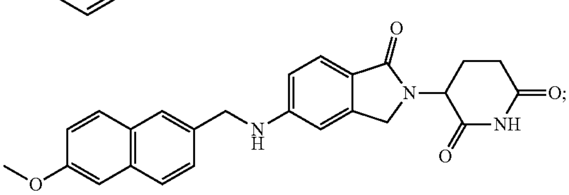

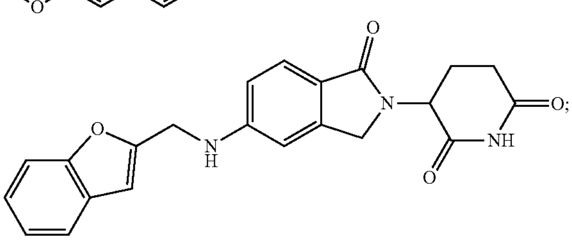

-continued

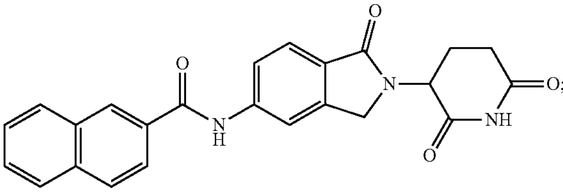

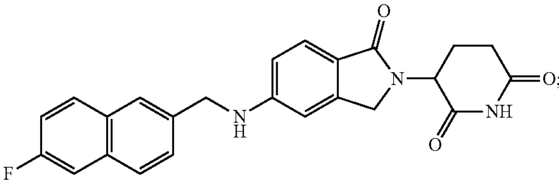

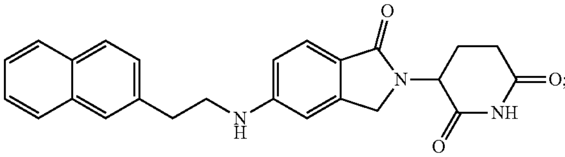

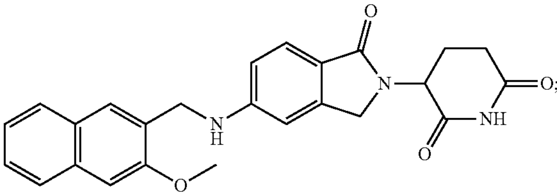

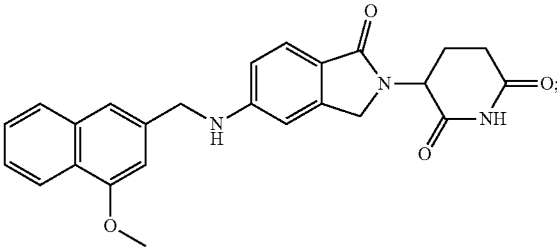

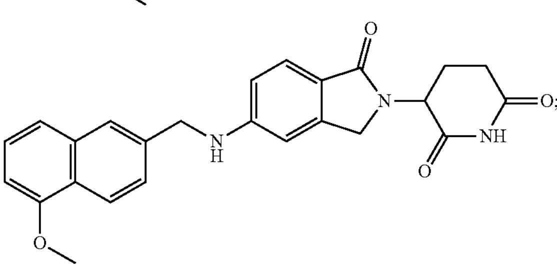

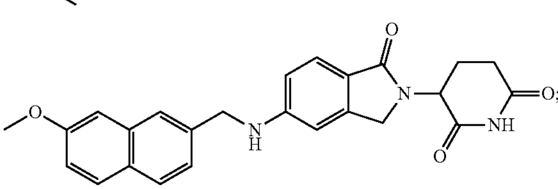

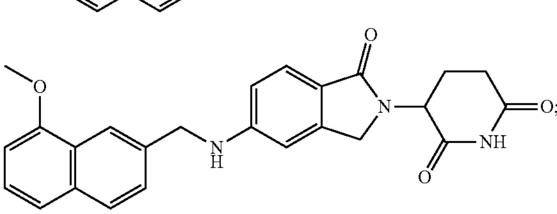

-continued
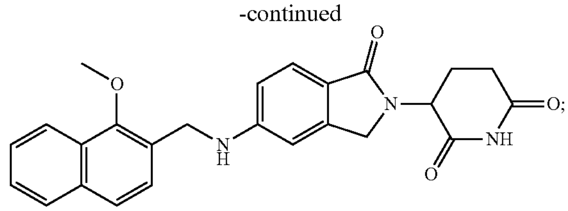
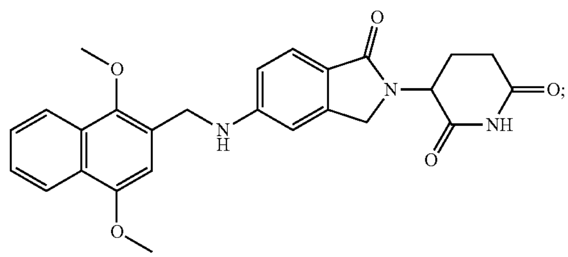
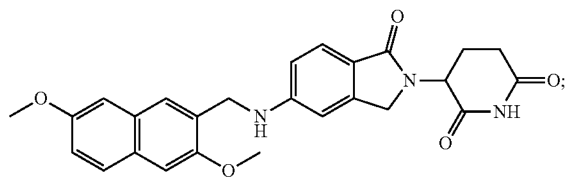
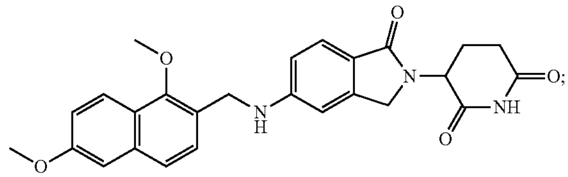
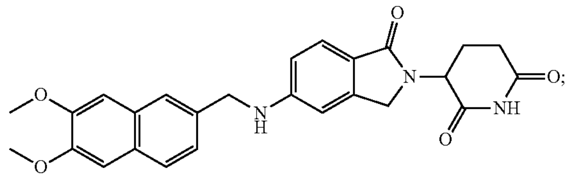
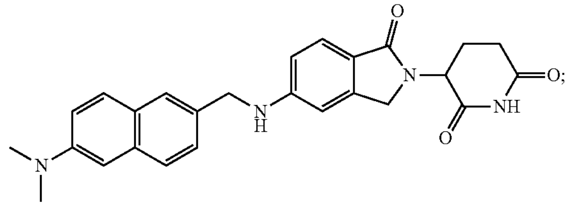
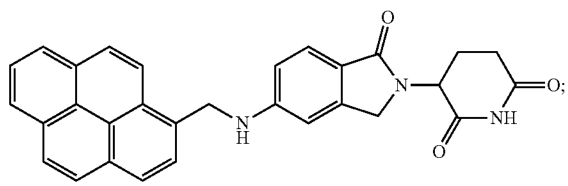
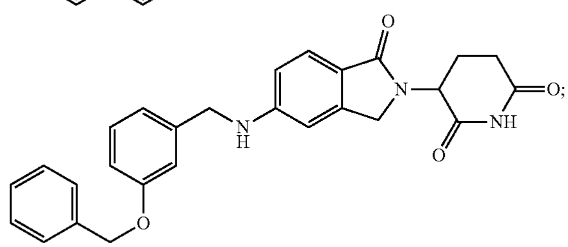
-continued
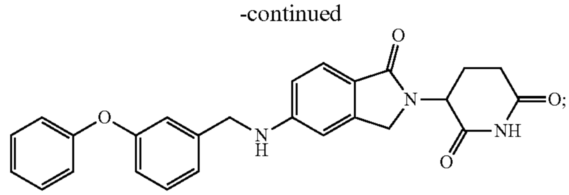
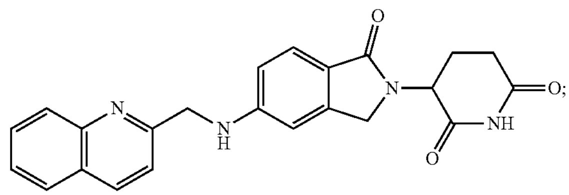
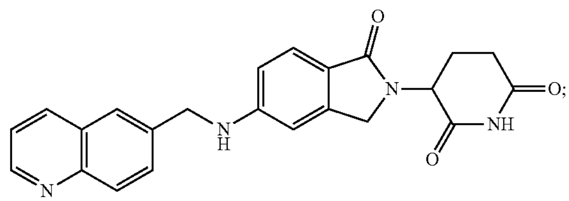
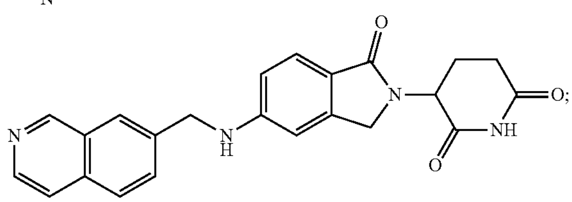
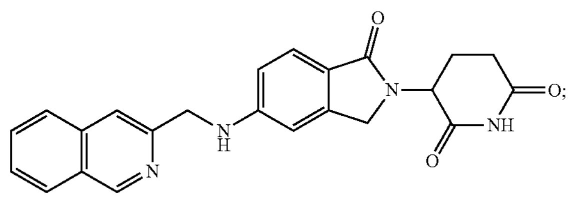
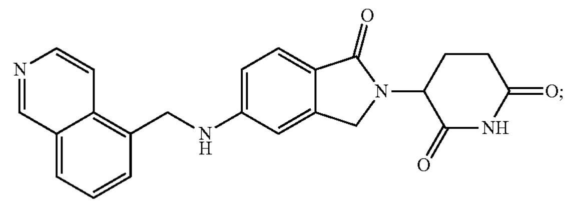
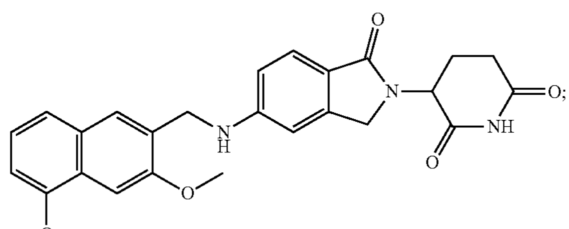
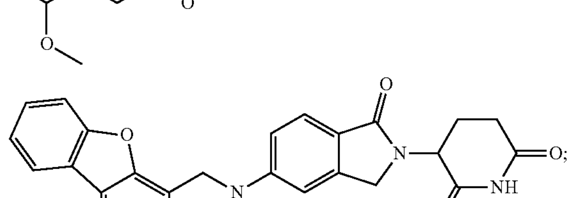
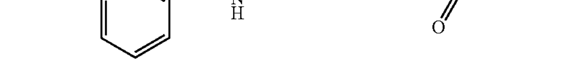

-continued
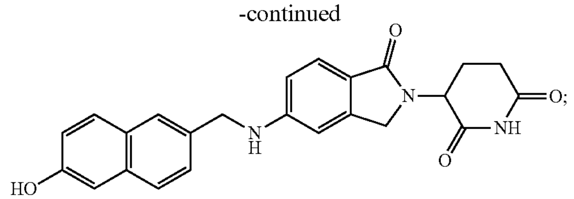
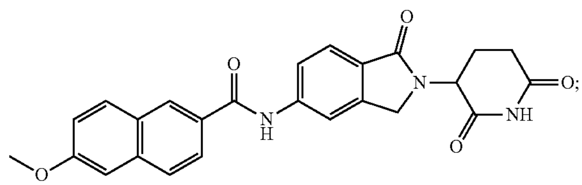
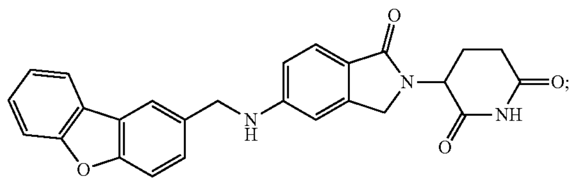
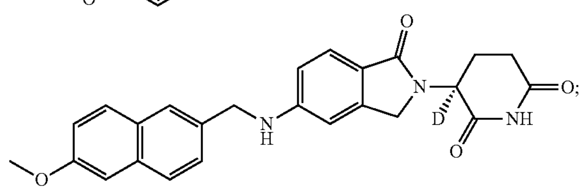
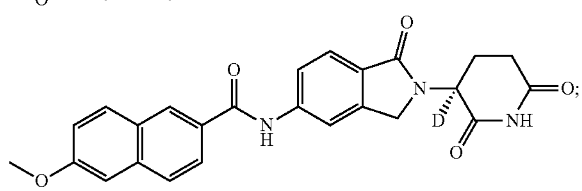
or a pharmaceutically acceptable salt, co-crystal, tautomer, stereoisomer, solvate, hydrate, polymorph, isotopically enriched derivative, or prodrug thereof.
In certain embodiments, the compound of Formula (I) is a compound of the formula:
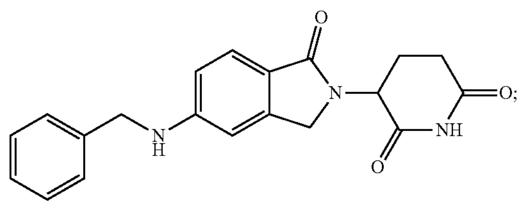
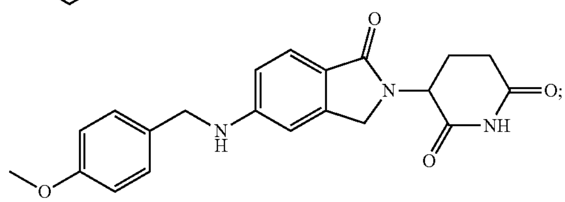
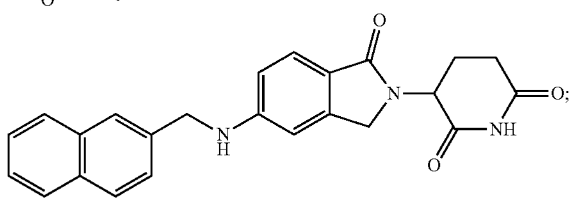
-continued
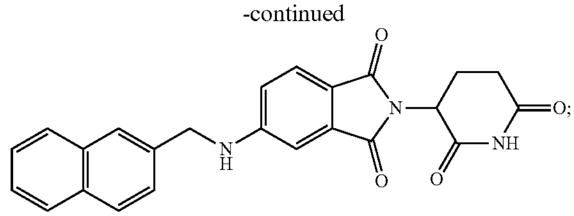
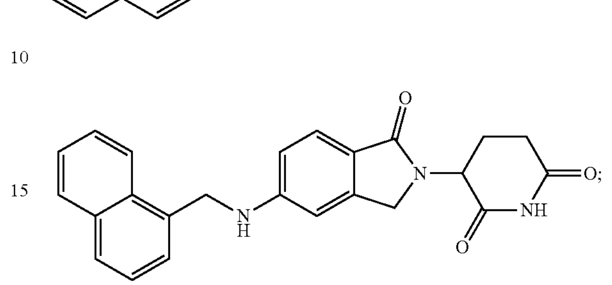
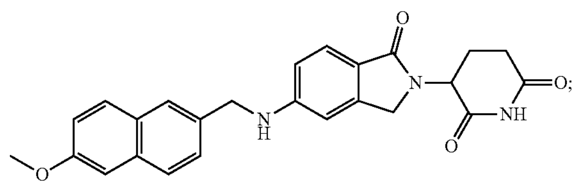
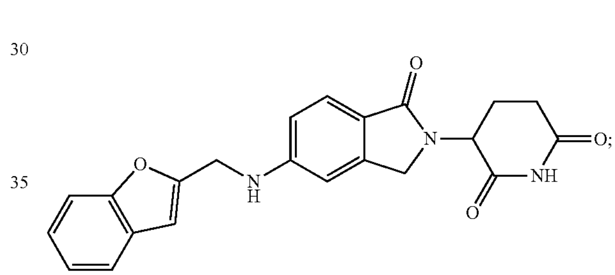
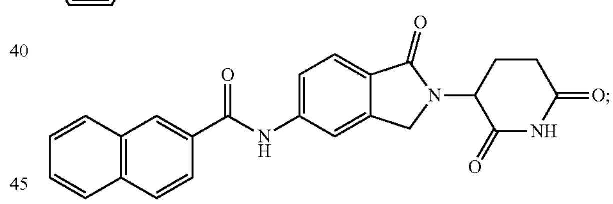
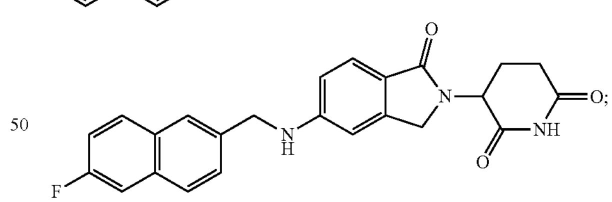
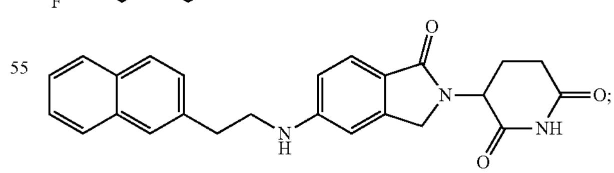
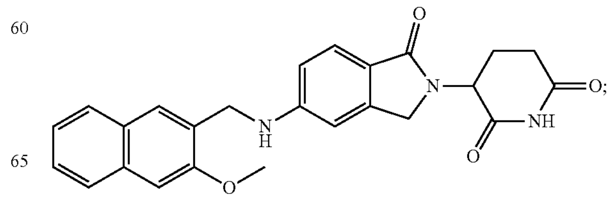

-continued
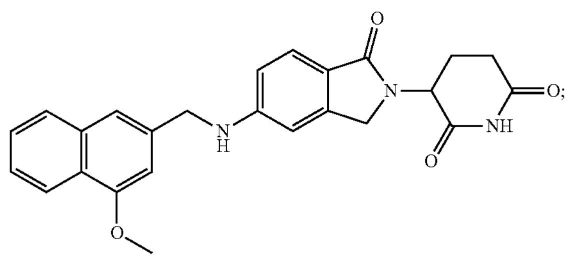
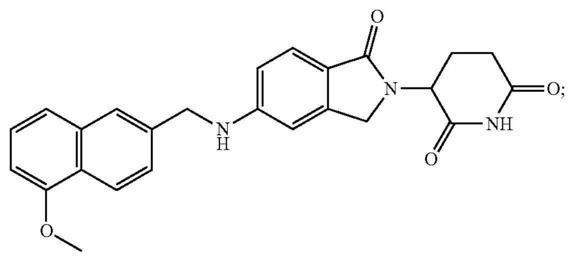
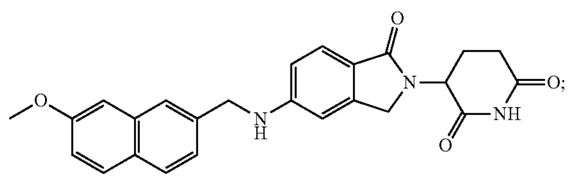
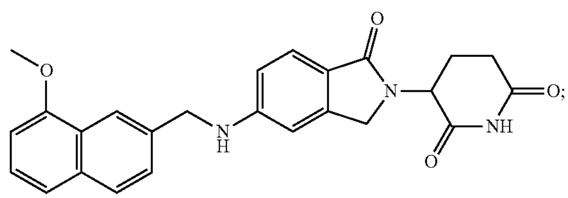
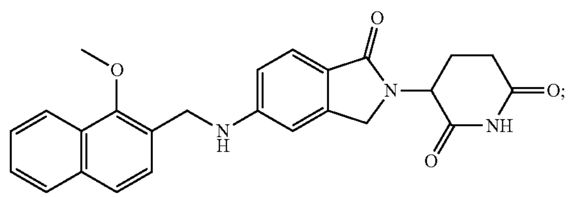
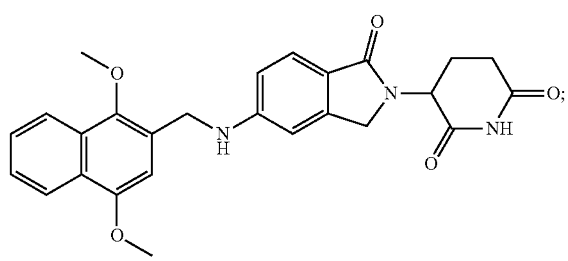
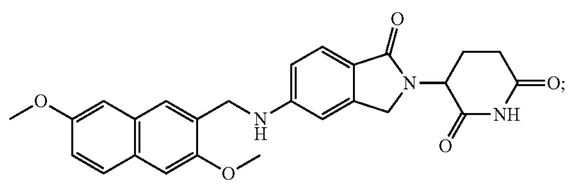
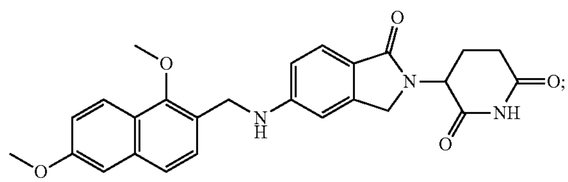
-continued
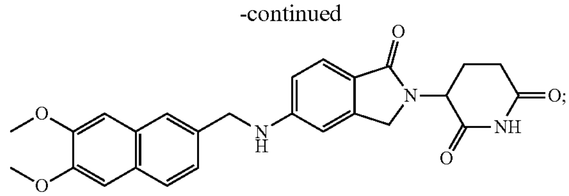
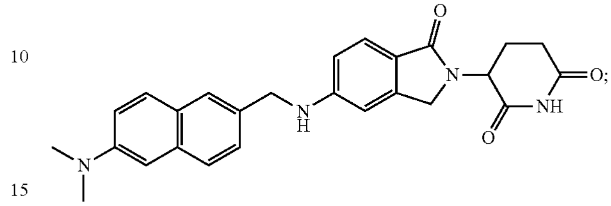
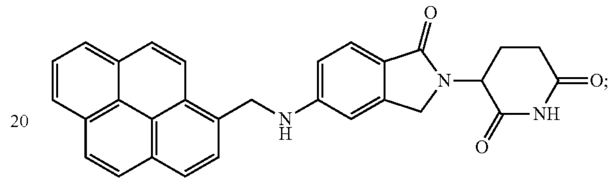
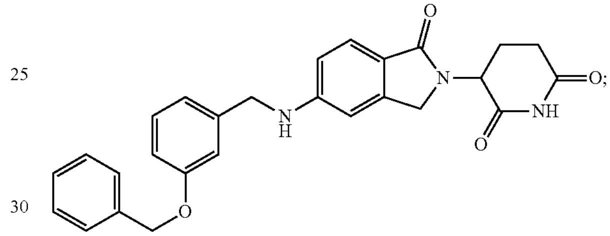
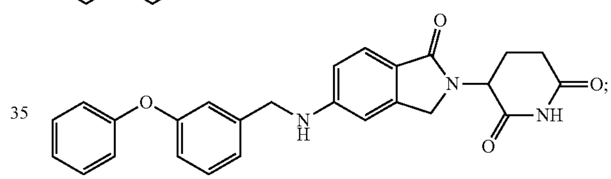
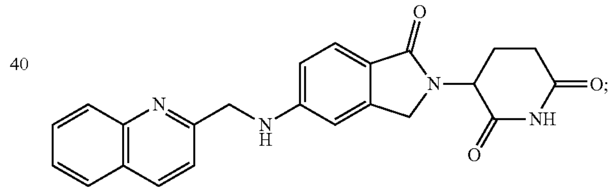
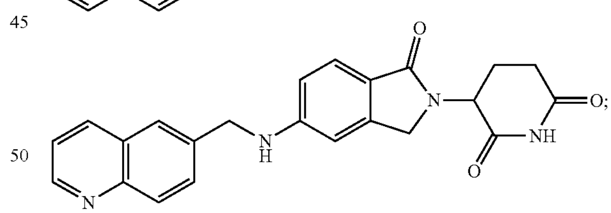
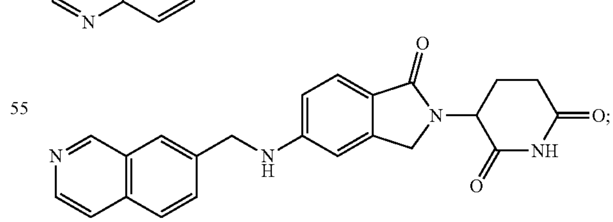
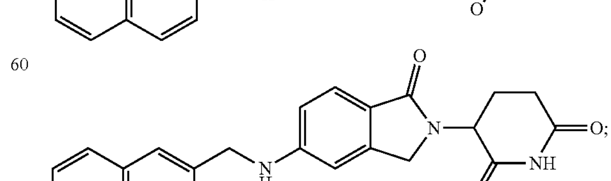
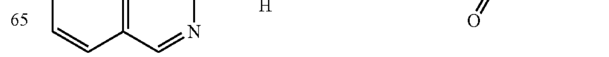

-continued
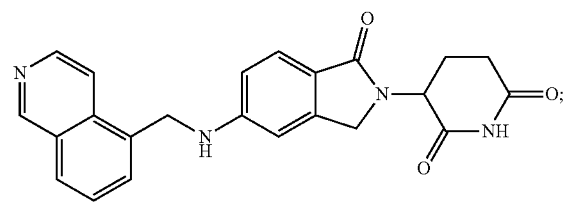
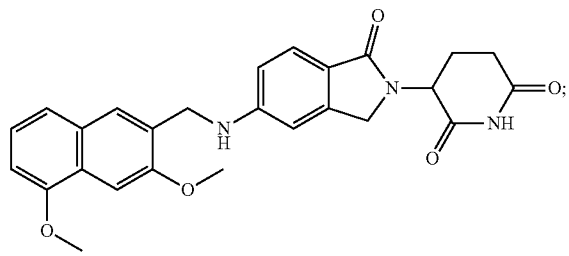
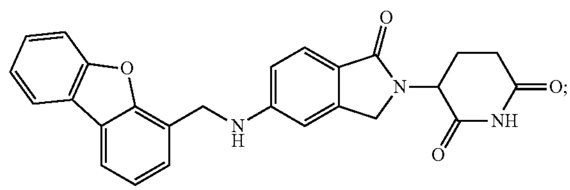
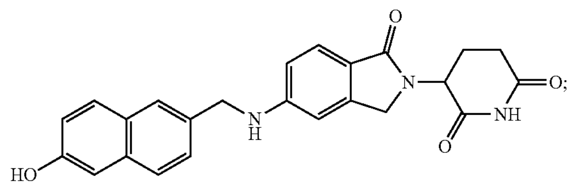
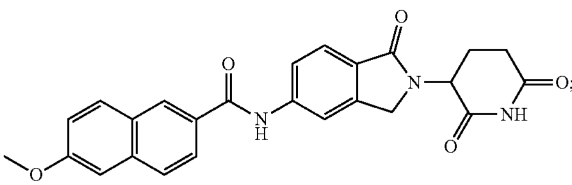
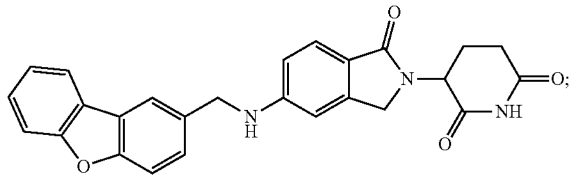
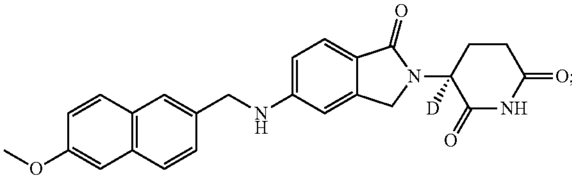
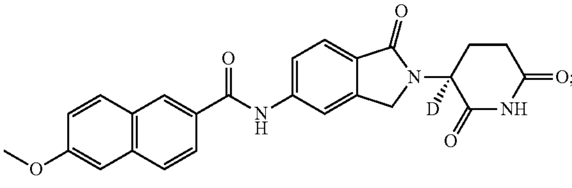
-continued
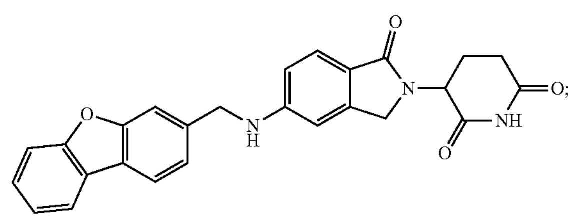
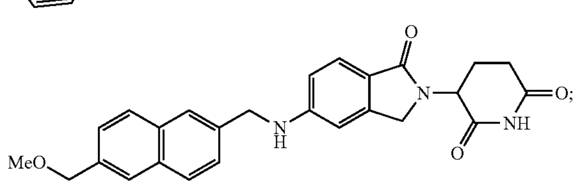
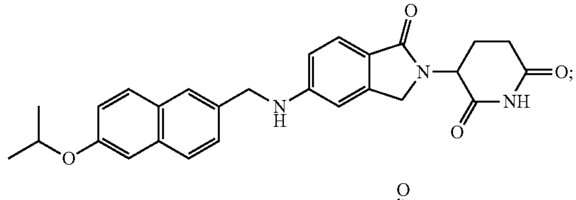
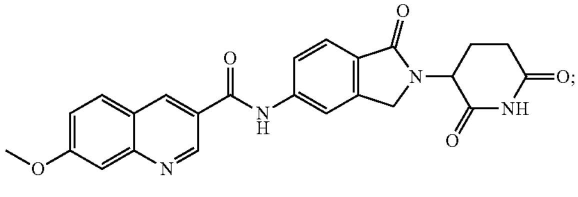
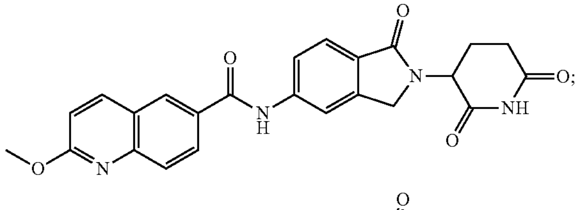
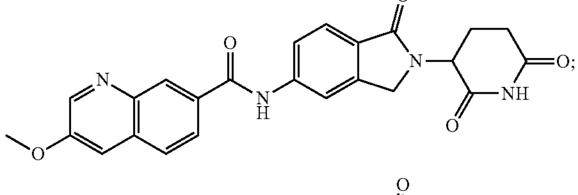
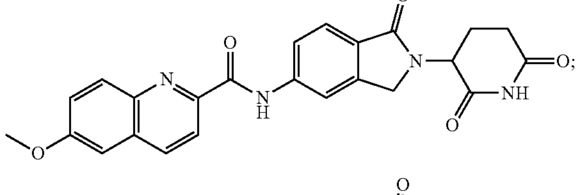
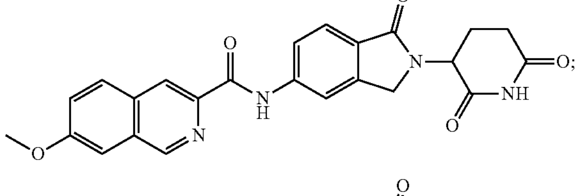
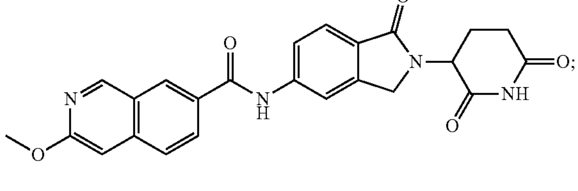

-continued

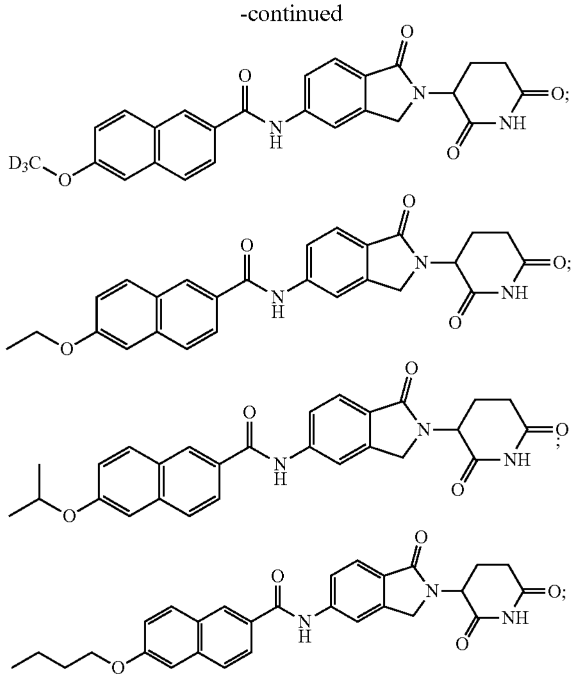

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

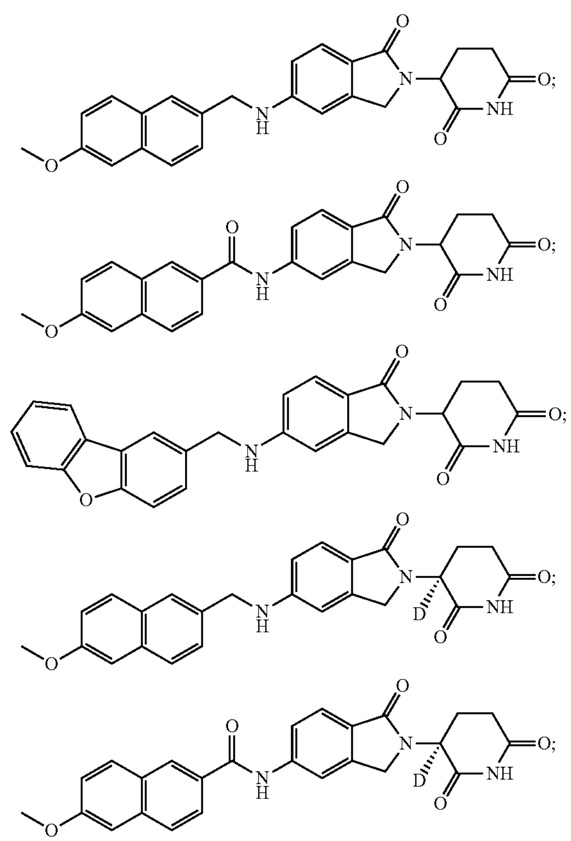

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

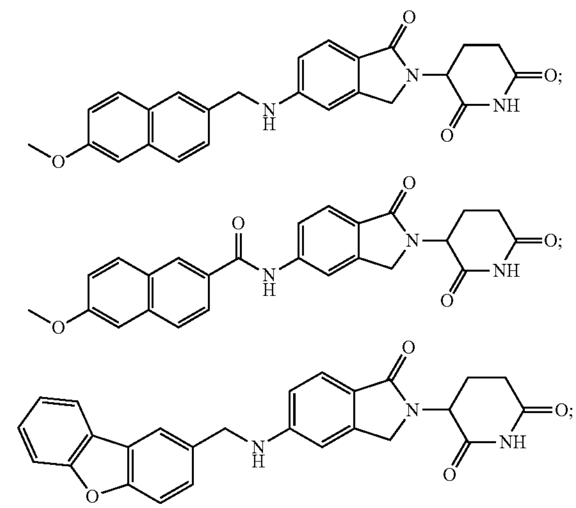

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

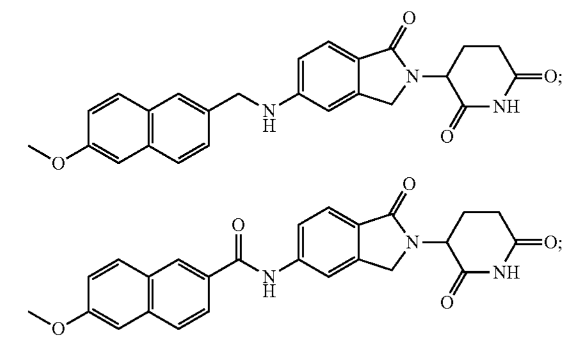

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

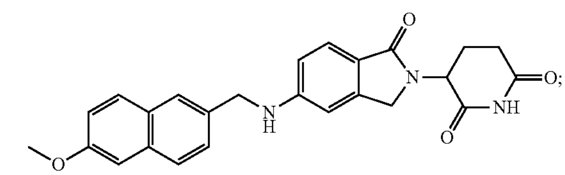 [SMILES: COc1ccc2cc(CNc3ccc4c(c3)CN(C3CCC(=O)NC3=O)C4=O)ccc2c1]

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

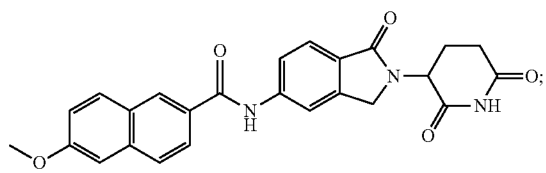 [SMILES: COc1ccc2cc(C(=O)Nc3ccc4c(c3)CN(C3CCC(=O)NC3=O)C4=O)ccc2c1]

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

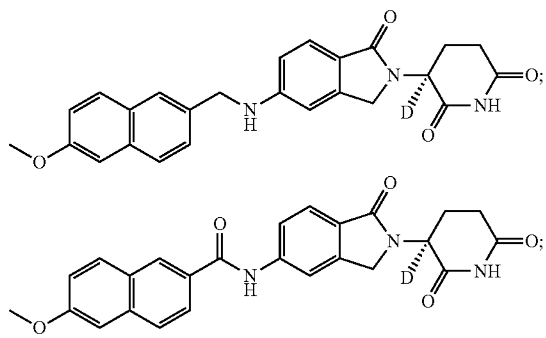

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

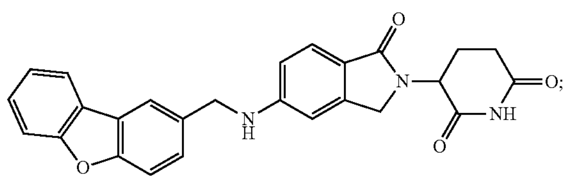 [SMILES: O=C1CCC(N2Cc3cc(NCc4ccc5oc6ccccc6c5c4)ccc3C2=O)C(=O)N1]

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound of the formula:

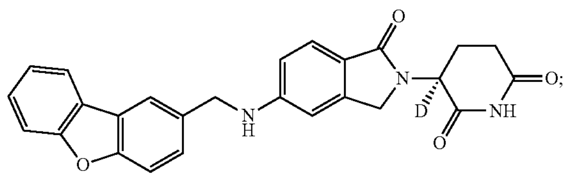 [SMILES: [2H][C@]1(N2Cc3cc(NCc4ccc5oc6ccccc6c5c4)ccc3C2=O)CCC(=O)NC1=O]

or a pharmaceutically acceptable salt, co-crystal, tautomer, stereoisomer, solvate, hydrate, polymorph, isotopically enriched derivative, or prodrug thereof.

In certain embodiments, the compound of Formula (I) binds IKZF2 with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula (I) inhibits IKZF2 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula (I) selectively binds and/or inhibits IKZF2 over another protein. In some embodiments, the compound of Formula (I) selectively binds and/or inhibits IKZF2 over a different IKAROS family protein (e.g., IKZF1, IKZF3, IKZF4, IKZF5). In some embodiments, the compound of Formula (I) selectively binds and/or inhibits IKZF2 over one or more of IKZF1, IKZF3, IKZF4, and IKZF5. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula (I) promotes the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of IKZF2 at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formula (I) increases the rate of IKZF2 degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formula (I), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound of Formula (I) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disorder in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for treating ovarian cancer, gastric cancer, or a hematological cancer in a subject in need thereof. In certain embodiments, the effective amount is an amount effective for treating a hematological cancer in a subject in need thereof. In certain embodiments, the effective amount is an amount effective for treating a leukemia, a lymphoma, or multiple myeloma in a subject in need thereof. In certain embodiments, the effective amount is an amount effective for treating a leukemia or a lymphoma in a subject in need thereof. In certain embodiments, the effective amount is an amount effective for treating primary effusion lymphoma (PEL), del(5q) myelodysplastic syndrome (MDS), acute myeloid leukemia (AML), diffuse large B-cell lymphoma (DLBCL), or T-cell acute lymphoblastic leukemia (T-ALL) in a subject in need thereof. In certain embodiments, the effective amount is an amount effective for treating primary effusion lymphoma (PEL), del(5q) myelodysplastic syndrome (MDS), or acute myeloid leukemia (AML) in a subject in need thereof. In certain embodiments, the effective amount is an amount effective for treating acute myeloid leukemia (AML) in a subject in need thereof. In certain embodiments, the effective amount is an amount effective for treating acute myeloid leukemia (AML) in a subject in need thereof. In certain embodiments, the effective amount is an amount effective for treating diffuse large B-cell lymphoma (DLBCL) in a subject in need thereof. In certain embodiments, the effective amount is an amount effective for treating T-cell acute lymphoblastic leukemia (T-ALL) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal.

In certain embodiments, the animal is a transgenic animal (e.g., transgenic mice and transgenic pigs). In certain embodiments, the subject is a fish or reptile.

In certain embodiments, the effective amount is an amount effective for promoting the degradation of at least about 10%, at least about 20%, at least about 30%, at least about 40%, at least about 50%, at least about 60%, at least about 70%, at least about 80%, at least about 90%, at least about 95%, at least about 98%, or at least about 99% of IKZF2. In certain embodiments, the effective amount is an amount effective for promoting the degradation of IKZF2 by a range between a percentage described in this paragraph and another percentage described in this paragraph, inclusive.

The present disclosure provides pharmaceutical compositions comprising a compound that interacts with IKZF2 for use in treating a proliferative disorder in a subject in need thereof. In certain embodiments, the composition is for use in treating cancer. In certain embodiments, the composition is for use in treating ovarian cancer, gastric cancer, or a hematological cancer. In certain embodiments, the composition is for use in treating a leukemia, a lymphoma, or multiple myeloma. In certain embodiments, the composition is for use in treating a leukemia or a lymphoma. In certain embodiments, the composition is for use in treating primary effusion lymphoma (PEL), del(5q) myelodysplastic syndrome (MDS), acute myeloid leukemia (AML), diffuse large B-cell lymphoma (DLBCL), or T-cell acute lymphoblastic leukemia (T-ALL). In certain embodiments, the effective amount is an amount effective for treating primary effusion lymphoma (PEL), del(5q) myelodysplastic syndrome (MDS), or acute myeloid leukemia (AML) in a subject in need thereof. In certain embodiments, the composition is for use in treating acute myeloid leukemia (AML) in a subject in need thereof. In certain embodiments, the composition is for use in treating diffuse large B-cell lymphoma (DLBCL). In certain embodiments, the composition is for use in treating T-cell acute lymphoblastic leukemia (T-ALL).

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., cancer). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated.

In certain embodiments, a pharmaceutical composition comprising a compound of Formula (I) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula (I) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients, such as cocoa butter and suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a proliferative disorder (e.g., a cancer) in a subject in need thereof. In certain embodiments, the kits are useful for treating cancer (e.g., a hematological cancer) in a subject in need thereof. In certain embodiments, the kits are useful for preventing cancer (e.g., a hematological cancer) in a subject in need thereof. In certain embodiments, the kits are useful for reducing the risk of developing cancer (e.g., a hematological cancer) in a subject in need thereof. In certain embodiments, the kits are useful for promoting the degradation of IKZF2 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, a kit described herein may include one or more additional pharmaceutical agents described herein as a separate composition.

Methods of Treatment

Acute myeloid leukemia (AML) is a genetically complex and heterogeneous set of diseases characterized by a diverse set of mutations. The 5-year overall survival in adult AML is less than 20% and has only improved modestly in the past 30 years, and approximately one third of AML cases are unresponsive to standard treatments. Acquisition of a gene expression program that corresponds to a gain of self-renewal properties imparts a worse clinical outcome in AML patients and correlates with therapy resistance and relapse. Therefore, there is an unmet need to develop new therapies for AML patients. Targeting the mechanisms that contribute to self-renewal and disease progression can provide a new strategy for therapeutic intervention in leukemia.

Recently, IKZF2 was established as a viable target in acute myeloid leukemia (AML) through the key role of IKZF2 in maintenance of leukemia stem cell (LSC) function. As such, degradation of IKZF2 is an attractive method for the development of new anticancer therapy. Accordingly, use of a compound that degrades IKZF2 provides a method of treating cancers that rely on IKZF2 activity.

The present disclosure provides methods for treating proliferative disease. In certain embodiments, the present disclosure provides methods for treating cancer. In certain embodiments, the application provides a method of treating ovarian cancer, gastric cancer, or a hematological cancer. In certain embodiments, the application provides a method of treating a leukemia, a lymphoma, or multiple myeloma. In certain embodiments, the application provides a method of treating a leukemia or a lymphoma. In certain embodiments, the application provides a method of treating primary effusion lymphoma (PEL), del(5q) myelodysplastic syndrome (MDS), acute myeloid leukemia (AML), diffuse large B-cell lymphoma (DLBCL), or T-cell acute lymphoblastic leukemia (T-ALL). In certain embodiments, the application provides a method of treating primary effusion lymphoma (PEL), del(5q) myelodysplastic syndrome (MDS), or acute myeloid leukemia (AML). In certain embodiments, the application provides a method of treating acute myeloid leukemia (AML). In certain embodiments, the application provides a method of treating primary effusion lymphoma (PEL). In certain embodiments, the application provides a method of treating del(5q) myelodysplastic syndrome (MDS). In certain embodiments, the application provides a method of treating diffuse large B-cell lymphoma (DLBCL). In certain embodiments, the application provides a method of treating T-cell acute lymphoblastic leukemia (T-ALL). In certain embodiments, the application provides a method of treating ovarian cancer. In certain embodiments, the application provides a method of treating gastric cancer. In certain embodiments, the application provides a method of promoting the degradation of IKZF2.

In certain embodiments, the methods comprise administering to a subject in need thereof (e.g., a subject with a cancer) a compound that interacts with IKZF2, for example, a compound that is an inhibitor of IKZF2, a modulator of IKZF2, a binder of IKZF2, a compound that modifies IKZF2, or a compound that promotes the degradation of IKZF2. In certain embodiments, the methods comprise administering a compound of Formula (I), or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of Formula (I), or a pharmaceutically acceptable salt, co-crystal, tautomer, stereoisomer, solvate, hydrate, polymorph, isotopically enriched derivative, or prodrug, or composition thereof, to a subject in need thereof.

In certain embodiments, the methods of the disclosure comprise administering to the subject an effective amount of a compound of Formula (I), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula (I), or at different times than the compound of Formula (I). For example, the compound of Formula (I) and any additional pharmaceutical agent(s) may be on the same dosing schedule or different dosing schedules. All or some doses of the compound of Formula (I) may be administered before all or some doses of an additional pharmaceutical agent, after all or some does an additional pharmaceutical agent, within a dosing schedule of an additional pharmaceutical agent, or a combination thereof. The timing of administration of the compound of Formula (I) and additional pharmaceutical agents may be different for different additional pharmaceutical agents.

In certain embodiments, the additional pharmaceutical agent comprises an agent useful in the treatment of proliferative disease. In certain embodiments, the additional pharmaceutical agent is useful in the treatment of cancer. In certain embodiments, the additional pharmaceutical agent is useful in the treatment of ovarian cancer, gastric cancer, or a hematological cancer. In certain embodiments, the additional pharmaceutical agent is useful in the treatment of a hematological cancer. In certain embodiments, the additional pharmaceutical agent cancer is useful in the treatment of multiple myeloma, a leukemia, or a lymphoma. In certain embodiments, the additional pharmaceutical agent cancer is useful in the treatment of a leukemia or a lymphoma. In certain embodiments, the additional pharmaceutical agent is useful in the treatment of primary effusion lymphoma (PEL), del(5q) myelodysplastic syndrome (MDS), acute myeloid leukemia (AML), diffuse large B-cell lymphoma (DLBCL), or T-cell acute lymphoblastic leukemia (T-ALL). In certain embodiments, the additional pharmaceutical agent is useful in the treatment of primary effusion lymphoma (PEL), del(5q) myelodysplastic syndrome (MDS), or acute myeloid leukemia (AML). In certain embodiments, the additional pharmaceutical agent is useful in the treatment of acute myeloid leukemia (AML).

In another aspect, the present disclosure provides methods for promoting the degradation of IKZF2, the method comprising contacting IKZF2 with a compound of Formula (I), or a pharmaceutically acceptable salt, co-crystal, tautomer, stereoisomer, solvate, hydrate, polymorph, isotopically enriched derivative, or prodrug, or composition thereof. In certain embodiments, the degradation is in a cell. In certain embodiments, the degradation is in a subject. In certain embodiments, the degradation is in a biological sample.

In another aspect, the application provides a method of promoting the ubiquitination of IKZF2, the method comprising contacting IKZF2 with a compound of Formula (I), or a pharmaceutically acceptable salt, co-crystal, tautomer, stereoisomer, solvate, hydrate, polymorph, isotopically enriched derivative, or prodrug, or composition thereof. In certain embodiments, the ubiquitination takes place in a cell. In certain embodiments, the ubiquitination takes place in a subject. In certain embodiments, the ubiquitination takes place in a biological sample.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Identification of lead compounds that are degraders of IKZF2

Initial studies identified a core chemical scaffold with IKZF2 degrading properties. Further structure-activity relationship (SAR) studies guided the design of additional analogs. After screening the analogs, DEG-7 was identified as having robust IKZF2 degradation in MOLM13 cells and is a lead compound for the development of a pro-differentiation therap targeting cancer stem cells in AML. DEG-35 was identified as having robust IKZF2 degradation activity and selective nanomolar anti-proliferative activity against AML cells and was selected as a lead for development of a dual-targeting AML therapy.

Compound Synthesis

Compounds of Formula (I) may be prepared using the synthetic schemes and procedures described in detail below.

3-(5-(((6-methoxynaphthalen-2-yl)methyl)amino)-1-oxoisoindolin-2-yl)piperidine-2,6-dione (DEG-7)

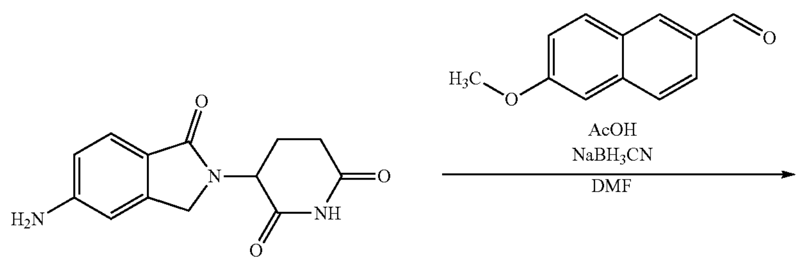

-continued

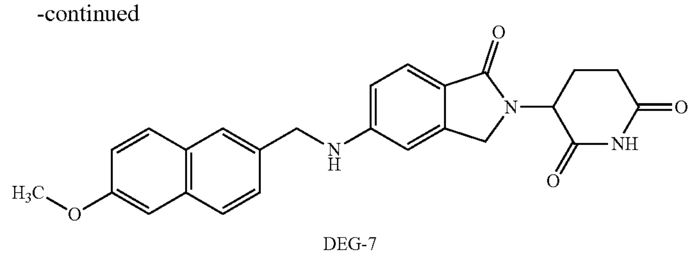

DEG-7

3-(5-(((6-methoxynaphthalen-2-yl)methyl)amino)-1-oxoisoindolin-2-yl)piperidine-2,6-dione (DEG-7): In a 1-dram vial containing a stirbar, 5-$NH_2$-lenalidomide (27 mg, 1.0 equiv) was dissolved in DMF (780 pL). 6-methoxy-2-naphthaldehyde (58 mg, 3.0 equiv) was added followed by acetic acid (17 μL, 3.0 equiv). The solution was stirred for 3 h at 24° C. Sodium cyanoborohydride (20 mg, 3.0 equiv) was then added and the solution was stirred for 16 h at 24° C. The reaction was quenched with a solution of saturated sodium bicarbonate (1 mL) and diluted with chloroform (1 mL). The biphasic mixture was transferred to a separatory funnel and the organic layer was collected. The aqueous layer was extracted with 25% isopropanol-chloroform (1×2 mL) and the combined organic layers were dried over sodium sulfate. The dried solution was filtered through cotton and the filtrate was concentrated by rotary evaporation. The solid obtained was purified by flash gel chromatography ($SiO_2$, 2-4% methanol-dichloromethane, 2 steps) followed by reversed phase HPLC to afford DEG-7 as a white solid (9 mg, 20%). HRMS-ESI (m/z): $[M+H]^+$ calculated for $C_{25}H_{44}N_3O_4$, 430.1761; found, 430.1765.

N-(2-(2,6-dioxopiperidin-3-yl)-1-oxoisoindolin-5-yl)-6-methoxy-2-naphthamide (DEG-35)

N-(2-(2,6-dioxopiperidin-3-yl)-1-oxoisoindolin-5-yl)-6-methoxy-2-naphthamide (DEG-35): In a flame-dried round-bottom flask, 6-methoxy-2-naphthoic acid (23 mg, 1.5 equiv) was dissolved in DMF (771 μL). 5-$NH_2$-lenalidomide (20 mg, 1.0 equiv) was added followed by HATU (88 mg, 3.0 equiv). Diisopropylethylamine (40 μL) was added and the solution was stirred for 12 h at 24° C. The reaction was quenched with the addition of a saturated solution of sodium bicarbonate (2 mL) and diluted with ethyl acetate (1 mL). The biphasic mixture was transferred to a separatory funnel and the organic layer was collected. The aqueous layer was extracted with ethyl acetate (2×2 mL) and the combined organic layers were dried over sodium sulfate. The dried solution was filtered through cotton and the filtrate was concentrated by rotary evaporation. The solid obtained was purified by flash gel chromatography ($SiO_2$, 2-4% methanol-dichloromethane, 2 steps) followed by reversed phase HPLC to afford DEG-35 as a white solid (7 mg, 21%). HRMS-ESI (m/z): [M+H]+ calculated for $C_{25}H_{44}N_3O_4$, 430.1761; found, 430.1765.

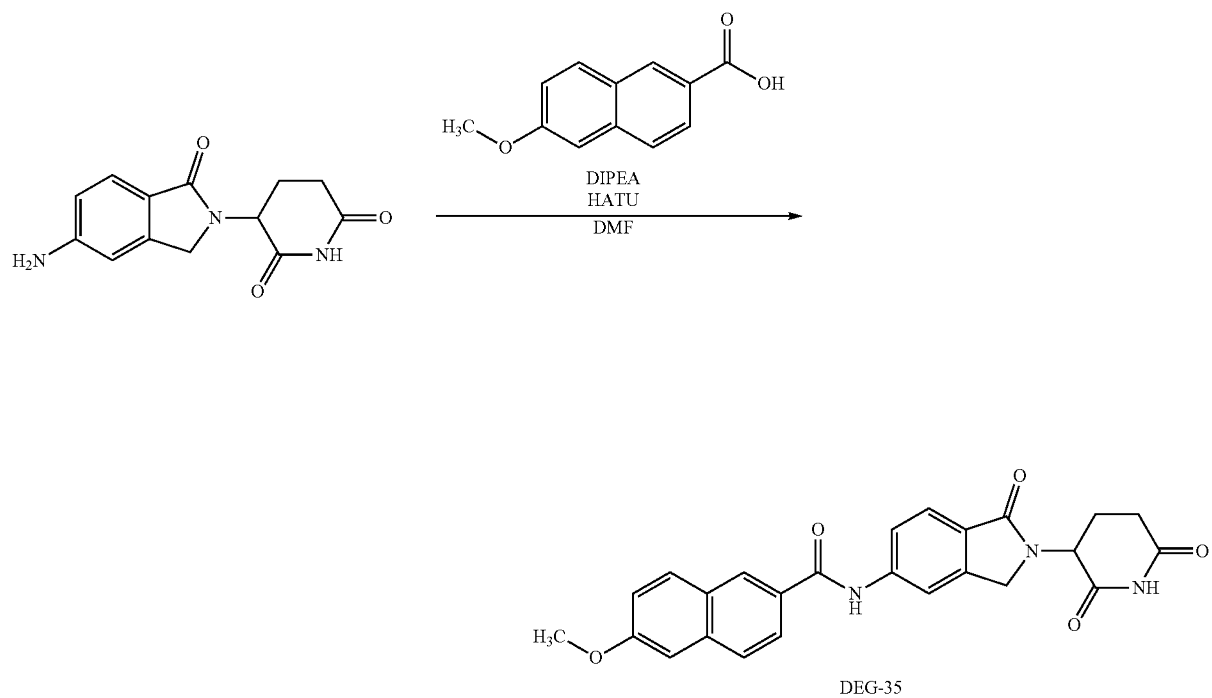

DEG-35

3-(5-((dibenzo[b,d]furan-2-ylmethyl)amino)-1-oxoisoindolin-2-yl)piperidine-2,6-dione (DEG-37)

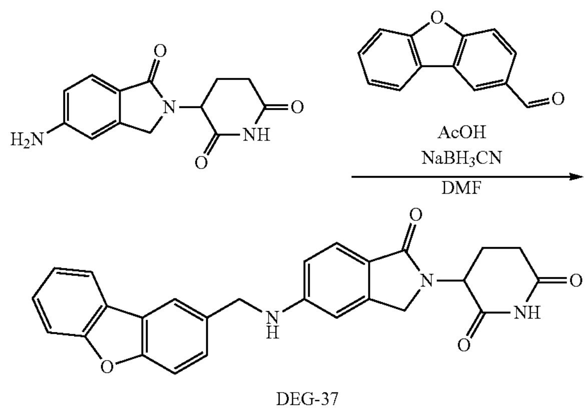

DEG-37

3-(5-((dibenzo[b,d]furan-2-ylmethyl)amino)-1-oxoisoindolin-2-yl)piperidine-2,6-dione (DEG-37): In a 1-dram vial containing a stirbar, 5-$NH_2$-lenalidomide (20 mg, 1.0 equiv) was dissolved in DMF (780 μL). Dibenzo[b,d]furan-2-carbaldehyde (45 mg, 3.0 equiv) was added followed by acetic acid (13 μL, 3.0 equiv). Sodium cyanoborohydride (15 mg, 3.0 equiv) was then added and the solution was stirred for 16 h at 24° C. The reaction was quenched with a solution of saturated sodium bicarbonate (1 mL) and diluted with ethyl acetate (1 mL). The biphasic mixture was transferred to a separatory funnel and the organic layer was collected. The aqueous layer was extracted with ethyl acetate (2×2 mL) and the combined organic layers were dried over sodium sulfate. The dried solution was filtered through cotton and the filtrate was concentrated by rotary evaporation. The solid obtained was purified by flash gel chromatography ($SiO_2$, 2-5% methanol-dichloromethane, 3 steps) followed by reversed phase HPLC to afford DEG-37 as a white solid (5 mg, 15%). HRMS-ESI (m/z): $[M+H]^+$ calculated for $C_{26}1H_{22}N_3O_4$, 440.1605; found, 440.1602.

Additional compounds of Formula (I), shown below, were prepared in an analogous manner to the methods used to prepare DEG-7, DEG-35, and DEG-37.

| | Compound structure | Characterization |
|---|---|---|
| DEG-1 | 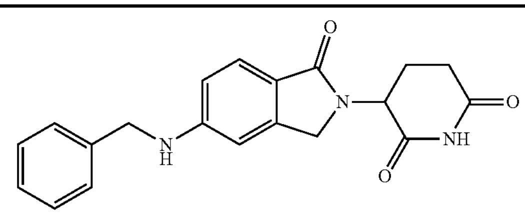 3-(5-(benzylamino)-1-oxoisoindolin-2-yl)piperidine-2,6-dione | $^1H$ NMR (400 MHz, DMSO-$d_6$) δ 10.90 (s, 1H), 7.40-7.29 (m, 5H), 7.27-7.19 (m, 1H), 6.99 (t, J = 5.9 Hz, 1H), 6.69 (d, J = 8.5 Hz, 1H), 6.65 (s, 1H), 4.99 (dd, J = 13.2, 5.0 Hz, 1H), 4.35 (d, J = 5.7 Hz, 2H), 4.23 (d, J = 16.7 Hz, 1H), 4.10 (d, J = 16.7 Hz, 1H), 2.88 (ddd, J = 18.1, 13.8, 5.2 Hz, 1H), 2.62-2.52 (m, 1H), 2.31 (qd, J = 13.1, 4.1 Hz, 1H), 2.06-1.82 (m, 1H). $^{13}C$ NMR (101 MHz, DMSO-$d_6$) δ 172.94, 171.39, 168.62, 152.05, 144.32, 139.49, 128.38, 127.13, 126.78, 123.91, 119.16, 112.69, 104.74, 51.27, 46.74, 46.07, 31.26, 22.61. $[M + H]^+$ calculated for $C_{20}H_{20}N_3O_3$, 350.1499; found, 350.1501. |
| DEG-2 | 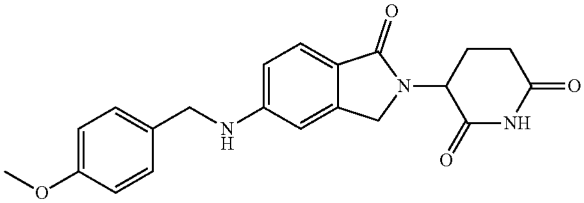 3-(5-((4-methoxybenzyl)amino)-1-oxoisoindolin-2-yl)piperidine-2,6-dione | $^1H$ NMR (600 MHz, DMSO-$d_6$) δ 10.91 (s, 1H), 7.37 (d, J = 8.4 Hz, 1H), 7.27 (d, J = 8.5 Hz, 2H), 6.93-6.86 (m, 3H), 6.68 (dd, J = 8.4, 1.8 Hz, 1H), 6.64 (s, 1H), 4.99 (dd, J = 13.4, 5.1 Hz, 1H), 4.27 (d, J = 5.9 Hz, 2H), 4.23 (d, J = 16.7 Hz, 1H), 4.10 (d, J = 16.7 Hz, 1H), 3.72 (s, 3H), 2.88 (ddd, J = 17.7, 13.6, 5.3 Hz, 1H), 2.60-2.54 (m, 1H), 2.31 (qd, J = 13.3, 4.5 Hz, 1H), 1.95-1.90 (m, 1H). $^{13}C$ NMR (101 MHz, DMSO-$d_6$) δ 172.95, 171.40, 168.65, 158.21, 152.05, 144.31, 131.20, 128.40, 123.87, 119.06, 113.80, 112.72, 104.72, 55.03, 51.27, 46.74, 45.55, 31.27, 22.62. HRMS-ESI (m/z): $[M + H]^+$ calculated for $C_{21}H_{22}N_3O_4$, 380.1605; found, 380.1607. |
| DEG-3 | 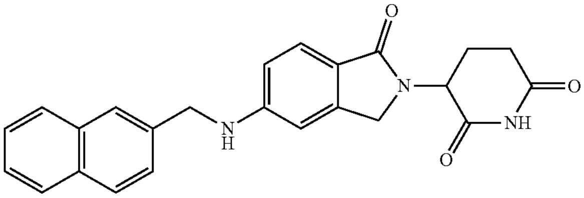 3-(5-(naphthalen-2-ylmethyl)amino)-1-oxoisoindolin-2-yl)piperidine-2,6-dione | $^1H$ NMR (400 MHz, DMSO-$d_6$) δ 10.90 (s, 1H), 7.93-7.80 (m, 4H), 7.52 (dd, J = 8.6, 1.4 Hz, 1H), 7.50-7.45 (m), 7.38 (d, J = 8.4 Hz, 1H), 7.11 (t, J = 5.9 Hz, 1H), 6.74 (dd, J = 8.4, 1.8 Hz, 1H), 6.70 (s, 1H), 4.99 (dd, J = 13.3,5.1 Hz, 1H), 4.53 (d, J = 5.6 Hz, 2H), 4.23 (d, J = 16.8 Hz, 1H), 4.10 (d, J = 16.7 Hz, 1H), 2.87 (ddd, J = 17.5, 13.6, 5.4 Hz, 1H), 2.60-2.56 (m, 1H), 2.29 (qd, J = 13.1, 4.5 Hz, 1H), 1.96-1.83 (m, 1H). $^{13}C$ NMR (101 MHz, DMSO-$d_6$) δ 172.93, 171.37, 168.60, 152.06, 144.35, 137.18, 132.96, 132.20, 128.02, 127.55, 127.52, 126.17, 125.73, 125.61, 125.18, 123.95, 119.25, 112.75, |

-continued

| | Compound structure | Characterization |
|---|---|---|
| | | 104.82, 51.26, 46.74, 46.31, 31.25, 22.61. HRMS-ESI (m/z): $[M + H]^+$ calculated for $C_{24}H_{22}N_3O_3$, 400.1656; found, 400.1658. |
| DEG-6 | 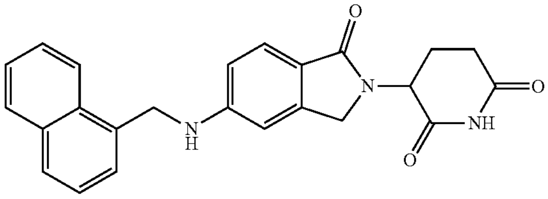 3-(5-((naphthalen-1-ylmethyl)amino)-1-oxoisoindolin-2-yl)piperidine-2,6-dione | $^1H$ NMR (400 MHz, ACETONE-$d_6$) δ 9.66 (s, 1H), 8.14 (d, J = 8.4 Hz, 1H), 7.97-7.93 (m, 1H), 7.85 (d, J = 8.2 Hz, 1H), 7.59-7.53 (m, 3H), 7.50-7.43 (m, 2H), 6.87 (dd, J = 8.4, 2.0 Hz, 1H), 6.82 (s, 1H), 5.11 (dd, J = 13.4,5.1 Hz, 1H), 4.90 (d, J = 5.3 Hz, 2H), 4.32 (d, J = 16.2 Hz, 1H), 4.27 (d, J = 16.4 Hz, 1H), 3.00-2.90 (m, 1H), 2.76-2.70 (m, 1H), 2.5 (qd, J = 26.6, 13.4, 4.6 Hz, 1H), 2.16-2.09 (m, 1H). $^{13}C$ NMR (101 MHz, ACETONE-$d_6$) δ 171.66, 169.74, 153.28, 145.67, 135.14, 134.95, 132.48, 129.55, 128.68, 127.05, 126.66, 126.37, 126.13, 125.11, 124.36, 121.35, 113.93, 105.84, 52.54, 47.58, 46.00, 32.30, 24.06. HRMS-ESI (m/z): $[M + H]^+$ calculated for $C_{24}H_{22}N_3O_3$, 400.1656; found, 400.1655. |
| DEG-7 | 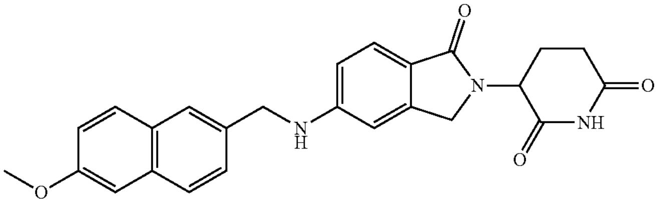 3-(5-(((6-methoxynaphthalen-2-yl)methyl)amino)-1-oxoisoindolin-2-yl)piperidine-2,6-dione | $^1H$ NMR (400 MHz, DMSO-$d_6$) δ 10.90 (s, 1H), 7.81-7.74 (m, 3H), 7.47 (d, J = 8.3 Hz, 1H), 7.38 (d, J = 8.3 Hz, 1H), 7.29 (d, J = 2.4 Hz, 1H), 7.13 (dd, J = 9.0, 2.5 Hz, 1H), 7.06 (t, J = 5.9 Hz, 1H), 6.73 (d, J = 8.8 Hz, 1H), 6.69 (s, 1H), 4.99 (dd, J = 13.3, 5.0 Hz, 1H), 4.48 (d, J = 5.6 Hz, 2H), 4.23 (d, J = 16.7 Hz, 1H), 4.09 (d, J = 16.8 Hz, 1H), 2.93-2.82 (m, 1H), 2.56 (d, J = 17.6 Hz, 1H), 2.30 (qd, J = 13.2, 4.4 Hz, 1H), 1.94-1.87 (m, 1H). $^{13}C$ NMR (101 MHz, DMSO-$d_6$) 172.93, 171.37, 168.60, 157.03, 152.09, 144.33, 134.56, 133.42, 129.02, 128.36, 126.94, 126.24, 125.20, 123.92, 119.16, 118.64, 112.72, 105.84, 104.76, 55.14,51.25, 46.74, 46.26, 31.25, 22.61. HRMS-ESI (m/z): $[M + H]^+$ calculated for $C_{25}H_{24}N_3O_4$, 430.1761; found, 430.1765. |
| DEG-8 | 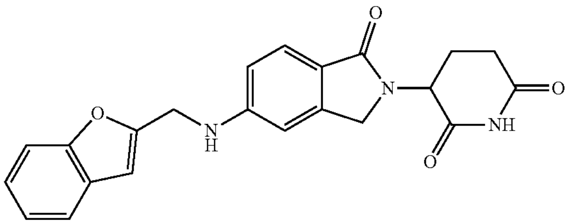 3-(5-((benzofuran-2-ylmethyl)amino)-1-oxoisoindolin-2-yl)piperidine-2,6-dione | $^1H$ NMR (400 MHz, DMF-$d_7$) δ 10.87 (s, 1H), 7.60 (d, J = 7.3 Hz, 1H), 7.54 (d, J = 8.0 Hz, 1H), 7.51-7.47 (m, 1H), 7.32-7.27 (m, 1H), 7.25-7.20 (m, 1H) 7.00 (t, J = 6.0 Hz, 1H), 6.96-6.91 (m, 2H), 6.85 (s, 1H), 5.15 (dd, J = 13.3, 5.1 Hz, 1H), 4.65 (d, J = 5.8 Hz, 2H), 4.37 (d, J = 16.5 Hz, 1H), 4.28 (d, J = 16.5 Hz, 1H), 3.00 (ddd, J = 18.0, 14.2, 6.0 Hz, 1H), 2.74-2.65 (m, 1H), 2.49 (qd, J = 13.3, 4.5 Hz, 1H), 2.14-2.07 (m, 1H). $^{13}C$ NMR (101 MHz, DMF-$d_7$) δ 173.08, 171.71, 169.23, 156.69, 155.14, 152.43, 145.06, 128.90, 124.29, 124.23, 123.10, 121.21, 120.71, 113.40, 111.19, 105.53, 104.13, 52.08, 47.28, 40.78, 31.83, 23.42. HRMS-ESI (m/z): $[M + Na]^+$ calculated for $C_{22}H_{19}N_3O_4Na$, 412.1268; found, 412.1285. |
| DEG-9 | 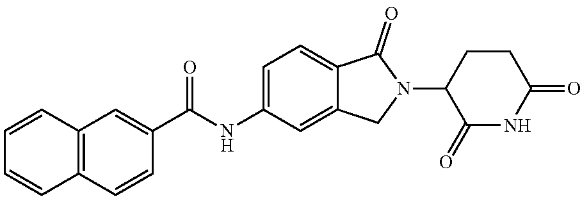 N-(2-(2,6-dioxopiperdin-3-yl)-1-oxoisoindolin-5-yl)-2-naphthamide | $^1H$ NMR (400 MHz, DMSO-$d_6$) δ 11.00 (s, 1H), 10.77 (s, 1H), 8.62 (s, 1H), 8.20 (s, 1H), 8.12-8.01 (m, 4H), 7.90 (dd, J = 8.3, 1.6 Hz, 1H), 7.74 (d, J = 8.3 Hz, 1H), 7.69-7.62 (m, 2H), 5.11 (dd, J = 13.3, 5.1 Hz, 1H), 4.49 (d, J = 17.3 Hz, 1H), 4.35 (d, J = 17.2 Hz, 1H), 2.93 (ddd, J = 18.1, 13.6, 5.3 Hz, 1H), 2.65-2.58 (m, 1H), 2.41 (ddd, J = 19.3, 13.3, 4.4 Hz, 1H), 2.06-1.99 (m, 1H). $^{13}C$ NMR (101 MHz, DMSO-$d_6$) δ 173.39, 171.61, 168.33, 166.51, 143.62, 143.02, 134.86, 132.52, 132.45, 129.49, 128.70, 128.59, 128.47, 128.19, 127.42, 127.26, 124.94, 124.03, 120.44, 114.90, 52.05, 47.68, |

-continued

| | Compound structure | Characterization |
|---|---|---|
| | | 31.71, 23.03. HRMS-ESI (m/z): $[M + H]^+$ calculated for $C_{24}H_{20}N_3O_4$, 414.1448; found, 414.1448. |
| DEG-10 | 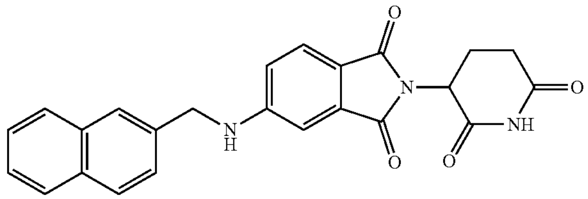 2-(2,6-dioxopiperdin-3-yl)-5-((naphthalen-2-ylmethyl)amino)isoindoline-1,3-dione | $^1$H NMR (400 MHz, DMSO-$d_6$) δ 11.04 (s, 1H), 7.92-7.80 (m, 5H), 7.56 (d, J = 8.4 Hz, 1H), 7.53-7.46 (m, 3H), 7.02 (s, 1H), 6.93, (d, J = 8.7 Hz, 1H), 5.01 (dd, J = 12.7, 5.4 Hz, 1H), 4.63 (d, J = 5.7 Hz, 2H), 2.91-2.80 (m, 1H), 2.58-2.52 (m, 1H), 2.47-2.42 (m, 1H), 2.00-1.93 (m, 1H). $^{13}$C NMR (101 MHz, DMSO-$d_6$) δ 172.79, 170.12, 167.59, 167.08, 154.27, 136.27, 134.07, 132.93, 132.24, 128.20, 127.57, 127.54, 126.27, 125.76, 125.63, 125.25, 125.08, 116.57, 115.97, 105.79, 48.61, 46.10, 30.96, 22.18. HRMS-ESI (m/z): $[M + H]^+$ calculated for $C_{24}H_{20}N_3O_4$, 414.1448; found, 414.1446. |
| DEG-11 | 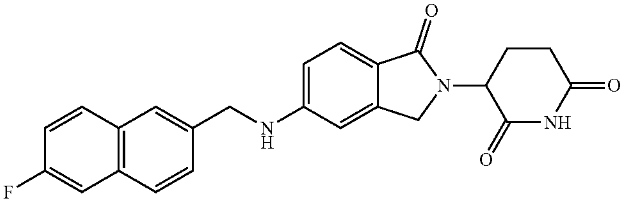 3-(5-(((6-fluoronaphthalen-2-yl)methyl)amino)-1-oxoisoindolin-2-yl)piperidine-2,6-dione | $^1$H NMR (400 MHz, DMSO-$d_6$) δ 10.90 (s, 1H), 7.99-7.93 (m, 1H), 7.91-7.86 (m, 2H), 7.68 (dd, J = 10.3, 2.5 Hz, 1H), 7.56 (d, J = 8.6 Hz, 1H), 7.42-7.36 (m, 2H), 7.11 (t, J = 5.9 Hz, 1H), 6.73 (d, J = 8.4 Hz, 1H), 6.69 (s, 1H), 4.98 (dd, J = 13.2 Hz, 5.1 Hz, 1H), 4.52 (d, J = 5.7 Hz, 2H), 4.23 (d, J = 16.7 Hz, 1H), 4.09 (d, J = 16.7 Hz, 1H), 2.92-2.81 (m, 1H), 2.59-2.52 (m, 1H), 2.35-2.24 (m, 1H), 1.95-1.88 (m, 1H). $^{13}$C NMR (101 MHz, DMSO-$d_6$) δ 172.98, 171.41, 168.58, 152.00, 144.34, 136.66 (d, J = 9.4 Hz), 132.84 (d, J = 9.4 Hz), 130.35 (d, J = 9.0 Hz), 130.11, 127.54, 127.49, 126.91, 125.31, 123.94, 119.28, 116.24 (d, J = 25.4 Hz), 112.73, 110.56 (d, J = 20.3 Hz), 104.82, 51.26, 46.74, 46.18, 31.27, 22.62. $^{19}$F NMR (376 MHz, DMSO-$d_6$) δ −115.03, −115.05, −115.07, −115.10. |
| DEG-12 | 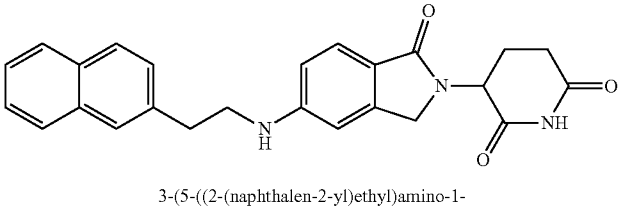 3-(5-((2-(naphthalen-2-yl)ethyl)amino-1-oxoisoindolin-2-yl)piperidine-2,6-dione | $^1$H NMR (400 MHz, DMSO-$d_6$) δ 10.92 (s, 1H), 7.90-7.83 (m, 3H), 7.79 (s, 1H), 7.51-7.38 (m, 4H), 6.74-6.70 (m, 2H), 6.51 (t, J = 5.6 Hz, 1H), 5.02 (dd, J = 13.3 Hz, 1H), 4.28 (d, J = 16.7 Hz, 1H), 4.15 (d, J =16.7 Hz, 1H), 3.44 (q, J = 6.6 Hz, 2H), 3.04 (t, J = 7.3 Hz, 2H), 2.95-2.84 (m, 1H), 2.62-2.53 (m, 1H), 2.40-2.28 (m, 1H), 1.98-1.90 (m, 1H). $^{13}$C NMR (101 MHz, DMSO-$d_6$) δ 173.43, 171.92, 169.18, 152.50, 145.03, 137.76, 133.63, 132.22, 128.22, 128.04, 127.95, 127.81, 127.24, 126.47, 125.81, 124.43, 119.39, 113.09, 104.82, 51.76, 47.27, 44.61, 35.17, 31.77, 23.13. IR (ATR-FTIR), $cm^{-1}$: HRMS-ESI (m/z): $[M + H]^+$ calculated for $C_{25}H_{24}N_3O_3$, 414.1812; found, 414.1809. |
| DEG-13 | 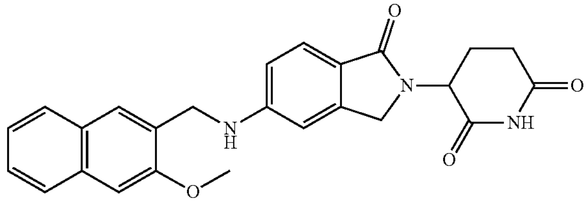 3-(5-(((3-methoxynaphthalen-2-yl)methyl)amino)-1-oxoisoindolin-2-yl)piperidine-2,6-dione | $^1$H NMR (400 MHz, DMSO-$d_6$) δ 10.90 (s, 1H), 7.81 (d, J = 8.1 Hz, 1H), 7.73 (d, J = 8.1 Hz, 1H), 7.69 (s, 1H), 7.44-7.36 (m, 3H), 7.29 (t, J = 8.0 Hz, 1H), 6.95 (t, J = 5.9 Hz, 1H), 6.72 (dd, J = 8.4, 1.9 Hz, 1H), 6.66 (s, 1H), 4.99 (dd, J = 13.2, 5.1 Hz, 1H), 4.45 (d, J = 5.8 Hz, 2H), 4.23 (d, J = 16.9 Hz, 1H), 4.10 (d, J = 16.8 Hz, 1H), 3.97 (s, 3H), 2.93-2.83 (m, 1H), 2.59-2.52 (m, 1H), 2.35-2.24 (m, 1H), 1.95-1.88 (m, 1H). $^{13}$C NMR (101 MHz, DMSO-$d_6$) δ 172.93, 171.39, 168.61, 155.61, 152.15, 144.42, 133.46, 128.43, 128.04, 127.25, 126.36, 126.07, 125.92, 123.99, 123.67, 119.19, 112.64, 105.32, |

-continued

| | Compound structure | Characterization |
|---|---|---|
| | | 104.60, 55.52, 51.26, 46.76, 41.74, 31.25, 22.63. HRMS-ESI (m/z): $[M + H]^+$ calculated for $C_{25}H_{24}N_3O_4$, 430.1761; found, 430.1761 |
| DEG-14 | 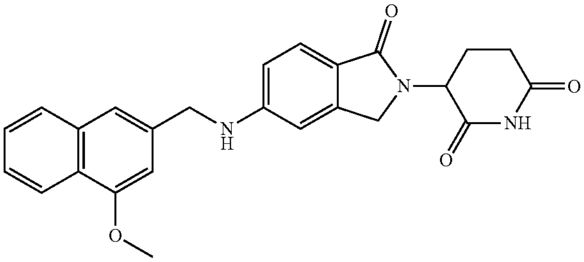 3-(5-(((4-methoxynaphthalen-2-yl)methyl)amino)-1-oxoisoindolin-2-yl)piperidine-2,6-dione | $^1$H NMR (400 MHz, DMSO-$d_6$) δ 10.90 (s, 1H), 8.09 (d, J = 8.0 Hz, 1H), 7.79 (d, J = 8.2 Hz, 1H), 7.50-7.38 (m, 4H), 7.09 (t, J = 5.9 Hz, 1H), 7.00 (s, 1H), 6.74 (dd, J = 8.4, 1.76 Hz, 1H), 6.71 (s, 1H), 4.99 (dd, J = 13.3, 5.1 Hz, 1H), 4.49 (d, J = 5.9 Hz, 2H), 4.23 (d, J = 16.8 Hz, 1H), 4.10 (d, J = 16.9 Hz, 1H), 3.97 (s, 3H), 2.92-2.83 (m, 1H), 2.58-2.53 (m, 1H), 2.35-2.24 (m, 1H), 1.93-1.88 (m, 1H). $^{13}$C NMR (101 MHz, DMSO-$d_6$) δ 172.93, 171.38, 168.60, 154.98, 152.13, 144.32, 137.68, 133.84, 127.32, 126.69, 124.94, 124.09, 123.94, 121.36, 119.26, 117.25, 112.75, 104.85, 104.04, 55.55, 51.26, 46.78, 46.74, 31.25, 22.61. HRMS-ESI (m/z): $[M + H]^+$ calculated for $C_{25}H_{24}N_3O_4$, 430.1761; found, 430.1764. |
| DEG-15 | 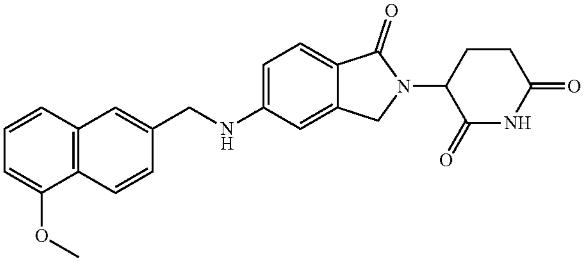 3-(5-(((6,7-dimethoxynaphthalen-2-yl)methyl)amino)-1-oxoisoindolin-2-yl)piperidine-2,6-dione | $^1$H NMR (400 MHz, DMF-$d_7$) δ 10.83 (s, 1H), 8.16, 8.15 (dd, J = 8.6, 2.6 Hz, 1H), 7.87 (s, 1H), 7.55 (d, J = 8.2 Hz, 1H), 7.46-7.37 (m, 3H), 7.06-7.00 (m, 1H), 6.96-6.90 (m, 1H), 6.84 (d, J = 8.3 Hz, 1H), 6.79 (s, 1H), 5.13-5.05 (m, 1H), 4.59 (s, 2H), 4.28 (d, J = 18.4 Hz, 1H), 4.19 (d, J = 18.5 Hz, 1H), 3.01-2.88 (m, 1H), 2.72-2.63 (m, 1H), 2.47-2.37 (m, 1H), 2.10-1.96 (m, 1H). $^{13}$C NMR (101 MHz, DMF-$d_7$) δ 173.08, 171.68, 169.32, 155.65, 152.85, 145.03, 138.25, 134.88, 126.80, 125.64, 125.38, 124.78, 124.26, 122.24, 120.19, 120.15, 113.36, 105.35, 104.29, 55.59, 52.03, 47.23, 47.15, 31.79, 23.36. HRMS-ESI (m/z): $[M + H]^+$ calculated for $C_{25}H_{24}N_3O_4$, 430.1761; found, 430.1763. |
| DEG-16 | 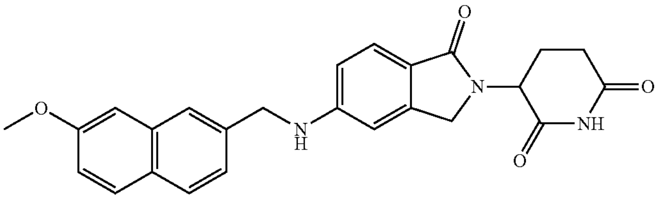 3-(5-(((7-methoxynaphthalen-2-yl)methyl)amino)-1-oxoisoindolin-2-yl)piperidine-2,6-dione | $^1$H NMR (400 MHz, DMSO-$d_6$) δ 10.90 (s, 1H), 7.79 (t, J = 7.9 Hz, 2H), 7.73 (s, 1H), 7.39 (d, J = 8.4 Hz, 1H), 7.34 (dd, J = 8.4, 1.5 Hz, 1H), 7.25 (d, J = 2.4 Hz, 1H), 7.13-7.08 (m, 2H), 6.72 (dd, J = 8.4, 1.8 Hz, 1H), 6.68 (s, 1H), 4.99 (dd, J = 13.3, 5.0 Hz, 1H), 4.50 (d, J = 5.7 Hz, 2H), 4.23 (d, J = 16.8 Hz, 1H), 4.09 (d, J = 16.7 Hz, 1H), 3.85 (s, 3H), 2.92-2.83 (m, 1H), 2.60-2.51 (m, 1H), 2.34-2.25 (m, 1H), 1.95-1.88 (m, 1H). $^{13}$C NMR (101 MHz, DMSO-$d_6$) δ 172.93, 171.38, 168.60, 157.45, 152.08, 144.33, 137.63, 134.31, 129.04, 127.78, 127.59, 124.04, 123.95, 123.25, 119.18, 118.11, 112.68, 105.80, 104.76, 55.16, 51.26, 46.74, 46.33, 31.25, 22.61. HRMS-ESI (m/z): $[M + H]^+$ calculated for $C_{25}H_{24}N_3O_4$, 430.1761; found, 430.1761. |
| DEG-17 | 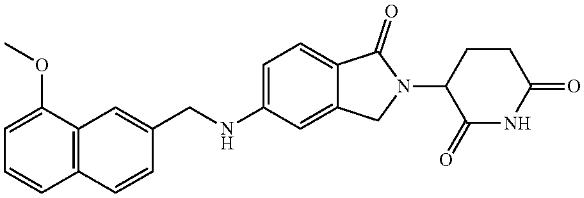 3-(5-(((8-methoxynaphthalen-2-yl)methyl)amino)-1-oxoisoindolin-2-yl)piperidine-2,6-dione | $^1$H NMR (400 MHz, DMSO-$d_6$) δ 10.89 (s, 1H), 8.12 (s, 1H), 7.84 (d, J = 8.4 Hz, 1H), 7.52 (dd, J = 8.4, 1.5 Hz, 1H), 7.44 (d, J = 8.2 Hz, 1H), 7.42-7.32 (m, 2H), 7.13 (t, J = 6.0 Hz, 1H), 6.95 (d, J = 7.2 Hz, 1H), 6.72 (dd, J = 8.4, 1.8 Hz, 1H), 6.67 (s, 1H), 4.98 (dd, J = 13.2, 5.0 Hz, 1H), 4.53 (d, J = 6.0 Hz, 2H), 4.22 (d, J = 16.8 Hz, 1H), 4.09 (d, J = 16.8 Hz, 1H), 2.86 (ddd, 17.6, 13.6, 5.4, 1H), 2.59-2.52 (m, 1H), 2.30 (qd, J = 13.3, 4.4 Hz, 1H), 1.94-1.86 (m, 1H). $^{13}$C NMR (101 MHz, DMSO-$d_6$) δ 172.95, 171.38, 168.59, 154.56, 152.05, 144.33, 136.63, 133.17, |

-continued

| | Compound structure | Characterization |
|---|---|---|
| | | 127.75, 126.13, 125.81, 124.77, 123.94, 119.76, 119.20, 118.97, 112.74, 104.81, 104.56, 55.45, 51.25, 46.73, 46.48, 31.25, 22.61. HRMS-ESI (m/z): $[M + H]^+$ calculated for $C_{25}H_{24}N_3O_4$, 430.1761; found, 430.1763. |
| DEG-18 | 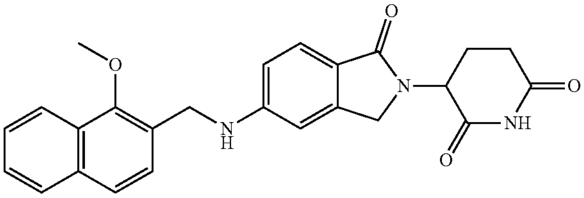 3-(5-(((1-methoxynaphthalen-2-yl)methyl)amino)-1-oxoisoindolin-2-yl)piperidine-2,6-dione | $^1H$ NMR (400 MHz, DMSO-$d_6$) δ 10.90 (s, 1H), 8.08 (d, J = 8.2 Hz, 1H), 7.90 (d, J = 8.0 Hz, 1H), 7.67 (d, J = 8.5 Hz, 1H), 7.61-7.45 (m, 3H), 7.38 (d, J = 8.4 Hz, 1H), 7.01 (t, J = 5.8 Hz, 1H), 6.73 (d, J = 9.4 Hz, 1H), 6.70 (s, 1H), 4.99 (dd, J = 13.3, 4.8 Hz, 1H), 4.54 (d, J = 5.7 Hz, 2H), 4.24 (d, J = 16.8 Hz, 1H), 4.10 (d, J = 16.8 Hz, 1H), 3.95 (s, 3H), 2.86 (ddd, J = 18.2, 14.0, 5.3 Hz, 1H), 2.60-2.52 (m, 1H), 2.39-2.22 (m, 1H), 1.98-1.85 (m, 1H). $^{13}C$ NMR (101 MHz, DMSO-$d_6$) δ 172.96, 171.40, 168.60, 153.20, 152.04, 144.40, 133.84, 127.98, 127.48, 127.34, 126.33, 126.22, 126.01, 123.96, 123.93, 121.61, 119.24, 112.60, 104.59, 62.19, 51.26, 46.75, 40.73, 31.26, 22.61. HRMS-ESI (m/z): $[M + H]^+$ calculated for $C_{25}H_{24}N_3O_4$, 430.1761; found, 430.1764. |
| DEG-19 | 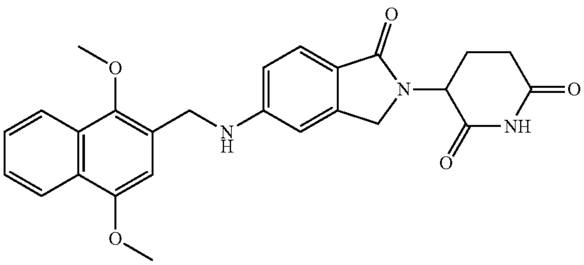 3-(5-(((1,4-dimethoxynaphthalen-2-yl)methyl)amino)-1-oxoisoindolin-2-yl)piperidine-2,6-dione | $^1H$ NMR (400 MHz, DMSO-$d_6$) δ 10.91 (s, 1H), 8.11 (d, J = 8.3 Hz, 1H), 8.02 (d, J = 8.3 Hz, 1H), 7.59 (t, J = 7.5 Hz, 1H), 7.50 (t, J = 7.5 Hz, 1H), 7.39 (d, J = 8.3 Hz, 1H), 6.80-6.93 (m, 2H), 6.77-6.73 (m, 2H), 4.99 (dd, J = 13.12, 4.8 Hz, 1H), 4.50 (d, J = 3.8 Hz, 2H), 4.45 (d, J = 16.9 Hz, 1H), 4.11 (d, J = 16.6 Hz, 1H), 3.88 (s, 6H), 2.93-2.82 (m, 1H), 2.60-2.53 (m, 1H), 2.37-2.25 (m, 1H), 1.94-1.87 (m, 1H). $^{13}C$ NMR (101 MHz, DMSO) δ 172.94, 171.38, 168.62, 152.09, 151.26, 146.66, 144.37, 127.92, 127.20, 126.80, 125.45, 125.18, 123.94, 121.86, 121.64, 119.31, 112.69, 104.67, 104.40, 62.32, 55.64, 51.27, 46.76, 41.13, 31.26, 22.61. HRMS-ESI (m/z): $[M + H]^+$ calculated for $C_{26}H_{26}N_3O_5$, 460.1867; found, 460.1870. |
| DEG-20 | 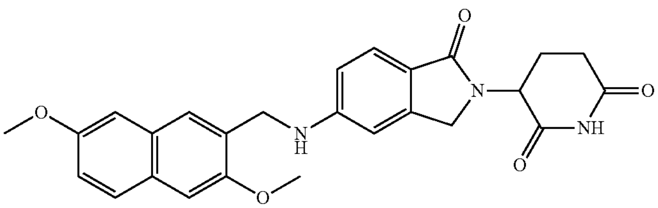 3-(5-(((3,7-dimethoxynaphthalen-2-yl)methyl)amino)-1-oxoisoindolin-2-yl)piperidine-2,6-dione | $^1H$ NMR (400 MHz, DMF-$d_7$) δ 10.86 (s, 1H), 7.78 (m, 2H), 7.49 (d, J = 8.4 Hz, 1H), 7.37 (s, 1H), 7.23 (d, J = 2.4 Hz, 1H), 7.12 (dd, J = 8.8, 2.5 Hz, 1H), 6.93-6.84 (m, 2H), 6.80 (s, 1H), 5.14 (dd, J = 13.3, 5.1 Hz, 1H), 4.56 (d, J = 5.8 Hz, 2H), 4.32 (d, J = 16.6 Hz, 1H), 4.24 (d, J = 16.6 Hz, 1H), 3.99 (s, 3H), 3.86 (s, 3H), 3.04-2.97 (m, 1H), 2.73-2.67 (m, 1H), 2.45 (qd, J = 13.4, 4.3 Hz, 1H), 2.12-1.96 (m, 1H). $^{13}C$ NMR (101 MHz, DMF-$d_7$) δ 173.08, 171.70, 169.34, 156.63, 154.80, 153.03, 145.11, 129.90, 129.41, 129.39, 128.23, 125.90, 124.32, 120.11, 118.57, 113.20, 106.29, 105.80, 105.13, 55.48, 55.20, 52.03, 47.23, 31.82, 42.57, 23.40. HRMS-ESI (m/z): $[M + H]^+$ calculated for $C_{26}H_{26}N_3O_5$, 460.1867; found, 460.1868. |

-continued

| | Compound structure | Characterization |
|---|---|---|
| DEG-21 | 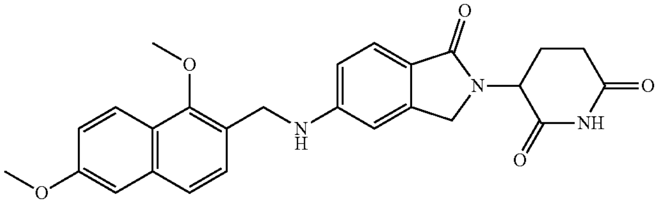 3-(5-(((1,6-dimethoxynaphthalen-2-yl)methyl)amino)-1-oxoisoindolin-2-yl)piperidine-2,6-dione | $^1$H NMR (400 MHz, DMF-$d_7$) δ 8.05 (d, J = 9.2 Hz, 1H), 7.61 (d, J = 8.5 Hz, 1H), 7.53 (d, J = 8.5 Hz, 1H), 7.46 (d, J = 8.3 Hz, 1H), 7.38 (d, J = 2.4 Hz, 1H), 7.24 (dd, J = 9.1, 2.5 Hz, 1H), 6.92-6.82 (m, 3H), 5.13 (dd, J = 13.3, 5.1 Hz, 1H), 4.61 (d, J = 5.7 Hz, 2H), 4.33 (d, J = 16.5 Hz, 1H), 4.24 (d, J = 16.5 Hz, 1H), 3.05-2.95 (m, 1H), 2.73-2.67 (m, 1H), 2.52-2.42 (m, 1H), 2.12-2.06 (m, 1H). $^{13}$C NMR (101 MHz, DMF-$d_7$) δ 172.90, 171.54, 169.13, 158.08, 154.15, 152.73, 144.92, 136.08, 127.50, 125.38, 124.08, 123.64, 123.23, 123.14, 119.98, 118.78, 113.04, 106.51, 104.93, 62.25, 55.16, 51.87, 47.07, 41.37, 31.65, 23.23. HRMS-ESI (m/z): [M + H]$^+$ calculated for $C_{26}H_{26}N_3O_5$, 460.1867; found, 460.1870. |
| DEG-22 | 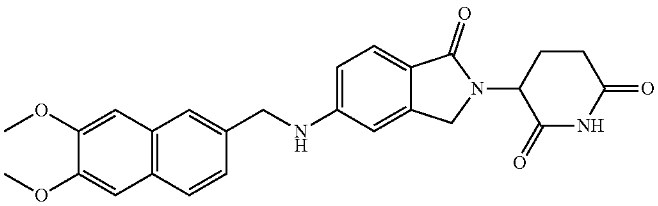 3-(5-(((6,7-dimethoxynaphthalen-2-yl)methyl)amino)-1-oxoisoindolin-2-yl)piperidine-2,6-dione | $^1$H NMR (400 MHz, DMF-$d_7$) δ 10.87 (s, 1H), 7.79-7.73 (m, 2H), 7.47 (d, J = 8.1 Hz, 1H), 7.40 (d, J = 8.1 Hz, 1H), 7.33 (d, J = 18.2 Hz, 1H), 7.02-6.96 (m, 1H), 6.90-6.85 (m, 1H), 6.82 (s, 1H), 5.17-5.10 (m, 1H), 4.57 (s, 2H), 4.31 (d, J = 17.3 Hz, 1H), 4.23 (d, J = 16.0 Hz, 1H), 3.04-2.88 (m, 1H) 2.79-2.66 (m, 1H), 2.51-2.39 (m, 1H), 2.11-2.01 (m, 1H). $^{13}$C NMR (101 MHz, DMF-$d_7$) δ 173.08, 171.70, 169.34, 152.95, 150.34, 149.96, 145.04, 135.52, 129.66, 128.76, 126.87, 124.62, 124.26, 124.12, 120.09, 113.32, 106.78, 106.72, 105.27, 55.54 (2 × $CH_3$), 52.03, 47.31, 47.22, 31.81, 23.38. HRMS-ESI (m/z): [M + H]$^+$ calculated for $C_{26}H_{26}N_3O_5$, 460.1867; found, 460.1869. |
| DEG-23 | 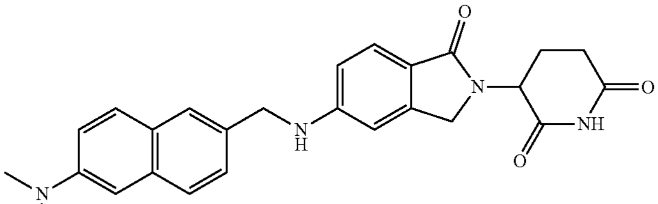 3-(5-(((6-(dimethylamino)naphthalen-2-yl)methyl)amino)-1-oxoisoindolin-2-yl)piperidine-2,6-dione | $^1$H NMR (400 MHz, DMF-$d_7$) δ 10.86 (s, 1H), 7.76-7.68 (m, 3H), 7.47-7.42 (m, 2H), 7.26 (dd, J = 9.1, 2.5 Hz, 1H), 7.01 (d, J = 2.4 Hz, 1H), 6.95 (t, J = 5.8 Hz, 1H), 6.87 (dd, J = 8.4, 2.0 Hz, 1H), 6.82 (s, 1H), 5.12 (dd, J = 13.3, 5.1 Hz, 1H), 4.53 (d, J = 5.7 Hz, 2H), 4.32 (d, J = 16.6 Hz, 1H), 4.23 (d, J = 16.5 Hz, 1H), 3.03 (s, 6H), 3.01-2.95 (m, 1H), 2.73-2.67 (m, 1H), 2.52-2.40 (m, 1H), 2.11-2.05 (m, 1H). $^{13}$C NMR (101 MHz, DMF-$d_7$) δ 173.08, 171.72, 169.33, 152.98, 149.09, 145.04, 134.71, 133.15, 128.62, 126.99, 126.73, 126.43, 125.77, 124.22, 120.07, 116.93, 113.35, 106.39, 105.28, 52.04, 47.31, 47.24, 40.38 (2 × $CH_3$), 31.83, 23.41. HRMS-ESI (m/z): [M + H]$^+$ calculated for $C_{26}H_{27}N_4O_3$, 443.2078; found, 443.2078. |
| DEG-24 | 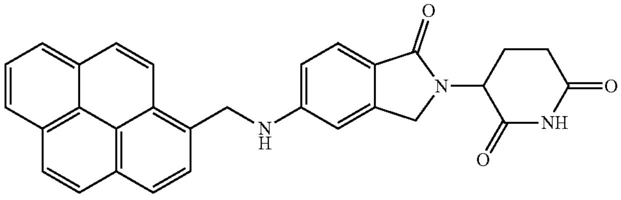 3-(5-(((5a$^1$,10-dihydropyren-1-yl)methyl)amino)-1-oxoisoindolin-2-yl)piperidine-2,6-dione | $^1$H NMR (400 MHz, DMF-$d_7$) δ 10.87 (s, 1H), 8.49 (d, J = 9.3 Hz, 1H), 8.38-8.34 (m, 2H), 8.31 (s, 1H), 8.29 (s, 1H), 8.22-8.18 (m, 3H), 8.12 (t, J = 7.64 Hz, 1H), 7.51 (d, J = 8.4 Hz, 1H), 7.06 (t, J = 4.9 Hz, 1H), 6.98-6.92 (m, 2H), 5.17 (d, J = 5.3 Hz, 2H), 5.13 (d, J = 5.24 Hz, 1H), 4.34 (d, J = 16.6 Hz, 1H), 4.25 (d, J = 16.6 Hz, 1H), 3.05-2.96 (m, 1H), 2.73-2.68 (m, 1H), 2.51-2.40 (m, 1H), 2.13-2.07 (m, 1H). $^{13}$C NMR (101 MHz, DMF-$d_7$) δ 173.10, 171.73, 169.38, 153.01, 145.20, 133.14, 131.64, 131.18, 131.03, 129.16, 127.97, 127.87, 127.48, 126.77, 126.61, 125.66, 125.61, 125.20, 125.00, 124.78, 124.36, 123.64, 120.27, 113.34, 105.26, 52.08, 47.30, 45.64, 31.84, 23.42. HRMS-ESI (m/z): [M + H]$^+$ calculated for $C_{30}H_{24}N_3O_3$, 474.1812; found, 474.1813. |

-continued

| | Compound structure | Characterization |
|---|---|---|
| DEG-25 | 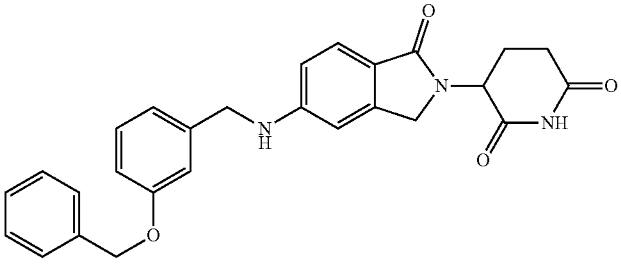 3-(5-((3-(benzyloxy)benzyl)amino)-1-oxoisoindolin-2-yl)piperidine-2,6-dione | $^1$H NMR (400 MHz, DMSO-$d_6$) δ 10.90 (s, 1H), 7.43-7.29 (m, 6H), 7.24 (t, J = 7.9 Hz, 1H), 7.01-6.87 (m, 4H), 6.69 (d, J = 9.7 Hz, 1H), 6.63 (s, 1H), 5.07 (s, 2H), 5.00 (dd, J = 13.3, 5.1 Hz, 1H), 4.32 (d, J = 5.9 Hz, 2H), 4.23 (d, J = 16.8 Hz, 1H), 4.10 (d, J = 16.8 Hz, 1H), 2.93-2.84 (m, 1H), 2.59-2.55 (m, 1H), 2.87-2.26 (m, 1H), 1.94-1.91 (m, 1H). $^{13}$C NMR(101 MHz, DMSO-$d_6$) δ 172.94, 171.39, 168.62, 158.51, 152.02, 144.30, 141.30, 137.05, 129.47, 128.39, 127.78, 127.68, 123.91, 119.50, 119.20, 113.69, 112.88, 112.69, 104.74, 69.08, 51.26, 46.74, 46.00, 31.26, 22.61. HRMS-ESI (m/z): $[M + H]^+$ calculated for $C_{27}H_{26}N_3O_4$, 456.1918; found, 456.1919. |
| DEG-26 | 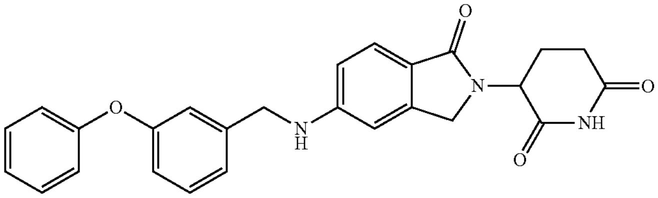 3-(1-oxo-5-((3-phenoxybenzyl)amino)isoindolin-2-yl)piperidine-2,6-dione | $^1$H NMR (400 MHz, DMF-$d_7$) δ 10.87 (s, 1H), 7.45 (d, J = 8.3 Hz, 1H), 7.42-7.37 (m, 3H), 7.24 (d, J = 7.6 Hz, 1H), 7.17-7.13 (m, 2H), 7.04-6.96 (m, 3H), 6.91 (dd, J = 8.1, 2.3 Hz, 1H), 6.81 (dd, J = 8.36, 1.8 Hz, 1H), 6.77 (s, 1H), 5.15 (dd, J = 13.3, 5.1 Hz, 1H), 4.49 (d, J = 6.0 Hz, 2H), 4.33 (d, J = 16.5 Hz, 1H), 4.25 (d, J = 16.5 Hz, 1H), 3.06-2.95 (m, 1H), 2.73-2.68 (m, 1H), 2.54-2.42 (m, 1H), 2.14-2.07 (m, 1H). $^{13}$C NMR (101 MHz, DMF-$d_7$) δ 173.10, 171.73, 169.30, 157.57, 157.51, 152.70, 145.03, 142.71, 130.30, 124.28, 123.65, 122.68, 120.32, 118.87, 117.98, 117.43, 113.35, 105.46, 52.07, 49.16, 47.25, 46.64, 31.85, 23.43. HRMS-ESI (m/z): $[M + H]^+$ calculated for $C_{26}H_{24}N_3O_4$, 442.1761; found, 442.1763. |
| DEG-27 | 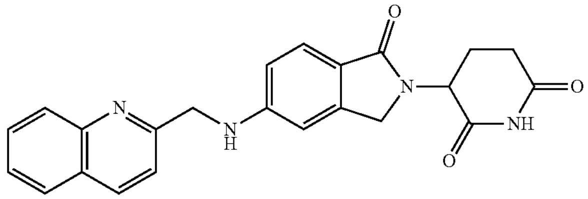 3-(1-oxo-5-((quinolin-2-yl)methyl)amino)isoindolin-2-yl)piperidine-2,6-dione | $^1$H NMR (400 MHz, DMF-$d_7$) δ 10.86 (s, 1H), 8.37 (d, J = 8.5 Hz, 1H), 8.05 (t, J = 7.4 Hz, 1H), 7.99 (d, J = 8.2 Hz, 1H), 7.83-7.78 (m, 1H), 7.65-7.59 (m, 2H), 7.48 (d, J = 8.3 Hz, 1H), 7.20 (t, J = 5.8 Hz, 1H), 6.91 (dd, J = 8.4, 2.0 Hz, 1H), 6.86 (s, 1H), 5.13 (dd, J = 13.3, 5.1 Hz, 1H), 4.74 (d, J = 5.5 Hz, 2H), 4.34 (d, J = 16.6 Hz, 1H), 4.24 (d, J = 16.6 Hz, 1H), 3.05-2.95 (m, 1H), 2.73-2.66 (m, 1H), 2.52-2.41 (m, 1H), 2.13-2. 05 (m, 1H). $^{13}$C NMR (101 MHz, DMF-$d_7$) δ 173.07, 171.69, 169.24, 160.30, 152.64, 147.93, 145.11, 137.06, 129.94, 129.02, 128.26, 126.54, 124.34, 120.53, 120.02, 113.42, 105.47, 52.06, 49.64, 47.25, 31.82, 23.40. HRMS-ESI (m/z): $[M + H]^+$ calculated for $C_{23}H_{21}N_4O_3$, 401.1608; found, 401.1607. |
| DEG-28 | 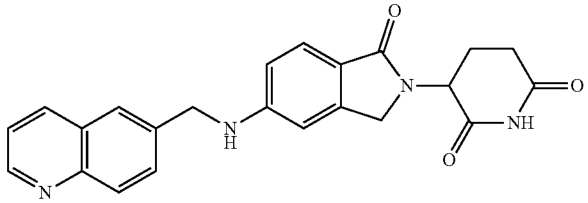 3-(1-oxo-5-((quinolin-6-yl)methyl)amino)isoindolin-2-yl)piperidine-2,6-dione | $^1$H NMR (400 MHz, DMSO-$d_6$) δ 10.90 (s, 1H), 8.85 (dd, J = 4.1, 1.5 Hz, 1H), 8.32 (d, J = 8.1 Hz, 1H), 8.00 (d, J = 8.7 Hz, 1H), 7.90 (s, 1H), 7.76 (dd, J = 8.7, 1.7 Hz, 1H), 7.50 (dd, J = 8.3, 4.2 Hz, 1H), 7.39 (d, J = 8.3 Hz, 1H), 7.15 (t, J = 6.0 Hz, 1H), 6.73 (dd, J = 8.2, 1.5 Hz, 2H), 6.70 (s, 1H) 4.99 (dd, J = 13.3, 5.0 Hz, 1H), 4.57 (d, J = 5.8 Hz, 2H), 4.23 (d, J = 16.8 Hz, 2H), 4.10 (d, J = 16.8 Hz), 2.87 (ddd, J = 18.2, 13.7, 5.3 Hz, 1H), 2.61-2.53 (m, 1H), 2.29 (qd, J = 13.2, 4.5 Hz, 1H), 1.98-1.81 (m, 1H). $^{13}$C NMR (101 MHz, DMSO-$d_6$) δ 172.92, 171.37, 168.57, 151.95, 150.13, 147.11, 144.36, 137.95, 135.73, 129.19, 129.12, 127.75, 125.27, 123.98, 121.59, 119.37, 112.75, 104.86, 51.26, 46.74, 46.03, 31.25, 22.60. HRMS-ESI (m/z): $[M + H]^+$ calculated for $C_{23}H_{21}N_4O_3$, 401.1608; found, 401.1607. |

-continued

| | Compound structure | Characterization |
|---|---|---|
| DEG-29 | 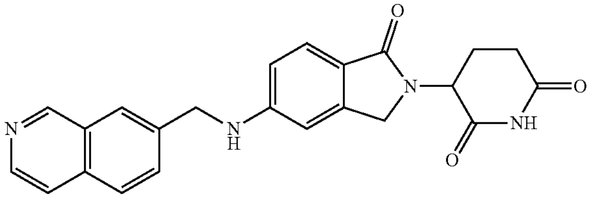 3-(5-((isoquinolin-7-ylmethyl)amino)-1-oxoisoindolin-2-yl)piperidine-2,6-dione | $^1$H NMR (400 MHz, DMSO-$d_6$) δ 10.90 (s, 1H), 9.63 (s, 1H), 8.41 (d, J = 6.5 Hz, 1H), 8.38 (s, 1H), 8.30 (d, J = 6.5 Hz, 1H), 8.23 (d, J = 4.5 H, 1H), 8.09 (d, J = 8.6 Hz, 1H), 7.40 (d, J = 8.3 Hz, 1H), 7.23 (t, J = 6.0 Hz, 1H), 6.73 (dd, J = 8.4, 1.8 Hz, 1H), 6.52 (s, 1H), 4.99 (dd, J = 13.2, 5.1 Hz, 1H), 4.64 (d, J = 5.9 Hz, 2H), 4.22 (d, J = 16.8 Hz, 1H), 4.09 (d, J = 16.7 Hz, 1H), 2.94-2.80 (m, 1H), 2.59-2.53 (m, 1H), 2.34-2.25 (m, 1H), 1.95-1.88 (m, 1H). HRMS-ESI (m/z): $[M + H]^+$ calculated for $C_{23}H_{21}N_4O_3$, 401.1608; found, 401.1608. |
| DEG-30 | 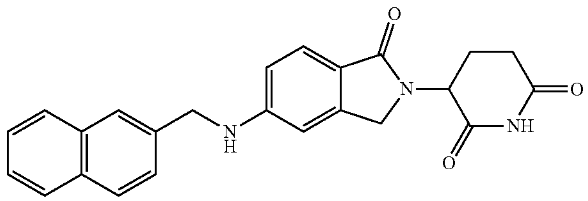 3-(5-((isoquinolin-3-ylmethyl)amino)-1-oxoisoindolin-2-yl)piperidine-2,6-dione | $^1$H NMR (400 MHz, DMSO-$d_6$) δ 10.90 (s, 1H), 9.32 (s, 1H), 8.11 (d, J = 8.0 Hz, 1H), 7.90 (d, J = 8.2 Hz, 1H), 7.75-7.71 (m, 2H), 7.66-7.61 (m, 1H), 7.40 (d, J = 8.4 Hz, 1H), 7.17 (t, J = 6.0 Hz, 1H), 6.75 (dd, J = 8.4, 1.9 Hz, 1H), 6.70 (s, 1H), 4.99 (dd, J = 13.2,5.1 Hz, 1H), 4.61 (d, J = 6.0 Hz, 2H), 4.23 (d, J = 16.9 Hz, 1H), 4.10 (d, J = 16.8 Hz, 1H), 2.92-2.83 (m, 1H), 2.58-2.52 (m, 1H), 2.35-2.24 (m, 1H), 1.94-1.87 (m, 1H). $^{13}$C NMR (101 MHz, DMSO-$d_6$) δ 173.41, 171.86, 169.06, 152.90, 152.73, 152.45, 144.87, 136.19, 131.22, 128.04, 127.76, 127.50, 126.85, 124.47, 119.84, 116.86, 113.24, 105.30, 51.74, 48.67, 47.23, 31.74, 23.09. HRMS-ESI (m/z): $[M + H]^+$ calculated for $C_{23}H_{21}N_4O_3$, 401.1608; found, 401.1606. |
| DEG-31 | 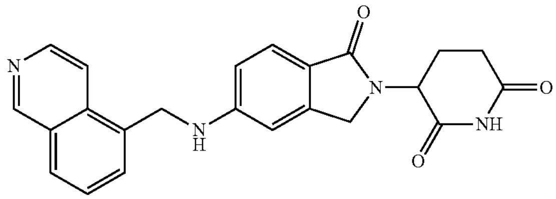 3-(5-((isoquinolin-5-ylmethyl)amino)-1-oxoisoindolin-2-yl)piperidine-2,6-dione | $^1$H NMR (400 MHz, DMSO-$d_6$) δ 10.87 (s, 1H), 9.31 (s, 1H), 8.53 (d, J = 6.0 Hz, 1H), 8.01 (d, J = 8.2 Hz, 1H), 7.97 (d, J = 6.0 Hz, 1H), 7.71 (d, J = 7.0 Hz, 1H), 7.60 (t, J = 7.6 Hz, 1H), 7.37 (d, J = 8.3 Hz, 1H), 7.01 (t, J = 5.6 Hz, 1H), 6.71 (dd, J = 8.3, 1.8 Hz, 1H), 6.69 (s, 1H), 4.96 (dd, J = 13.2, 5.0 Hz, 1H), 4.77 (d, J = 5.5 Hz, 2H), 4.21 (d, J = 16.8 Hz, 1H), 4.07 (d, J = 16.8 Hz, 1H), 2.84 (ddd, J = 18.2, 13.7, 5.4 Hz, 1H), 2.58-2.49 (m, 1H), 2.27 (qd, J = 13.4, 4.4 Hz, 1H), 2.01-1.82 (m, 1H). $^{13}$C NMR (101 MHz, DMSO-$d_6$) δ 172.93, 171.38, 168.60, 152.89, 151.98, 144.43, 143.07, 133.92, 133.60, 128.93, 128.55, 127.04, 126.97, 124.00, 119.37, 116.67, 112.69, 104.74, 51.28, 46.78, 43.60, 31.26, 22.61. HRMS-ESI (m/z): $[M + H]^+$ calculated for $C_{23}H_{21}N_4O_3$, 401.1608; found, 401.1604. |
| DEG-32 | 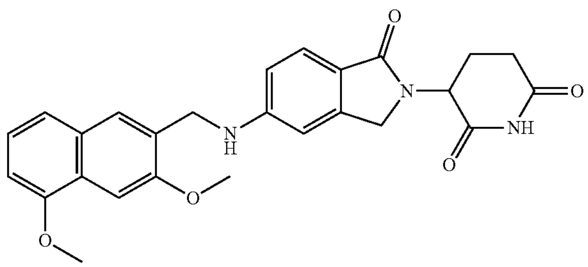 3-(5-(((3,5-dimethoxynaphthalen-2-yl)methyl)amino)-1-oxoisoindolin-2-yl)piperidine-2,6-dione | $^1$H NMR (400 MHz, DMSO-$d_6$) δ 10.90 (s, 1H), 7.66 (s, 1H), 7.48 (s, 1H), 7.40 (d, J = 8.4 Hz, 1H), 7.31 (d, J = 8.2 Hz, 1H), 7.23 (t, J = 7.9 Hz, 1H), 6.96-6.89 (m, 2H), 6.72 (dd, J = 8.4, 1.8 Hz, 1H), 6.65 (s, 1H), 4.99 (dd, J = 13.3, 5.1 Hz, 1H), 4.45 (d, J = 5.8 Hz, 2H), 4.23 (d, J = 16.8 Hz, 1H), 4.10 (d, J = 16.8 Hz, 1H), 3.96 (s, 6H), 2.92-2.82 (m, 1H), 2.59-2.51 (m, 1H), 2.34-2.23 (m, 1H), 1.94-1.88 (m, 1H). $^{13}$C NMR (101 MHz, DMSO-$d_6$) δ 172.94, 171.40, 168.61, 155.29, 153.81, 152.14, 144.42, 128.93, 128.73, 126.06, 124.79, 123.99, 123.83, 119.56, 119.21, 112.65, 104.60, 104.48, 99.25, 55.46, 55.43, 51.26, 46.75, 31.26, 30.69, 22.64. HRMS-ESI (m/z): $[M + H]^+$ calculated for $C_{26}H_{26}N_3O_5$, 460.1867; found, 460.1865. |

-continued

| | Compound structure | Characterization |
|---|---|---|
| DEG-33 | 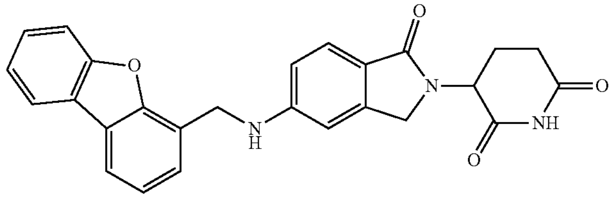 3-(5-((dibenzo[b,d]furan-4-ylmethyl)amino)-1-oxoisoindolin-2-yl)piperidine-2,6-dione | $^1$H NMR (500 MHz, DMSO-$d_6$) δ 10.90 (s, 1H), 8.16 (d, J = 7.7 Hz, 1H), 8.05 (d, J = 7.5 Hz, 1H), 7.77 (d, J = 8.3 Hz, 1H), 7.55 (t, J = 7.8 Hz, 1H), 7.47 (d, J = 7.5 Hz, 1H), 7.39 (m, 3H), 7.08 (t, J = 5.8 Hz, 1H), 6.77 (d, J = 9.1 Hz, 1H), 6.74 (s, 1H), 5.00 (dd, J = 13.2, 5.1 Hz, 1H), 4.73 (d, J = 5.7 Hz, 2H), 4.24 (d, J = 16.8 Hz, 1H), 4.11 (d, J = 16.8 Hz, 1H), 2.88 (ddd, J = 18.2, 14.2, 5.4 Hz, 1H), 2.61-2.53 (m, 1H), 2.30 (qd, J = 13.0, 4.4 Hz, 1H), 1.99-1.86 (m, 1H). $^{13}$C NMR (126 MHz, DMSO-$d_6$) δ 172.91, 171.37, 168.59, 155.43, 153.45, 151.97, 144.41, 127.60, 126.13, 123.97, 123.68, 123.50, 123.17, 123.14, 123.05, 121.23, 119.78, 119.40, 112.71, 111.78, 104.72, 51.27, 46.77, 40.91, 31.25, 22.61. HRMS-ESI (m/z): [M + H]$^+$ calculated for $C_{26}H_{22}N_3O_4$, 440.1605; found, 440.1603. |
| DEG-34 | 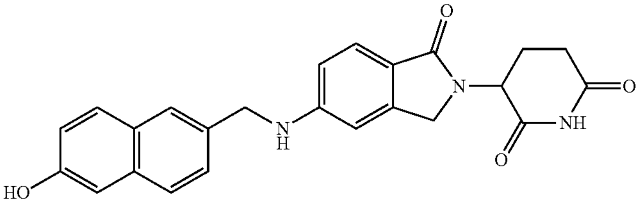 3-(5-(((6-hydroxynaphthalen-2-yl)methyl)amino)-1-oxoisoindolin-2-yl)piperidine-2,6-dione | $^1$H NMR (400 MHz, DMSO-$d_6$) δ 10.90 (s, 1H), 9.70 (bs, 1H), 7.72-7.63 (m, 3H), 7.30-7.36 (m, 2H), 7.10-7.01 (m, 3H), 6.72 (dd, J = 8.4, 1.9 Hz, 1H), 6.69 (s, 1H), 4.99 (dd, J = 13.2, 5.1 Hz, 1H), 4.44 (d, J = 5.8 Hz, 2H), 4.23 (d, J = 16.7 Hz, 1H), 4.10 (d, J = 16.9 Hz, 1H), 2.93-2.83 (m, 1H), 2.60-2.52 (m, 1H), 2.38-2.24 (m, 1H), 1.94-1.88 (m, 1H). $^{13}$C NMR (101 MHz, DMSO-$d_6$) δ 172.94, 171.39, 168.62, 155.11, 152.12, 144.33, 133.74, 133.52, 129.02, 127.56, 126.28, 126.02, 125.25, 123.91, 119.11, 118.73, 108.59, 104.75, 51.26, 46.75, 46.30, 31.26, 30.70, 22.62. HRMS-ESI (m/z): [M + H]$^+$ calculated for $C_{24}H_{22}N_3O_4$, 416.1605; found, 416.1599. |
| DEG-35 | 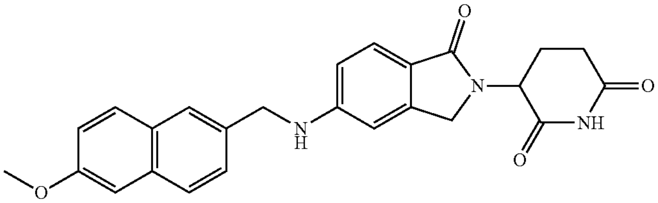 N-(2-(2,6-dioxopiperidin-3-yl)-1-oxoisoindolin-5-yl)-6-methoxy-2-naphthamide | $^1$H NMR (400 MHz, DMSO-$d_6$) δ 10.99 (s, 1H), 10.65 (s, 1H), 8.55 (s, 1H), 8.19 (s, 1H), 8.02-7.94 (m, 3H), 7.89 (d, J = 9.7 Hz, 1H), 7.73 (d, J = 8.3 Hz, 1H), 7.43 (d, J = 2.3 Hz, 1H), 7.27 (dd, J = 8.94, 2.46 Hz, 1H), 5.11 (dd, J = 13.24,5.08 Hz, 1H), 4.49 (d, J = 17.3 Hz, 1H), 4.35 (d, J = 17.3 Hz, 1H), 3.92 (s, 3H), 2.98-2.87 (m, 1H), 2.61 (d, J = 16.4 Hz, 1H), 2.46-2.31 (m, 1H), 2.05-1.98 (m, 1H). $^{13}$C NMR (101 MHz, DMSO-$d_6$) δ 172.90, 171.12, 167.85, 166.03, 158.83, 143.13, 142.64, 136.11, 130.61, 129.58, 128.12, 127.36, 126.87, 126.64, 124.99, 123.52, 119.88, 119.57, 114.32, 105.96, 55.38, 51.56, 47.18, 31.23, 22.54. HRMS-ESI (m/z): [M + H]$^+$ calculated for $C_{25}H_{22}N_3O_5$, 444.1554; found, 444.1554. |
| DEG-36 | 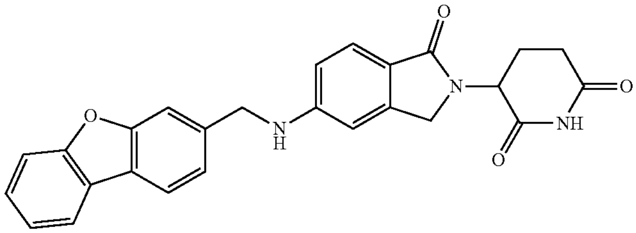 3-(5-((dibenzo[b,d]furan-3-ylmethyl)amino)-1-oxoisoindolin-2-yl)piperidine-2,6-dione | $^1$H NMR (500 MHz, DMSO-$d_6$) δ 10.90 (s, 1H), 8.12-8.08 (m, 2H), 7.68 (s, 1H), 7.67 (s, 1H), 7.50 (t, J = 6.2 Hz, 1H), 7.44-7.37 (m, 3H), 7.13 (t, J = 4.7 Hz, 1H), 6.74 (d, J = 6.7 Hz, 1H), 6.70 (s, 1H), 4.99 (dd, J = 10.6, 4.0 Hz, 1H), 4.55 (d, J = 4.6 Hz, 2H), 4.24 (d, J = 13.4 Hz, 1H), 4.11 (d, J = 13.4 Hz, 1H), 2.92-2.83 (m, 1H), 2.60-2.53 (m, 1H), 2.36-2.27 (m, 1H), 1.94-1.88 (m, 1H). $^{13}$C NMR (126 MHz, DMSO-$d_6$) δ 172.92, 171.35, 168.57, 155.76, 155.58, 151.92, 144.35, 140.00, 127.31, 123.94, 123.47, 123.08, 122.31, 122.28, 121.00, 120.96, 119.35, 112.83, 111.61, 110.08, 104.91, 51.26, 46.74, 46.26, 31.25, 22.60. HRMS-ESI (m/z): [M + H]$^+$ calculated for $C_{26}H_{22}N_3O_4$, 440.1605; found, 440.1602. |

-continued

| | Compound structure | Characterization |
|---|---|---|
| DEG-37 | 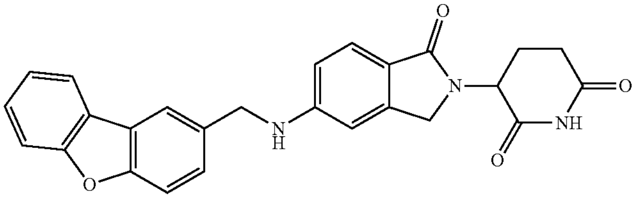 3-(5-((dibenzo[b,d]furan-3-ylmethyl)amino)-1-oxoisoindolin-2-yl)piperidine-2,6-dione | $^1$H NMR (400 MHz, DMSO-d$_6$) δ 10.90 (s, 1H), 8.13 (s, 1H), 8.11 (s, 1H), 7.68 (t, J = 7.8 Hz, 2H), 7.54-7.49 (m, 2H), 7.41-7.36 (m, 2H), 7.08 (t, J = 5.8 Hz, 1H), 6.75 (d, J = 8.3 Hz, 1H), 6.72 (s, 1H), 4.99 (dd, J = 13.2, 5.0 Hz, 1H), 4.51 (d, J = 5.7 Hz, 2H), 4.24 (d, J = 16.8 Hz, 1H), 4.11 (d, J = 16.9 Hz, 1H), 2.92-2.83 (m, 1H), 2.59-2.52 (m, 1H), 2.36-2.24 (m, 1H), 1.94-1.88 (m, 1H). $^{13}$C NMR (101 MHz, DMSO-d$_6$) δ 172.93, 171.38, 168.61, 155.78, 154.61, 152.01, 144.36, 134.46, 127.59, 126.91, 123.94, 123.60, 123.43, 123.09, 121.09, 119.66, 119.26, 112.80, 111.68, 111.51, 104.83, 51.26, 46.76, 46.26, 31.25, 22.61. HRMS-ESI (m/z): [M + H]$^+$ calculated for $C_{26}H_{22}N_3O_4$, 440.1605; found, 440.1602. |
| DEG-38 | 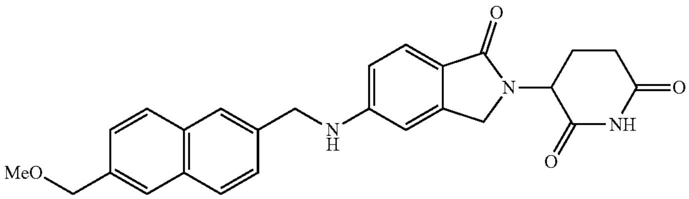 3-(5-(((6-methoxymethyl)naphthalen-2-yl)methyl)amino)-1-oxoisoindolin-2-yl)piperidine-2,6-dione | $^1$H NMR (400 MHz, DMSO-d$_6$) δ 10.90 (s, 1H), 7.90-7.80 (m, 4H), 7.51 (d, J = 7.5 Hz, 1H), 7.43 (d, J = 8.8 Hz, 1H), 7.38 (d, J = 8.4 Hz, 1H), 7.11 (t, J = 5.9 Hz, 1H), 6.73 (d, J = 8.0 Hz, 1H), 6.70 (s, 1H), 4.99 (dd, J = 13.3, 5.1 Hz, 1H), 4.56 (s, 2H), 4.52 (d, J = 5.8 Hz, 2H), 4.23 (d, J = 16.9 Hz, 1H), 4.09 (d, J = 16.8 Hz, 1H), 3.32 (s, 3H), 2.92-2.82 (m, 1H), 2.60-2.52 (m, 1H), 2.35-2.23 (m, 1H), 1.94-1.87 (m, 1H). $^{13}$C NMR (101 MHz, DMSO-d$_6$) δ 172.92, 171.37, 168.59, 152.05, 144.34, 137.13, 135.58, 132.38, 131.98, 127.99, 127.60, 126.01, 125.96, 125.79, 125.05, 123.94, 119.23, 112.74, 104.81, 73.64, 57.53, 51.25, 46.74, 46.29, 31.25, 22.61. HRMS-ESI (m/z): [M + H]$^+$ calculated for $C_{26}H_{26}N_3O_4$, 444.1918; found, 444.1919. |
| DEG-39 | 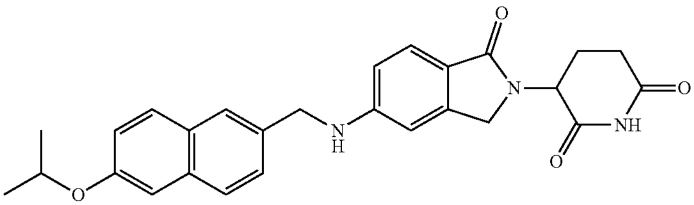 3-(5-(((6-isopropoxynaphthalen-2-yl)methyl)amino)-1-oxoisoindolin-2-yl)piperidine-2,6-dione | $^1$H NMR (400 MHz, DMSO-d$_6$) δ 10.90 (s, 1H), 7.78-7.73 (m, 3H), 7.44 (dd, J = 8.5, 1.3 Hz, 1H), 7.38 (d, J = 8.4 Hz, 1H), 7.28 (d, J = 2.4 Hz, 1H), 7.09 (dd, J = 9.0, 2.5 Hz, 1H), 7.06 (t, J = 5.9 Hz, 1H), 6.73 (dd, J = 8.4, 1.8 Hz, 1H), 6.69 (s, 1H), 4.99 (dd, J = 13.2, 5.1 Hz, 1H), 4.74 (sept, J = 6.0 Hz, 1H), 4.47 (d, J = 5.9 Hz, 2H), 4.23 (d, J = 16.8 Hz, 1H), 4.09 (d, J = 16.8 Hz, 1H), 2.92-2.82 (m, 1H), 2.59-2.53 (m, 1H), 2.35-2.24 (m, 1H), 1.94-1.87 (m, 1H), 1.32 (d, J = 6.0 Hz, 6H). $^{13}$C NMR (101 MHz, DMSO-d$_6$) δ 172.93, 171.38, 168.62, 155.05, 152.09, 144.33, 134.46, 133.49, 129.08, 128.20, 126.91, 126.12, 125.11, 123.92, 119.55, 119.16, 112.74, 108.06, 104.78, 69.15, 51.26, 46.74, 46.27, 31.26, 22.62, 21.79. HRMS-ESI (m/z): [M + H]$^+$ calculated for $C_{27}H_{28}N_3O_4$, 458.2074; found, 458.2074. |
| DEG-40 | 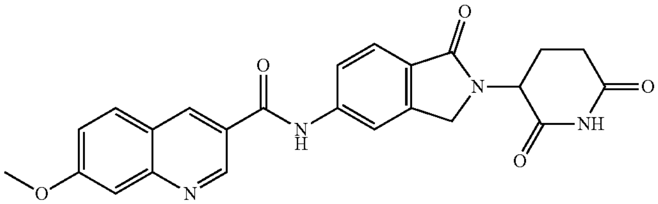 N-(2-(2,6-dioxopiperidin-3-yl)-1-oxoisoindolin-5-yl)-7-methoxyquinoline-3-carboxamide | $^1$H NMR (400 MHz, DMSO-d$_6$) δ 10.99 (s, 1H), 10.82 (s, 1H), 9.32 (d, J = 2.2 Hz, 1H), 8.91 (d, J = 2.1 Hz, 1H), 8.18 (s, 1H), 8.07 (d, J = 9.0 Hz, 1H), 7.87 (dd, J = 8.3, 1.5 Hz), 7.75 (d, J = 8.3 Hz, 1H), 7.51 (d, J = 2.4 Hz, 1H), 7.38 (dd, J = 8.9, 2.5 Hz, 1H), 5.12 (dd, J = 13.2, 5.1 Hz, 1H), 4.50 (d, J = 17.4 Hz, 1H), 4.36 (d, J = 17.4 Hz, 1H), 3.32 (s, 3H), 2.97-2.88 (m, 1H), 2.65-2.58 (m, 1H), 2.46-2.34 (m, 1H), 2.05-1.98 (m, 1H). $^{13}$C NMR (101 MHz, DMSO-d$_6$) δ 172.90, 171.11, 167.79, 164.64, 161.85, 150.72, 149.33, 143.18, 142.31, 135.94, 130.45, 126.93, 125.27, |

-continued

| | Compound structure | Characterization |
|---|---|---|
| | | 123.62, 121.46, 120.37, 119.92, 114.41, 107.30, 55.73, 51.57, 47.20, 31.23, 22.54. HRMS-ESI (m/z): $[M + H]^+$ calculated for $C_{24}H_{21}N_4O_5$, 444.1506; found, 445.1505. |
| DEG-41 | 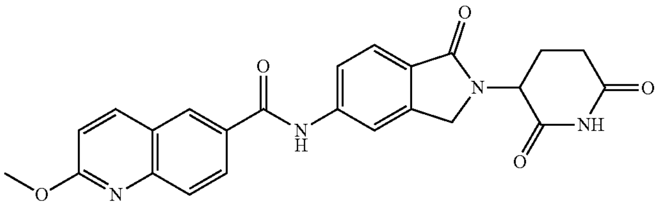 N-(2-(2,6-dioxopiperidin-3-yl)-1-oxoisoindolin-5-yl)-2-methoxyquinoline-6-carboxamide | $^1H$ NMR (400 MHz, DMSO-$d_6$) δ 10.99 (s, 1H), 10.73 (s, 1H), 8.58 (d, J = 1.7 Hz, 1H), 8.40 (d, J = 8.9 Hz, 1H), 8.22 (dd, J = 8.7, 2.0 Hz, 1H), 8.19 (s, 1H), 7.93-7.86 (m, 2H), 7.74 (d, J = 8.3 Hz, 1H), 7.13 (d, 8.9 Hz, 1H), 5.11 (dd, J = 13.3, 5.1 Hz, 1H), 4.49 (d, J = 17.2 Hz, 1H), 4.34 (d, J = 17.2 Hz, 1H), 4.03 (s, 3H), 2.98-2.88 (m, 1H), 2.65-2.58 (m, 1H), 2.46-2.33 (m, 1H), 2.06-1.99 (m, 1H). $^{13}C$ NMR (101 MHz, DMSO-$d_6$) δ 172.91, 171.12, 167.84, 165.56, 163.24, 147.72, 143.14, 142.52, 140.23, 130.17, 128.52, 128.36, 126.85, 126.78, 124.00, 123.56, 119.93, 114.39, 113.99, 53.46,51.57, 47.20, 31.23, 22.55. HRMS-ESI (m/z): $[M + H]^+$ calculated for $C_{24}H_{21}N_4O_5$, 444.1506; found, 445.1498. |
| DEG-42 | 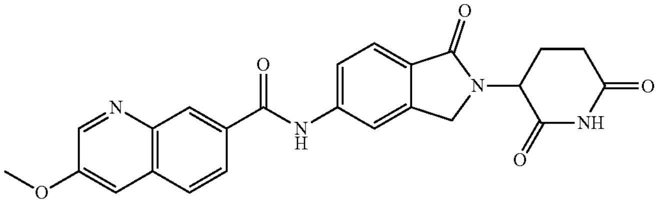 N-(2-(2,6-dioxopiperidin-3-yl)-1-oxoisoindolin-5-yl)-3-methoxyquinoline-7-carboxamide | $^1H$ NMR (400 MHz, DMSO-$d_6$) δ 10.99 (s, 1H), 10.78 (s, 1H), 8.77 (d, J = 2.9 Hz, 1H), 8.68 (s, 1H), 8.21 (s, 1H), 8.11 (dd, J = 8.5, 1.6 Hz, 1H), 8.04 (d, J = 8.6 Hz, 1H), 7.91 (dd, J = 8.3, 1.3 Hz, 1H), 7.87 (d, J = 2.7 Hz, 1H), 7.73 (d, J = 8.3 Hz, 1H), 5.12 (dd, J = 13.2, 5.1 Hz, 1H), 4.49 (d, J = 17.4 Hz, 1H), 4.35 (d, J = 17.2 Hz, 1H), 3.98 (s, 3H), 2.98-2.88 (m, 1H), 2.65-2.57 (m, 1H), 2.47-2.34 (m, 1H), 2.06-1.98 (m, 1H). $^{13}C$ NMR (101 MHz, DMSO-$d_6$) δ 172.91, 171.12, 167.84, 165.52, 153.99, 145.51, 143.11, 142.49, 141.90, 132.41, 130.84, 128.48, 127.36, 126.81, 125.81, 123.53, 120.01, 114.47, 112.41, 55.77, 51.57, 47.19, 31.23, 22.55. HRMS-ESI (m/z): $[M + H]^+$ calculated for $C_{24}H_{21}N_4O_5$, 444.1506; found, 445.1504. |
| DEG-43 | 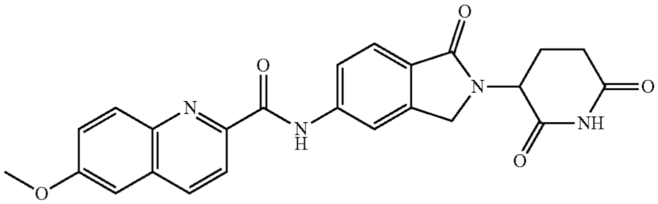 N-(2-(2,6-dioxopiperidin-3-yl)-1-oxoisoindolin-5-yl)-6-methoxyquinoline-2-carboxamide | $^1H$ NMR (400 MHz, DMSO-$d_6$) δ 10.99 (s, 1H), 10.96 (s, 1H), 8.51 (d, J = 8.6 Hz, 1H), 8.29 (s, 1H), 8.21 (d, J = 8.5 Hz, 1H), 8.17 (d, J = 9.2 Hz, 1H), 8.05 (d, J = 9.6 Hz, 1H), 7.75 (d, J = 8.3 Hz, 1H), 7.57 (dd, J = 9.2, 3.0 Hz, 1H), 7.52 (d, J = 2.7 Hz, 1H), 5.12 (dd, J = 13.3, 5.1 Hz, 1H), 4.50 (d, J = 17.2 Hz, 1H), 4.36 (d, J = 17.2 Hz, 1H), 3.95 (s, 3H), 2.99-2.88 (m, 1H), 2.65-2.58 (m, 1H), 2.47-2.36 (m, 1H), 2.05-1.99 (m, 1H). $^{13}C$ NMR (101 MHz, DMSO-$d_6$) δ 173.39, 171.60, 168.28, 163.72, 159.25, 147.76, 143.65, 142.33, 142.13, 137.20, 131.34, 131.05, 127.46, 124.08, 124.01, 120.47, 119.64, 114.83, 106.21, 56.24, 52.06, 47.67, 31.71, 23.01. HRMS-ESI (m/z): $[M + H]^+$ calculated for $C_{24}H_{21}N_4O_5$, 444.1506; found, 445.1505. |
| DEG-44 | 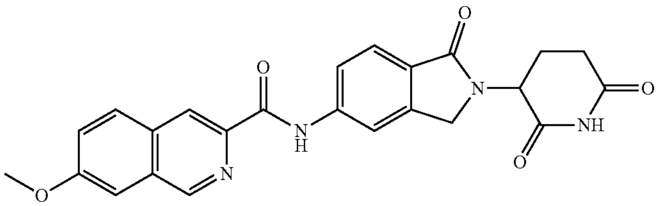 N-(2-(2,6-dioxopiperidin-3-yl)-1-oxoisoindolin-5-yl)-7-methoxyquinoline-3-carboxamide | $^1H$ NMR (400 MHz, DMSO-$d_6$) δ 10.99 (s, 2H), 8.66 (s, 1H), 8.31 (s, 1H), 8.18 (d, J = 9.0 Hz, 1H), 8.05 (d, J = 7.9 Hz, 1H), 7.73 (s, 1H), 7.71 (s, 1H), 7.55 (d, J = 9.0 Hz, 1H), 5.11 (dd, J = 13.2, 4.9 Hz, 1H), 4.49 (d, J = 17.1 Hz, 1H), 4.34 (d, J = 17.1 Hz, 1H), 3.97 (s, 3H), 2.97-2.88 (m, 1H), 2.65-2.57 (m, 1H), 2.46-2.34 (m, 1H), 2.05-1.98 (m, 1H). $^{13}C$ NMR (101 MHz, DMSO-$d_6$) δ 172.95, 171.15, 167.83, 163.32, 159.74, 149.93, 143.11, 141.86, 141.56, 131.23, 130.88, 129.86, 126.84, 124.23, 123.52, 120.70, 119.99, |

-continued

| | Compound structure | Characterization |
|---|---|---|
| | | 114.32, 105.81, 55.71, 51.57, 47.18, 31.25, 22.54. HRMS-ESI (m/z): $[M + H]^+$ calculated for $C_{24}H_{21}N_4O_5$, 444.1506; found, 445.1504. |
| DEG-45 | 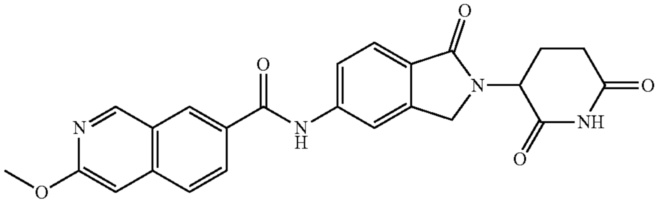 N-(2-(2,6-dioxopiperidin-3-yl)-1-oxoisoindolin-5-yl)-3-methoxyquinoline-7-carboxamide | $^1$H NMR (400 MHz, DMSO-$d_6$) δ 11.00 (s, 1H), 10.76 (s, 1H), 9.24 (s, 1H), 8.74 (s, 1H), 8.18 (s, 1H), 8.16 (dd, J = 8.7, 1.8 Hz, 1H), 7.95 (d, J = 8.8 Hz, 1H), 7.88 (dd, J = 8.3, 1.6 Hz, 1H), 7.74 (d, J = 8.3 Hz, 1H), 7.28 (s, 1H), 5.12 (dd, J = 13.2, 5.1 Hz, 1H), 4.49 (d, J = 17.3 Hz, 1H), 4.35 (d, J = 17.3 Hz, 1H), 2.98-2.89 (m, 1H), 2.61 (d, J = 16.5 Hz, 1H), 2.47-2.35 (m, 1H), 2.05-1.98 (m, 1H). $^{13}$C NMR (101 MHz, DMSO-$d_6$) δ 172.91, 171.13, 167.83, 165.39, 162.21, 152.44, 143.15, 142.46, 140.17, 130.49, 129.01, 128.50, 126.82, 125.82, 123.73, 123.57, 119.94, 114.41, 100.87, 54.23, 51.58, 47.20, 31.24, 22.55. |
| DEG-46 | 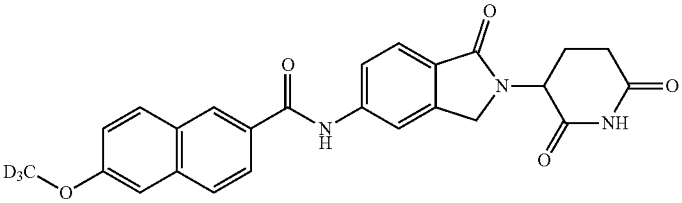 N-(2-(2,6-dioxopiperidin-3-yl)-1-oxoisoindolin-5-yl)-6-(methoxy-d3)-2-naphthamide | $^1$H NMR (400 MHz, DMSO-$d_6$) δ 10.99 (s, 1H), 10.66 (s, 1H), 8.54 (s, 1H), 8.19 (s, 1H), 8.03-7.94 (m, 3H), 7.88 (dd, J = 8.3, 1.5 Hz, 1H), 7.73 (d, J = 8.3 Hz, 1H), 7.43 (d, J = 2.4 Hz, 1H), 7.28 (dd, J = 9.0, 2.5 Hz, 1H), 5.11 (dd, J = 13.3, 5.1 Hz, 1H), 4.49 (d, J = 17.4 Hz, 1H), 4.34 (d, J = 17.2 Hz, 1H), 2.98-2.88 (m, 1H), 2.65-2.58 (m, 1H), 2.46-2.35 (m, 1H), 2.05-1.98 (m, 1H). $^{13}$C NMR (101 MHz, DMSO-$d_6$) δ 172.91, 171.13, 167.86, 166.03, 158.84, 143.13, 142.65, 136.12, 130.61, 129.57, 128.13, 127.35, 126.87, 126.65, 125.00, 123.53, 119.89, 119.58, 114.33, 105.95, 51.57, 47.19, 31.23, 22.55. HRMS-ESI (m/z): $[M + H]^+$ calculated for $C_{25}H_{19}D_3N_3O_5$, 447.1742; found, 447.1742. |
| DEG-47 | 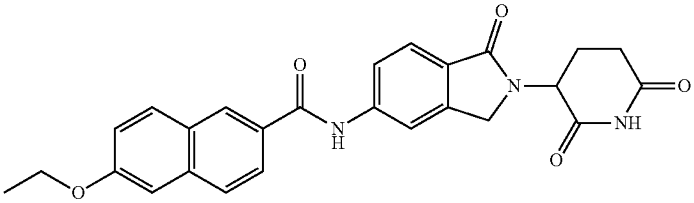 N-(2-(2,6-dioxopiperidin-3-yl)-1-oxoisoindolin-5-yl)-6-ethoxy-2-naphthamide | $^1$H NMR (400 MHz, DMSO-$d_6$) δ 10.99 (s, 1H), 10.65 (s, 1H), 8.53 (s, 1H), 8.19 (s, 1H), 8.02-7.98 (m, 2H), 7.93 (d, J = 8.7 Hz, 1H), 7.88 (dd, J = 8.3, 1.5 Hz, 1H), 7.73 (d, J = 8.3 Hz, 1H), 7.41 (d, J = 2.3 Hz, 1H), 7.26 (dd, J = 8.9, 2.5 Hz, 1H), 5.11 (dd, J = 13.3, 5.1 Hz, 1H), 4.49 (d, J = 17.4 Hz, 1H), 4.34 (d, J = 17.2 Hz, 1H), 4.20 (q, J = 7.0 Hz, 2H), 2.98-2.88 (m, 1H), 2.64-2.58 (m, 1H), 2.46-2.34 (m, 1H), 2.05-1.98 (m, 1H), 1.42 (d, J = 6.9 Hz, 3H). $^{13}$C NMR (101 MHz, DMSO-$d_6$) δ 172.91, 171.13, 167.86, 166.04, 158.08, 143.13, 142.65, 136.14, 130.61, 129.51, 128.11, 127.28, 126.85, 126.64, 124.94, 123.53, 119.89, 119.76, 114.33, 106.54, 63.35, 51.56, 47.19, 31.23, 22.55, 14.59. HRMS-ESI (m/z): $[M + H]^+$ calculated for $C_{26}H_{24}N_3O_5$, 458.1710; found, 458.1713. |
| DEG-48 | 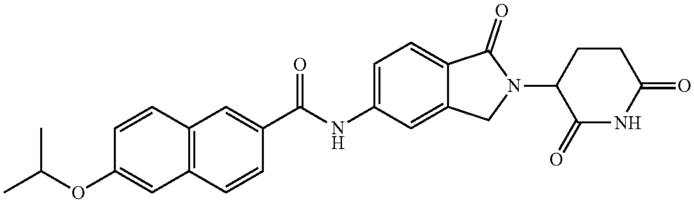 N-(2-(2,6-dioxopiperidin-3-yl)-1-oxoisoindolin-5-yl)-6-isopropoxy-2-naphthamide | $^1$H NMR (400 MHz, DMSO-$d_6$) δ 10.99 (s, 1H), 10.64 (s, 1H), 8.53 (s, 1H), 8.19 (s, 1H), 8.01-7.97 (m, 2H), 7.94-7.86 (m, 2H), 7.73 (d, J = 8.3 Hz, 1H), 7.43 (d, J = 2.0 Hz, 1H), 7.23 (dd, J = 9.0, 2.3 Hz, 1H), 5.11 (dd, J = 13.2, 5.1 Hz, 1H), 4.83 (sept, J = 6.0 Hz, 1H), 4.49 (d, J = 17.3 Hz, 1H), 4.35 (d, J = 17.2 Hz, 1H), 2.99-2.87 (m, 1H), 2.64-2.58 (m, 1H), 2.47-2.33 (m, 1H), 2,05-1.99 (m, 1H), 1.36 (d, J = 6.0 Hz, 6H). $^{13}$C NMR (101 MHz, DMSO-$d_6$) δ 172.90, 171.12, 167.86, 166.01, 156.95, 143.12, 142.65, 136.17, 130.71, 129.39, 128.07, 127.13, 126.81, 126.63, 124.86, 123.52, 120.35, 119.89, 114.33, 107.75, 69.43, 51.56, 47.18, |

-continued

| Compound structure | Characterization |
| --- | --- |
| | 31.23, 22.54, 21.76. HRMS-ESI (m/z): $[M + H]^+$ calculated for $C_{27}H_{26}N_3O_5$, 472.1867; found, 472.1867. |
| DEG-49 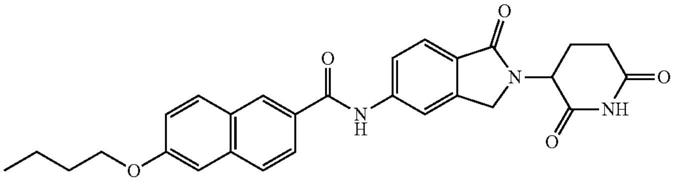 6-butoxy-N-(2-(2,6-dioxopiperidin-3-yl)-1-oxoisoindolin-5-yl)-2-naphthamide | $^1$H NMR (400 MHz, DMSO-$d_6$) δ 10.99 (s, 1H), 10.65 (s, 1H), 8.53 (s, 1H), 8.19 (s, 1H), 8.01-7.86 (m, 4H), 7.73 (d, J = 8.3 Hz, 1H), 7.43 (d, J = 2.3 Hz, 1H), 7.26 (dd, J = 8.9, 2.5 Hz, 1H), 5.11 (dd, J = 13.2, 5.1 Hz, 1H), 4.49 (d, J = 17.5 Hz, 1H), 4.35 (d, J = 17.5 Hz, 1H), 4.14 (t, J = 6.6 Hz, 2H), 2.98-2.87 (m, 1H), 2.65-2.57 (m, 1H), 2.47-2.34 (m, 1H), 2.06-1.98 (m, 1H), 1.79 (quint, J = 0.7 Hz, 2H), 1.54-1.45 (m, 2H), 0.97 (t, J = 7.4 Hz, 3H). $^{13}$C NMR (101 MHz, DMSO-$d_6$) δ 172.91, 171.13, 167.86, 166.04, 158.24, 143.13, 142.65, 136.15, 130.59, 129.50, 128.10, 127.27, 126.84, 126.64, 124.94, 123.52, 119.89, 119.78, 114.33, 106.58, 67.42, 51.57, 47.19, 31.23, 30.68, 22.55, 18.79, 13.72. HRMS-ESI (m/z): $[M + H]^+$ calculated for $C_{28}H_{28}N_3O_5$, 486.2023; found, 486.2025. |

To determine the selectivity of DEG-7 and DEG-35, blotting was done for other known IMiD neo-substrates (FIG. 1A). DEG-35 degraded casein kinase 1α (CK1α), a known substrate of lenalidomide, as well as the translation termination factor GSPT1, a substrate of the IMiD CC-885, at 25 μM concentrations. To investigate whether DEG-35 could degrade IKZF2 at lower concentrations, MOLM13 cells were treated with a concentration gradient. At the lowest concentration tested (5 nM), IKZF2 and CK1a degraded, while GSPT1 levels were unperturbed. These data suggest that the primary targets of DEG-35 are IKZF2 and CK1α, and that a therapeutic window to prevent broad-spectrum degradation of GSPT1 is possible (FIG. 1A).

In preparation for in vivo studies, these compounds were evaluated in a mouse model of AML. Evaluation of these degraders in mouse models requires a humanized CRBN leukemia model, because mouse CRBN is not able to functionally engage with these drugs compared to human CRBN. Thus, to create a humanized CRBN leukemia model, bone marrow cells were transformed with either WT or mouse mutant CRBN I391V that has been shown to engage these IMIDs. DEG-35 demonstrated similar nanomolar activity to the human cells in the mouse CRBN mutant and resulted in reduced colony formation (data not shown). Importantly, this activity was only observed in the mutant CRBN lines indicating that these compounds were acting through a CRBN-dependent degrader pathway and not off-target toxicity. Moreover, the mutant CRBN mouse line MLLAF9-hCRBN has now established. To determine if the decrease in protein was CRBN-dependent, the mouse cell line MLLAF9 with either mouse CRBN (mCRBN) or human CRBN (hCRBN) were treated with DEG-35. No degradation of IKZF2 was observed in MLLAF9-mCRBN cells while significant degradation was observed in MLL-AF9-hCRBN cells. Interestingly, CK1a was degraded in the MLL-AF9-mCRBN cell line suggesting that DEG-35 may be recruiting CK1a to CRBN in an orientation that is distinct from that of lenalidomide.

Identification of Lead Compounds that are Selective Nanomolar Inhibitors of AML

Figure 2A:
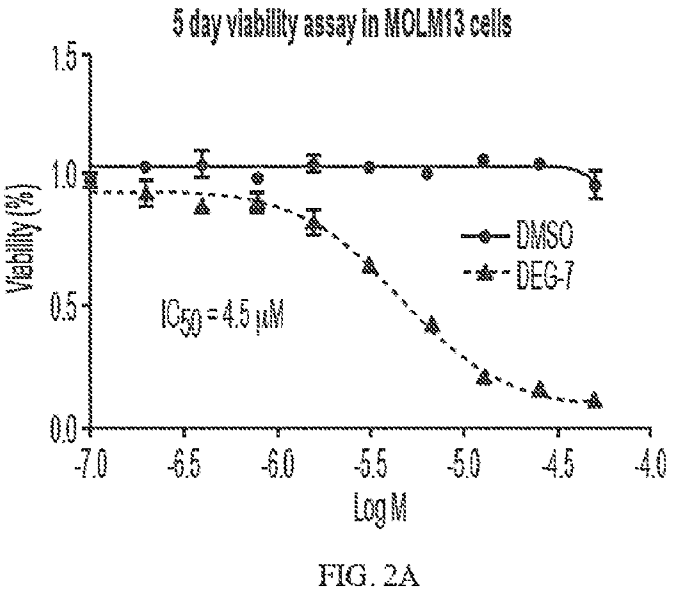
FIG. 2A. MTT assay with DEG-7.
Figure 2B:
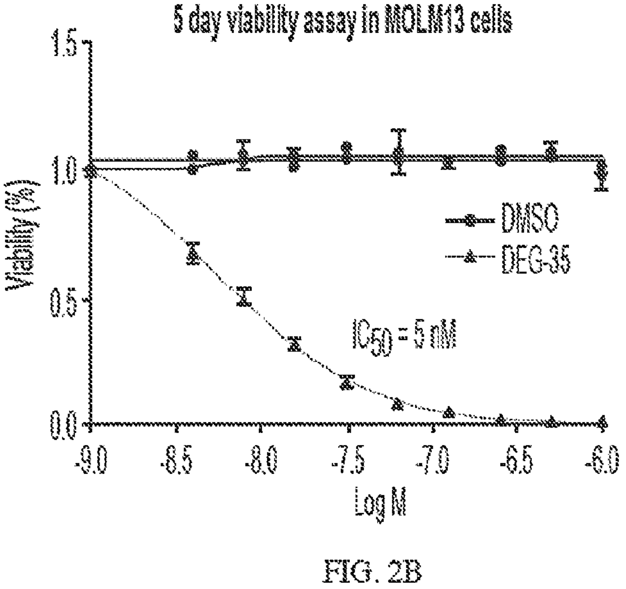
FIG. 2B. MTT assay showing DEG-35 is a potent nanomolar degrader.
Figure 2C:
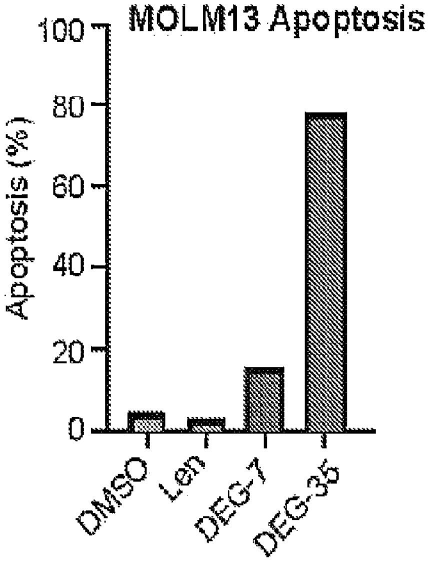
FIG. 2C. DEG-35 strongly induces apoptosis of cells.
Figure 2D:
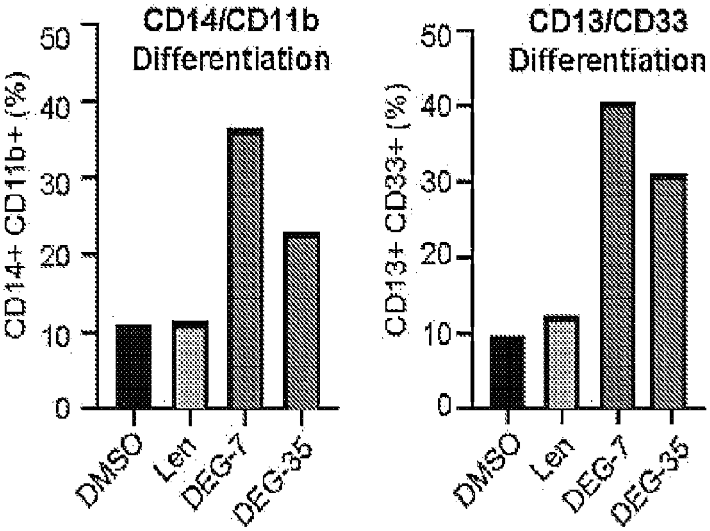
FIG. 2D. DEG-7 is more efficient at inducing differentiation than DEG-35.
Figure 3:
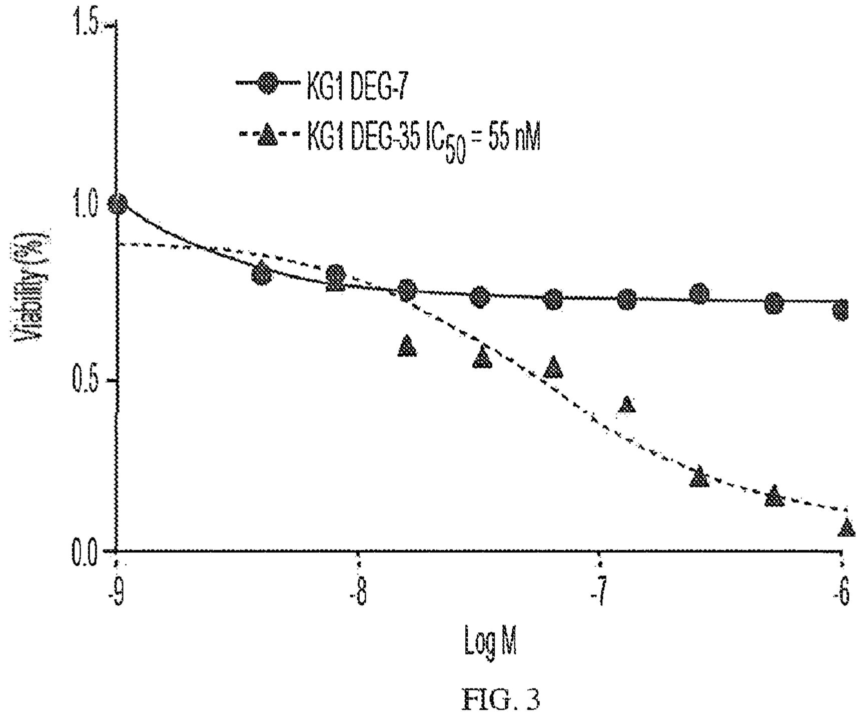
FIG. 3 is a plot showing a five-day viability assay using DEG-7 and DEG-35 against KG1 cells.

The effect of DEG-7 and DEG-35 were evaluated on cell viability in MOLM13 cells. MTT assays showed that DEG-7 and DEG-35 kill MOLM13 cells with $IC_{50}$ values of 4.5 μM and 5 nM respectively (FIG. 2A-B). Both compounds induced apoptosis markers in MOLM13 cells, implying that the degraders are primarily activating apoptosis-driven cell death (FIG. 2C). In addition, both compounds induced differentiation in MOLM13 (FIG. 2D). Surprisingly, evaluation of DEG-7 and DEG-35 in additional AML cell lines (NOMO1, KASUMI) showed no observed effect on cell viability, antiproliferation, apoptosis, or differentiation. In addition to MOLM-13, KG1 cells were sensitive to DEG-35 ($IC_50$=55 nM), while NOMO1 and KASUMI cells showed no observed effect on cell viability, anti-proliferation, apoptosis, or differentiation (FIG. 3). The selective cell type sensitivity of DEG-7 and DEG-35 is reminiscent of the high selectivity of lenalidomide against a small subset of multiple myeloma cell lines. These data indicate that there is a likely correlation between specific biomarkers found in MOLM-13 and KG1 cells that are predictive for sensitivity to our degraders and that these compounds will not display broad-spectrum cell death.

Figure 4A:
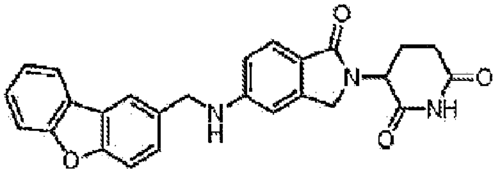
FIG. 4A. Structure of DEG-37.
Figure 4B:
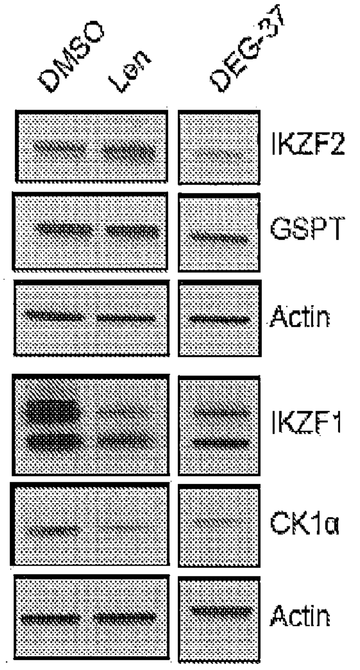
FIG. 4B. DEG-37 degrades IKZF2 in MOLM13 cells at 25 μM.
Figure 4C:
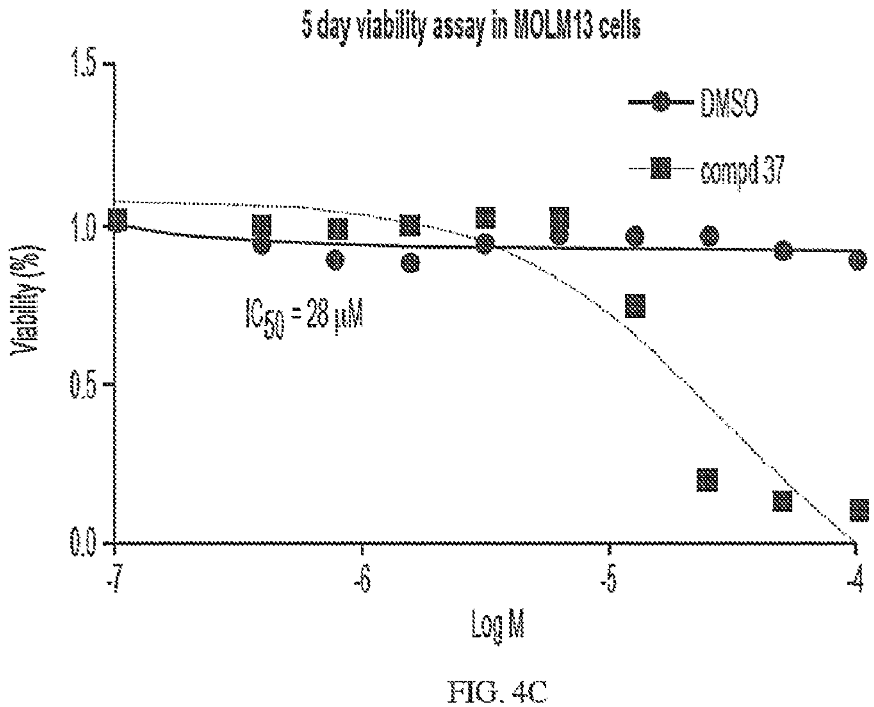
FIG. 4C. DEG-37 possesses antiproliferative effects in MOLM13 cells.

DEG-37 is also a suitable lead compound for IKZF2 targeted degradation (FIG. 4). Based on current knowledge, DEG-37 may be a suitable alternative to DEG-7 as a pro-differentiation therapeutic, due to its ability to selectively degrade IKZF2, minimally effect GSPT1 and IKZF1 levels, and possesses milder antiproliferative effects against MOLM13 cells.

Determining the Mechanism of Anti-Proliferative Activity

DEG-7 and DEG-35 were submitted to the Broad Institute's PRISM (Profiling Relative Inhibition Simultaneously in Mixtures) screen to be evaluated against over 800 cancer cell lines. The initial screen identified cancer cell lines that were responsive to DEG-7 and DEG-35 treatment. MOLM13 was shown to be sensitive to DEG-7. DEG-35 showed high selectivity for several lineages and did not display broad toxicity. Several diffuse large B-cell lymphoma (DLBCL), acute myeloid leukemia (AML), and T-cell acute lymphoblastic leukemia (T-ALL) cell lines responded to DEG-35 in a dose-dependent manner. Of the top ten cell lines that responded to DEG-35 treatment, three were DLBCL cell lines, one was an AML cell line (MOLM13), and one was a T-ALL cell line. Of the top forty responsive cell lines, three additional AML cell lines and an additional four T-ALL cell lines showed sensitivity to DEG-35.

Figure 5:
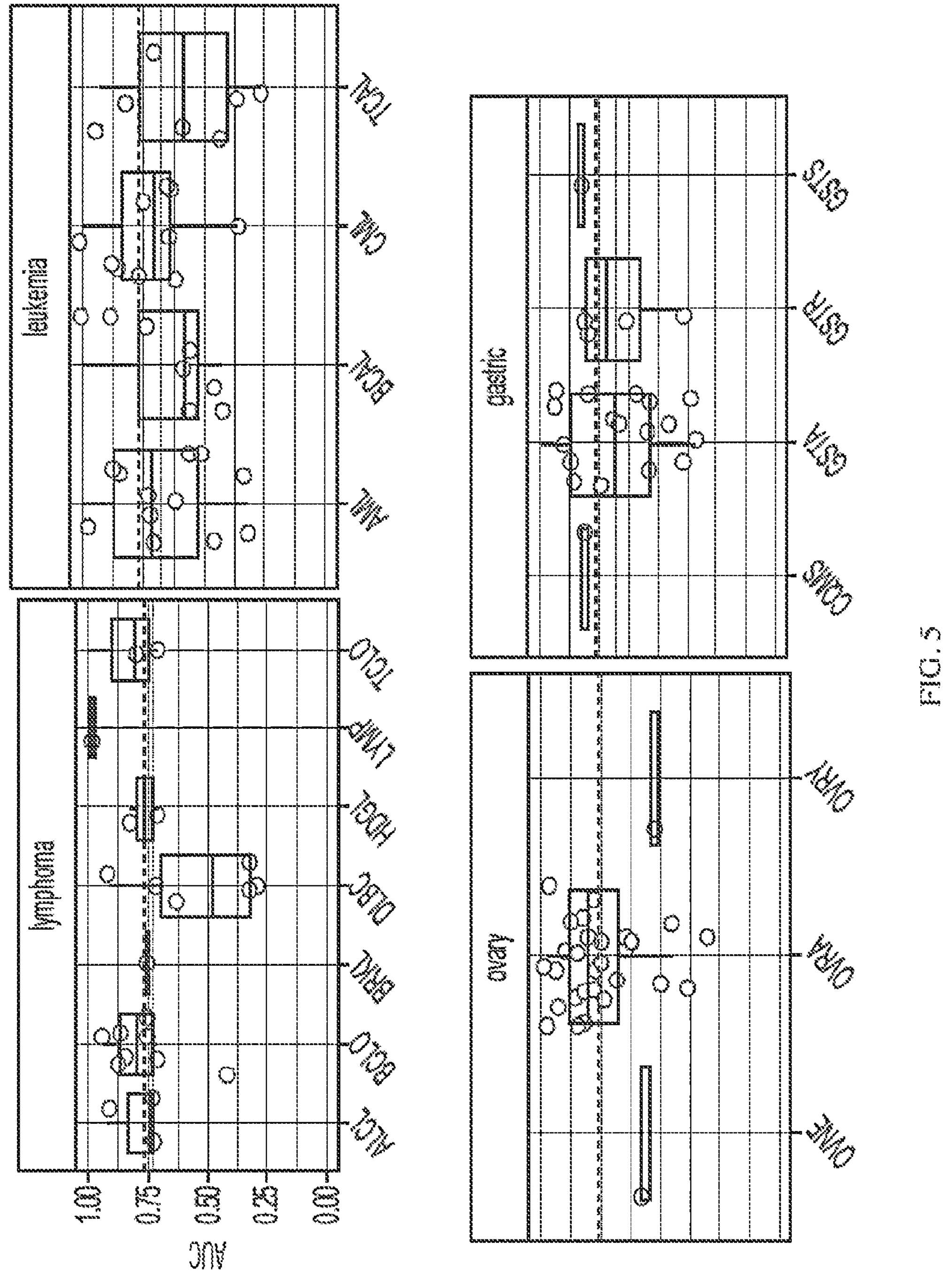
FIG. 5 is a series of plots showing the cell lineage sensitivity of DEG-35. Lineages that are more sensitive to DEG-35 include DLBCL (diffuse large B-cell lymphoma) and a subset of AML (acute myelocytic leukemia), TCAL (T-cell acute lymphoblastic leukemia), BCAL (B-cell acute lymphoblastic leukemia), OVRA (ovarian adenocarcinoma), GSTR (gastric) and GSTA (gastric adenocarcinoma) lines.

The cell lineage sensitivity of DEG-35 is depicted in FIG. 5. Lineages that are more sensitive to DEG-35 include DLBCL (diffuse large B-cell lymphoma) and a subset of AML (acute myelocytic leukemia), TCAL (T-cell acute lymphoblastic leukemia), BCAL (B-cell acute lymphoblastic leukemia), OVRA (ovarian adenocarcinoma), GSTR (gastric) and GSTA (gastric adenocarcinoma) lines Based on the responsive cell lines and the IC50 of DEG-35 in each cell line, bioinformatic analysis was performed to identify predictive biomarkers. For DEG-35, mutations in the tumor suppressor p53 were shown to confer resistance to drug treatment.

A correlation analysis was performed of the dependency of a cell line on a specific gene with the sensitivity to the compound at a given dose using different libraries (CrispR, micro RNA, shRNA, etc). Positive correlations indicate increased sensitivity to the compound. Using both a CrispR knock-out and shRNA library, MDM4, a suppressor of p53 function, was identified to correlate with DEG-35 treatment at multiple doses.

In addition, DEG-35 sensitivity was correlated with sensitivity to a number of different known drugs, including a number of MDM2 inhibitors, such as idasanutlin, AMG-232, RG7112, SAR405838, and nutlin-3. MDM2 is a homolog of MDM4 that also functions as a suppressor of p53. While MDM4 binds to p53's DNA-binding domain preventing p53 from binding to its transcriptional targets, MDM2 functions as an E3 ligase that causes p53 to be ubiquitinated and subsequently degraded by the proteasome.

These results suggest that a main driver of DEG-35 anti-proliferative activity is through the p53/MDM2/MDM4 pathway. CK1a is known to form a complex with MDM2 enabling its p53 inhibition function, as well as phosphorylate MDM4 causing it to bind and inhibit p53. Thus, DEG-35 degradation of CK1a may activate p53's tumor suppressing function.

Figure 6:
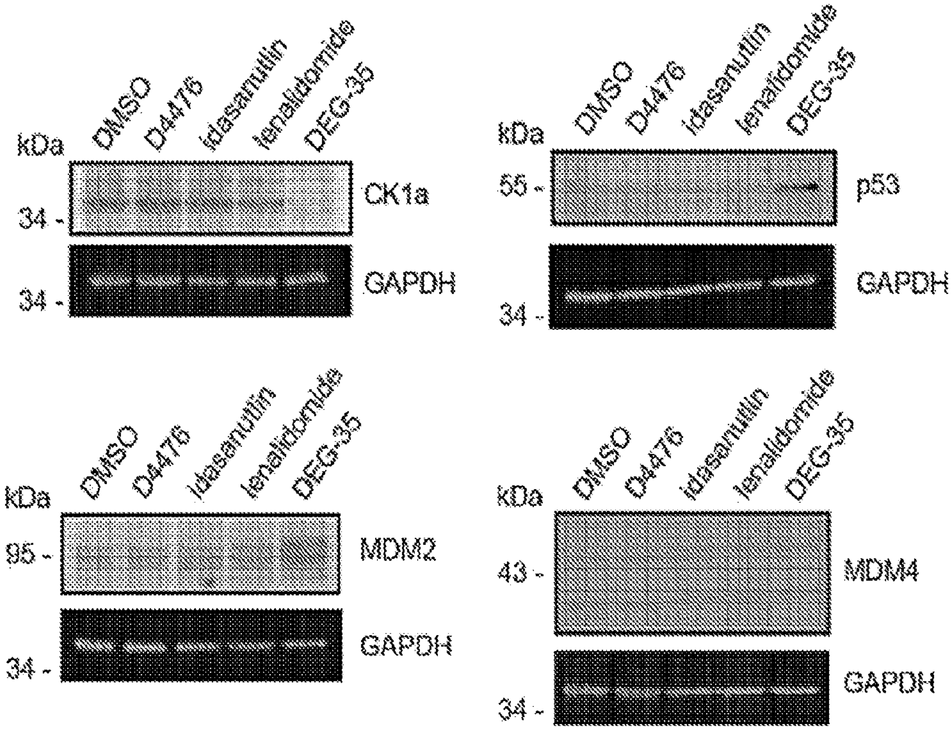
FIG. 6 is a series of Western blots showing the effect of D4476, idasanutlin, lenalidomide, and exemplary compound DEG-35 on CK1α, p53, MDM2 and MDM4 in MOLM13 cells.

To test this hypothesis, MOLM13 cells were treated with 1 μM of DEG-35. Changes in p53, MDM2, and MDM4 were observed by Western blot (FIG. 6). Consistent with this proposed mechanism, CK1a degraded upon treatment of DEG-35, stabilized p53 and upregulated MDM2 which is also a transcriptional target of p53.

Development of Picomolar Antiproliferative Agents Against AML

Lead compounds DEG-7 and DEG-35 are potent degraders of IKZF2, and DEG-35 is further a potent anti-proliferative of MOLM13 cells ($IC_{50}$=5 nM). The potency and selectivity of these compounds may be increased by at least ten-fold using a deuteration and chiral purification strategy to afford S-DEG-7-d and S-DEG-35-d as a set of final lead compounds for clinical translation.

S-DEG-7-d

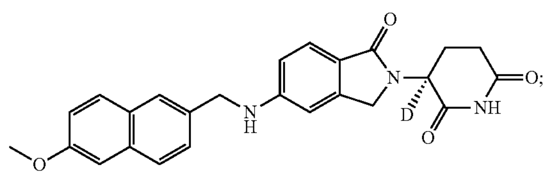

-continued

S-DEG-35-d

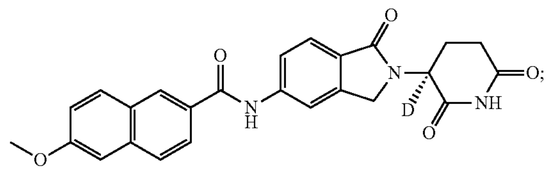

The selectivity and potency of DEG-7 and DEG-35 may be enhanced by stabilizing the more active S enantiomer of DEG-35 and DEG-7 with deuterium. The synthetic route to preparing the compounds is amenable to scale up and able to afford the amounts of compound required for preclinical animal studies.

Three effects from the use of enantiopure deuterated degraders are expected: first, the S-enantiomer will promote engagement of CRBN and thus increase potency of DEG-35; second, removal of the R-enantiomer will reduce off-target complex formation and client protein degradation that is specifically promoted by the R-enantiomer (e.g., AKR1B1); third, deuteration of lead compounds will stabilize the S-enantiomer and reduce metabolic disintegration of the compound, thus enhancing on-target degradation of the desired client proteins IKZF2 and CK1α. These properties will be evaluated against MOLM13 cells using the enantiopure and racemic versions of DEG-7 and DEG-35 after synthesis of the corresponding enantiopure compounds. Based on prior comparison of racemic versus enantiopure degrader scaffolds, it is expected that there will be at least a 10-fold increase in potency, due to the increased effective concentration of the S-enantiomer combined with the catalytic ubiquitinylation and degradation of the client proteins.

Taken together, the disclosure data provides an original and novel example of compounds that can degrade IKZF2 and provide a path towards targeting leukemia stem cells in AML and other cancers.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms “comprising” and “containing” are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (Ib):

(I-b)

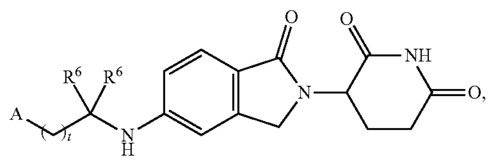

or a pharmaceutically acceptable salt or isotopically enriched derivative thereof, wherein:

A is substituted or unsubstituted naphthyl, substituted or unsubstituted benzofuran, substituted or unsubstituted quinoline, substituted or unsubstituted isoquinoline, or substituted or unsubstituted dibenzofuran;

each $R^6$ is, independently, hydrogen, halogen, or $C_1$-$C_3$ alkyl; or two $R^6$, together with the carbon atom to which they are attached, form a C═O; and t is 0.

2. The compound of claim 1, or a pharmaceutically acceptable salt thereof, wherein:

each Reis hydrogen; or two $R^6$, together with the carbon atom to which they are attached, form a C═O.

3. The compound of claim 1, or a pharmaceutically acceptable salt thereof, wherein:

A is substituted or unsubstituted naphthyl, substituted or unsubstituted benzofuran, substituted or unsubstituted quinoline, or substituted or unsubstituted isoquinoline.

4. The compound of claim 1, or a pharmaceutically acceptable salt thereof, wherein:

A is substituted or unsubstituted naphthyl, or substituted or unsubstituted dibenzofuran.

5. The compound of claim 1, or a pharmaceutically acceptable salt thereof, wherein:

A is unsubstituted naphthyl or naphthyl substituted with halogen, amino, aryloxy, alkoxy, alkoxyalkyl, or hydroxyl.

6. The compound of claim 1, or a pharmaceutically acceptable salt thereof, wherein:

A is unsubstituted naphthyl or naphthyl substituted with $C_{1-4}$ alkoxy.

7. The compound of claim 1, or a pharmaceutically acceptable salt thereof, wherein:

A is

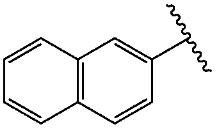, 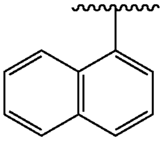,

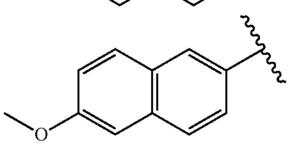, 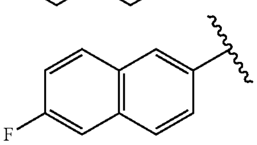,

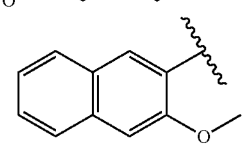, 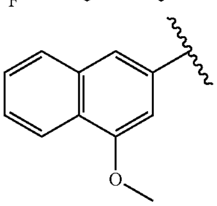,

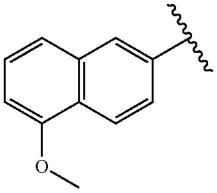, 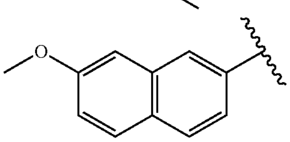,

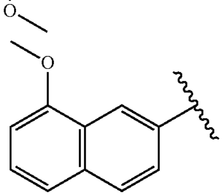, 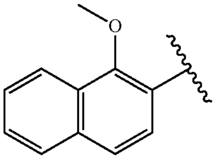,

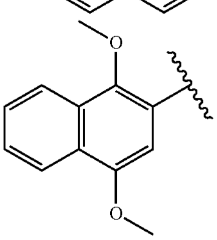, 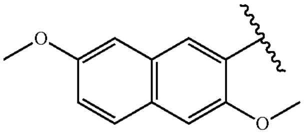,

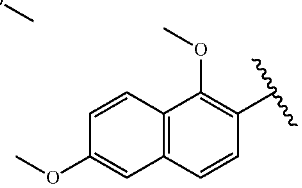,

-continued
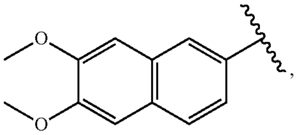
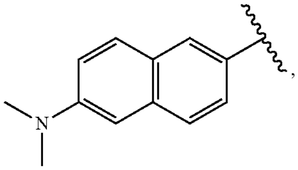
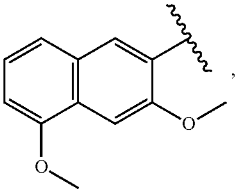
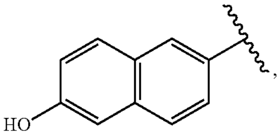
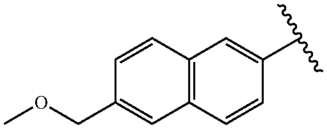
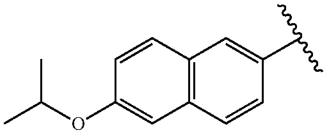
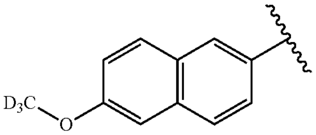
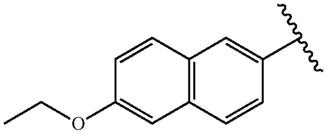
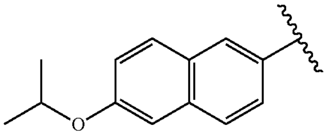
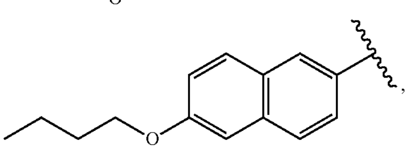
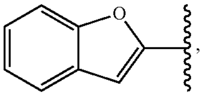
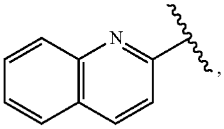
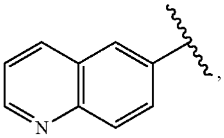
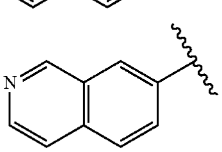
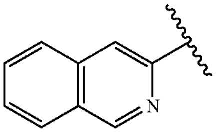
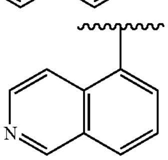
-continued
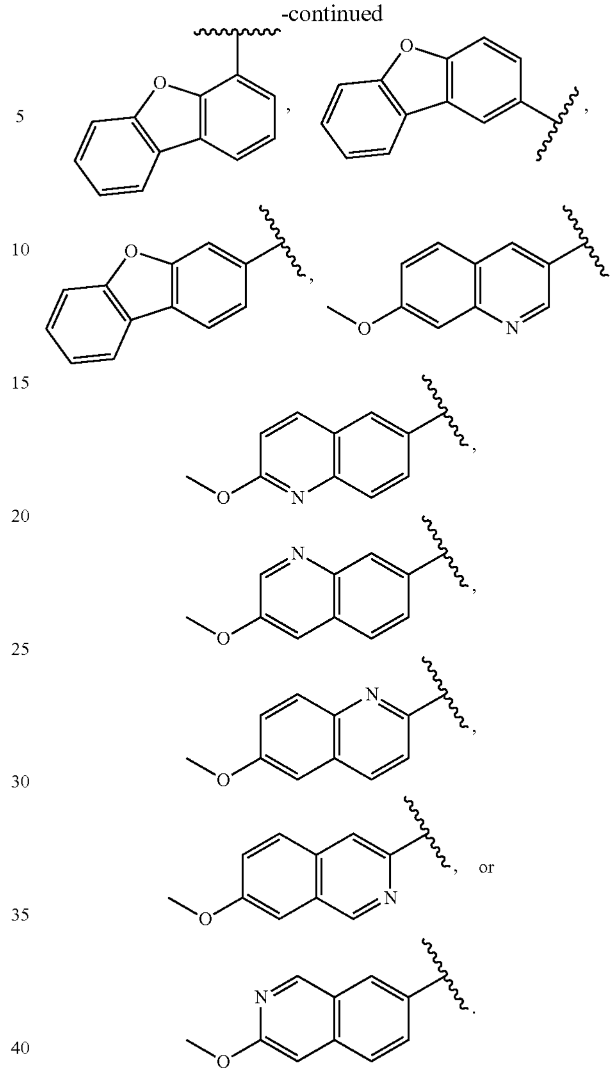
8. The compound of claim 1, wherein the compound is of formula:
(I-c)
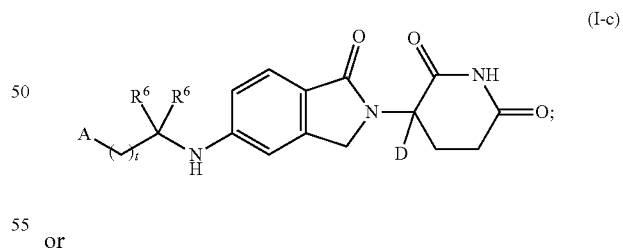
or
(I-d)
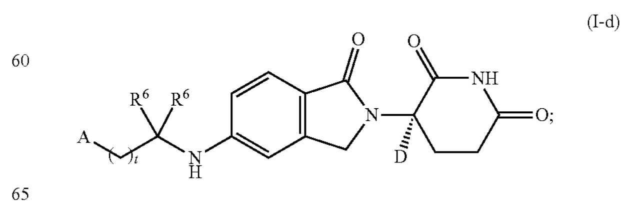
or a pharmaceutically acceptable salt thereof.

9. The compound of claim 1, wherein the compound is
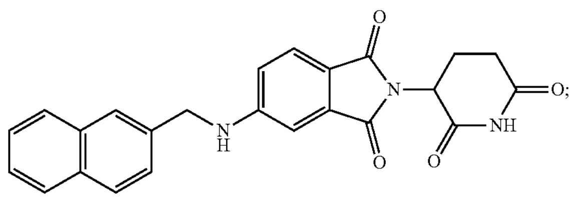
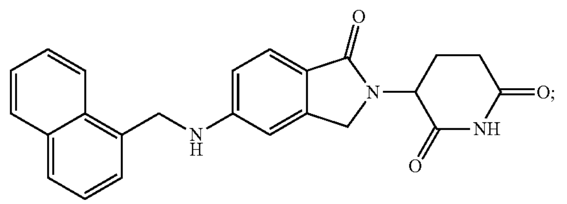
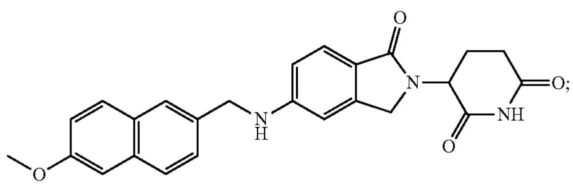
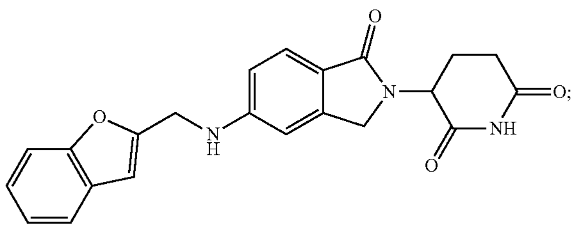
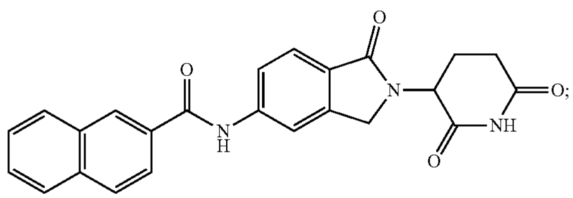
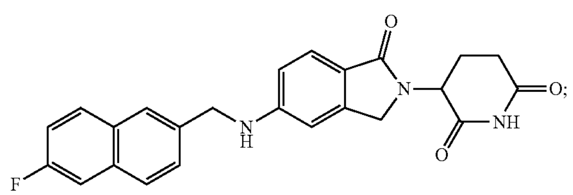
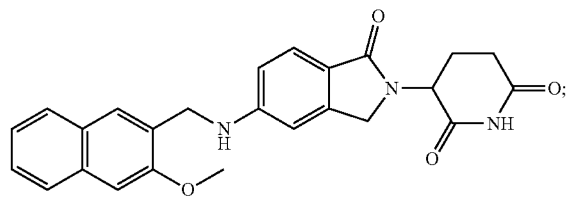
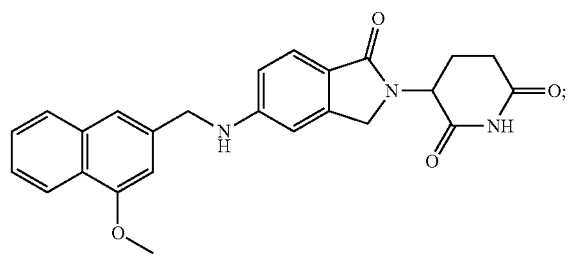
-continued
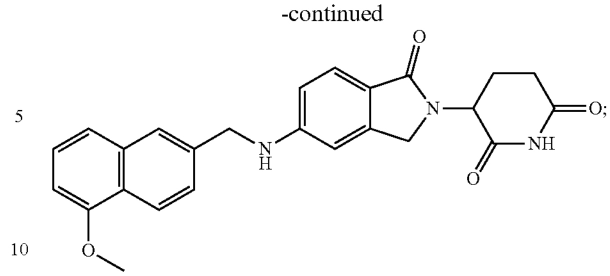
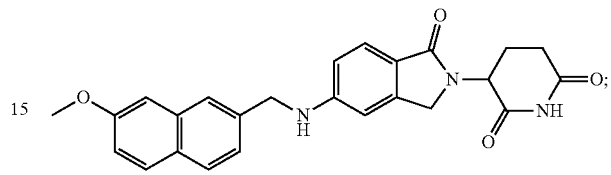
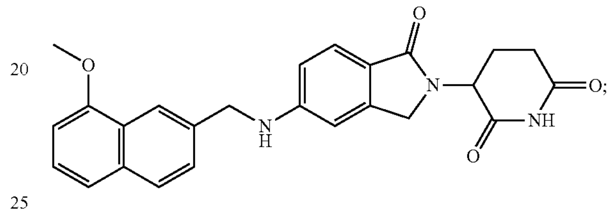
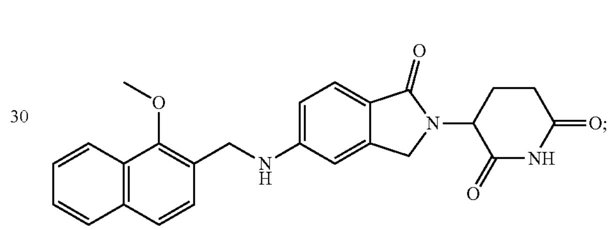
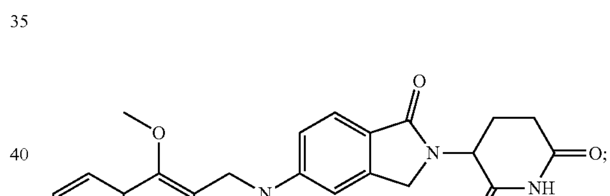
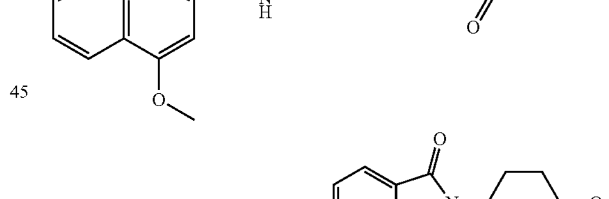
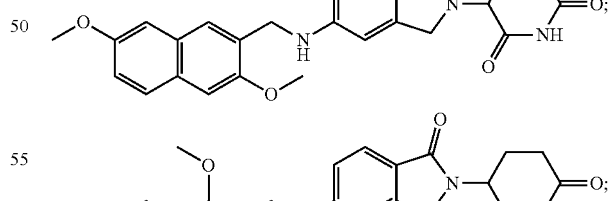
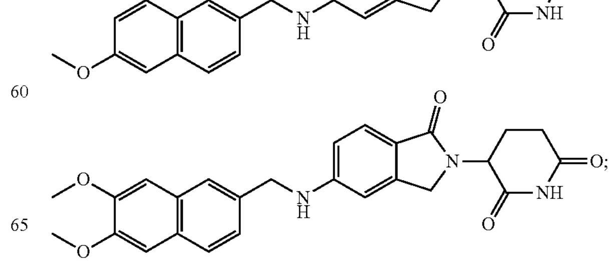

-continued
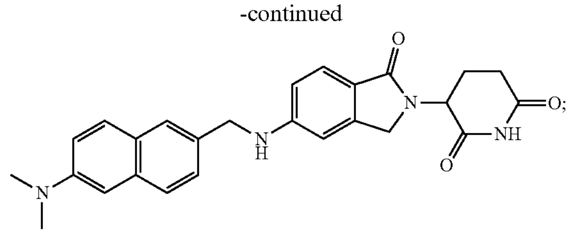
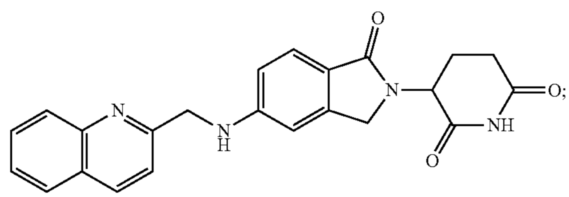
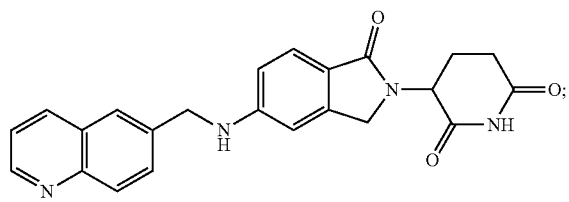
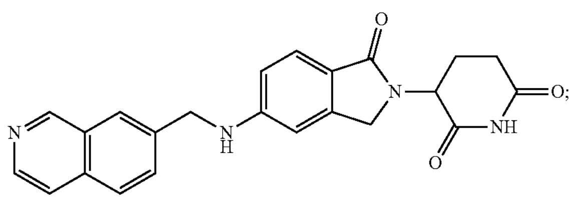
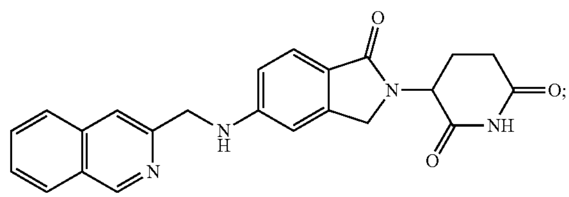
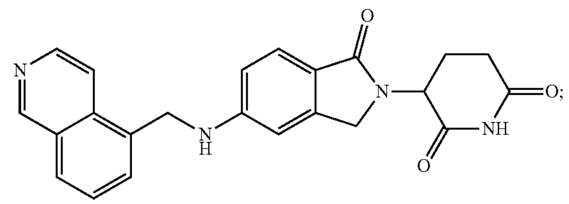
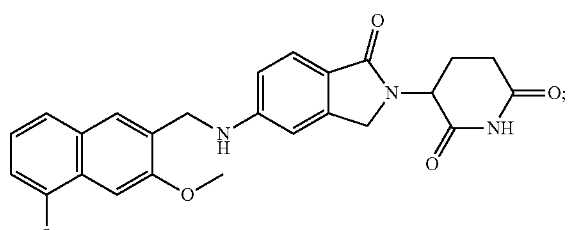
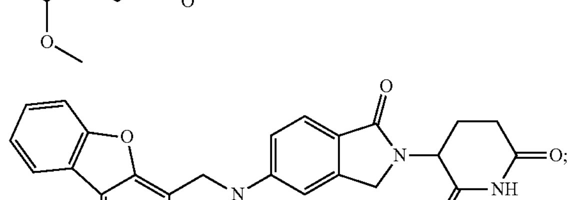
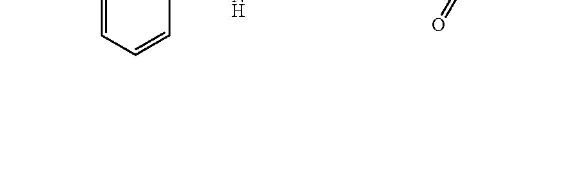
-continued
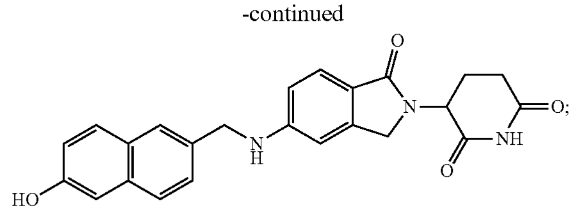
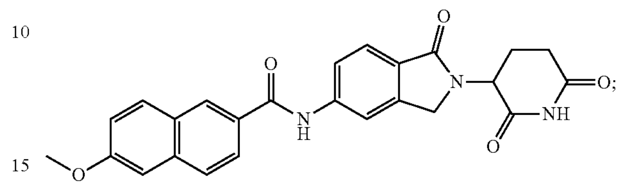
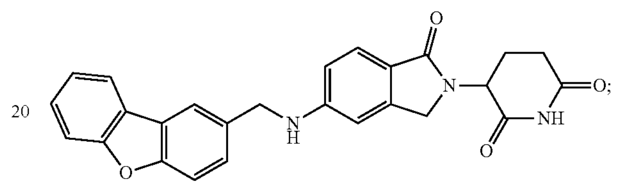
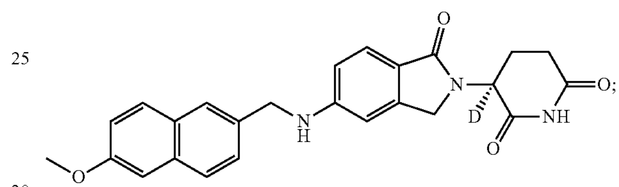
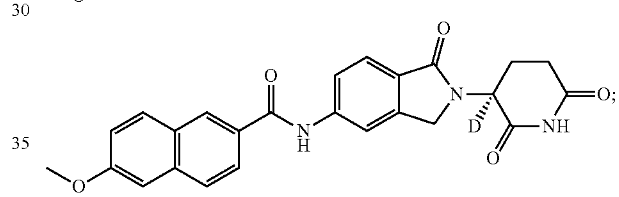
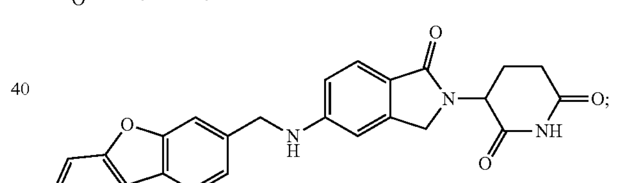
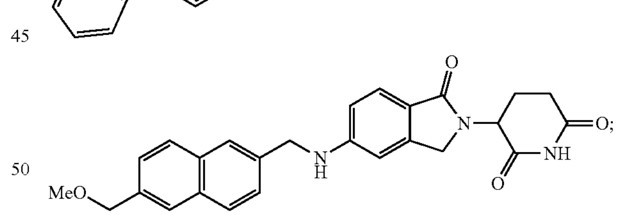
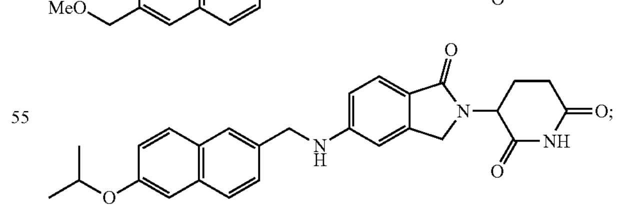
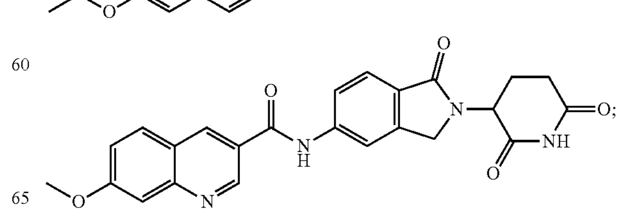
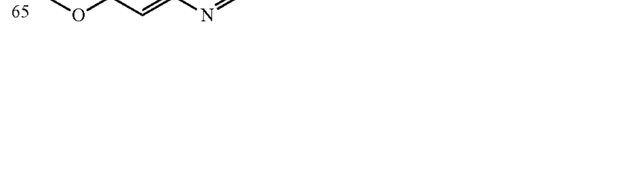

-continued

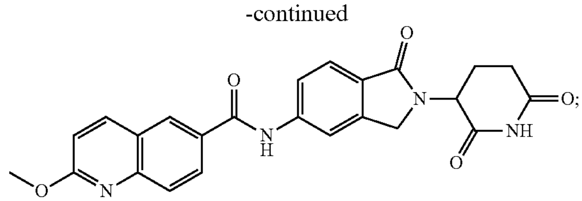

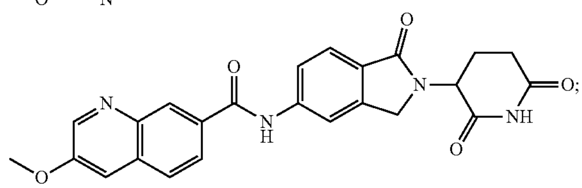

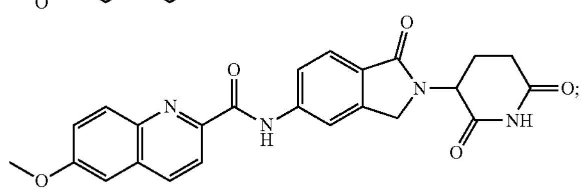

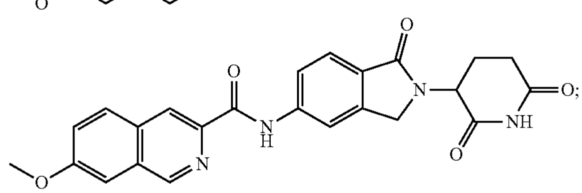

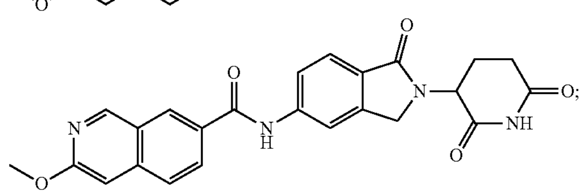

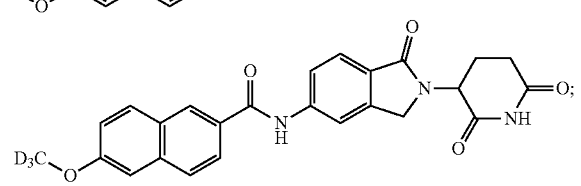

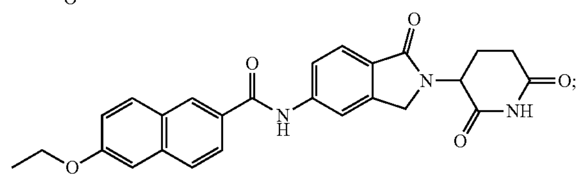

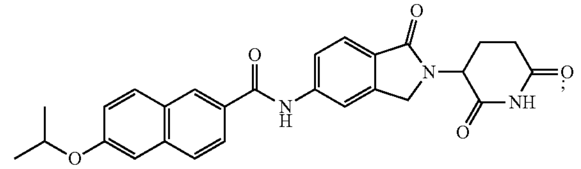

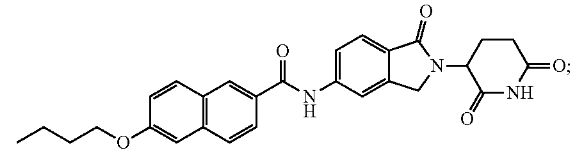

or a pharmaceutically acceptable salt thereof.

10. A pharmaceutical composition comprising a compound of claim 1, or a pharmaceutically acceptable salt thereof, and a pharmaceutically acceptable excipient.

11. A method of treating ovarian cancer, gastric cancer, or a hematological cancer in a subject in need thereof, the method comprising administering a compound of claim 1, or a pharmaceutically acceptable salt thereof, to the subject; wherein the cancer is associated with IKAROS family zinc finger 2 (IKZF2).

12. A method of promoting the degradation of IKAROS family zinc finger 2 (IKZF2), the method comprising contacting IKZF2 with a compound of claim 1, or a pharmaceutically acceptable salt thereof.

13. The method of claim 11, wherein the cancer is a leukemia or a lymphoma.

14. The compound of claim 1, wherein the compound is of formula:

(I-e)

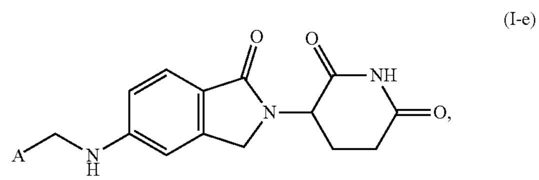

or a pharmaceutically acceptable salt thereof.

15. The compound of claim 1, wherein the compound is of formula:

(I-f)

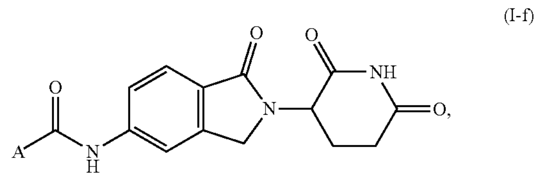

or a pharmaceutically acceptable salt thereof.

16. The compound of claim 1, wherein the compound is of formula:

(I-g)

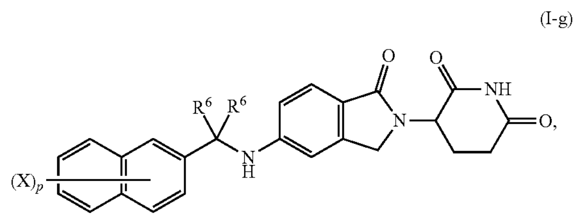

or a pharmaceutically acceptable salt thereof, wherein:

each X is, independently, halogen, —$OR^A$, or —$N(R^A)_2$;

each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom; and p is 0, 1, or 2.

17. The compound of claim 1, wherein the compound is of formula:

(I-h)

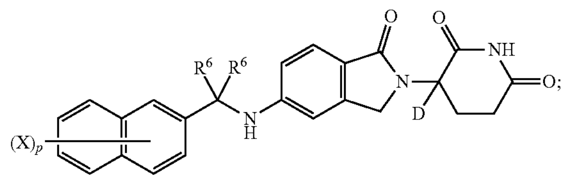

or (I-i)

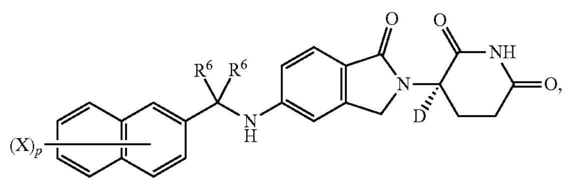

or a pharmaceutically acceptable salt thereof, wherein:

each X is, independently, halogen, —$OR^A$, or —$N(R^A)_2$;

each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom; and p is 0, 1, or 2.

18. The compound of claim 1, wherein the compound is of formula:

(I-j)

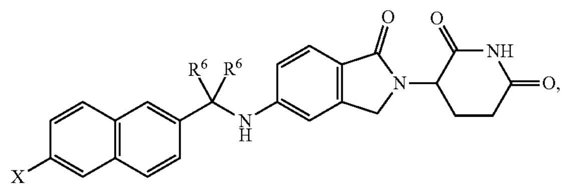

or a pharmaceutically acceptable salt thereof, wherein:

X is halogen, —$OR^A$, or —$N(R^A)_2$; and each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom.

19. The compound of claim 1, wherein the compound is of formula:

(I-k)

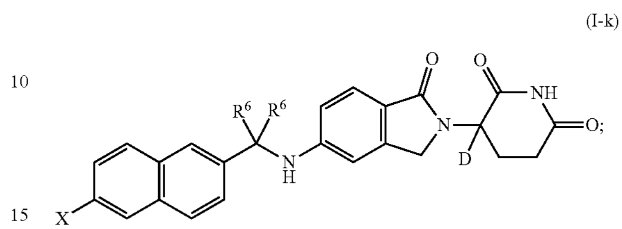

or (I-l)

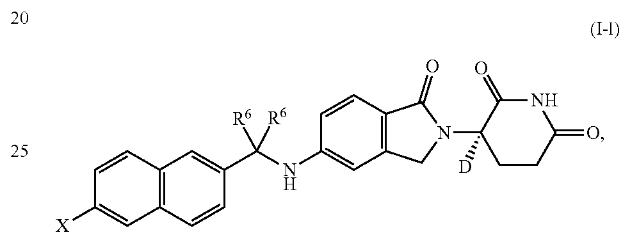

or a pharmaceutically acceptable salt thereof, wherein:

X is halogen, —$OR^A$, or —$N(R^A)_2$; and each $R^A$ is, independently, hydrogen, substituted or unsubstituted acyl, substituted or unsubstituted alkyl, an oxygen protecting group when attached to an oxygen atom, or a nitrogen protecting group when attached to a nitrogen atom.

20. The compound of claim 1, wherein the compound is of formula:

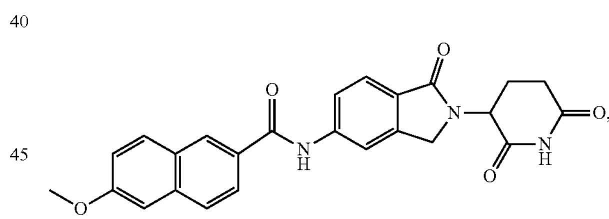

or a pharmaceutically acceptable salt thereof.

* * * * *